(12) United States Patent
Mischel et al.

(10) Patent No.: US 11,193,164 B2
(45) Date of Patent: Dec. 7, 2021

(54) METHODS OF DIAGNOSING AND TREATING CANCER TARGETING EXTRACHROMOSOMAL DNA

(71) Applicants: The Regents of the University of California, Oakland, CA (US); Ludwig Institute for Cancer Research Ltd, Zurich (CH)

(72) Inventors: Paul Mischel, Los Angeles, CA (US); Prashant Mali, San Diego, CA (US); Vineet Bafna, San Diego, CA (US); Kristen Turner, San Diego, CA (US); Viraj Deshpande, San Diego, CA (US); Doruk Beyter, San Diego, CA (US)

(73) Assignees: The Regents of the University of California, Oakland, CA (US); Ludwig Institute for Cancer Research Ltd, Zurich (CH)

( * ) Notice: Subject to any disclaimer, the term of this patent is extended or adjusted under 35 U.S.C. 154(b) by 252 days.

(21) Appl. No.: 15/989,100

(22) Filed: May 24, 2018

(65) Prior Publication Data
US 2018/0355416 A1 Dec. 13, 2018

Related U.S. Application Data

(60) Provisional application No. 62/559,111, filed on Sep. 15, 2017, provisional application No. 62/510,375, filed on May 24, 2017.

(51) Int. Cl.
*C12Q 1/6841* (2018.01)
*C12Q 1/6886* (2018.01)

(52) U.S. Cl.
CPC ......... *C12Q 1/6841* (2013.01); *C12Q 1/6886* (2013.01); *C12Q 2600/106* (2013.01)

(58) Field of Classification Search
CPC ... C12Q 1/68; C12Q 1/6886; C12Q 2600/106
See application file for complete search history.

(56) References Cited

U.S. PATENT DOCUMENTS

| 2014/0024539 A1* | 1/2014 | Craig | A61K 31/436 506/2 |
|---|---|---|---|
| 2019/0360029 A1* | 11/2019 | Verhaak | A61K 49/0008 |

OTHER PUBLICATIONS

Nathanson, et al., Targeted Therapy Resistance Mediated by Dynamic Regulation of Extrachromosomal Mutant EGFR DNA, Science, Jan. 3, 2014; 343(6166): 72-76. (Year: 2014).*
Nathanson, et al., Targeted Therapy Resistance Mediated by Dynamic Regulation of Extrachromosomal Mutant EGFR DNA, Science, Jan. 3, 2014; 343(6166): 72-76; Supplementary Materials, pp. 1-25. (Year: 2014).*
Verhaak, et al., Extrachromosomal Oncogene Amplification in Tumor Pathogenesis and Evolution, Nature Reviews Cancer, 19(5): 283-288, 2019. (Year: 2019).*
Alitalo, K et al. (Mar. 1983). "Homogeneously staining chromosomal regions contain amplified copies of an abundantly expressed cellular oncogene (c-myc) in malignant neuroendocrine cells from a human colon carcinoma," *PNAS USA* 80(6):1707-1711.
Carroll, S.M. et al. (Apr. 1988). "Double minute chromosomes can be produced from precursors derived from a chromosomal deletion," *Mol Cell Biol* 8(4):1525-1533.
Cohen, S. et al. (May 1996). "Induction of circles of heterogeneous sizes in carcinogen-treated cells: two-dimensional gel analysis of circular DNA molecules," *Mol Cell Biol* 16(5):2002-2014.
Cox. D et al. (Jul. 10, 1965). "Minute Chromatin Bodies in Malignant Tumours of Childhood," *The Lancet* 1(7402): 55-58.
Fan, Y. et al. (Feb. 2011, e-published Nov. 11, 2010). "Frequency of double minute chromosomes and combined cytogenetic abnormalities and their characteristics," *J Appl Genet* 52(1):53-59.
Haque, M.M. et al. ((Nov. 2, 2001). "Granulocytic differentiation of HL-60 cells, both spontaneous and drug-induced, might require loss of extrachromosomal DNA encoding a gene(s) not c-MYC," *Biochem Biophys Res Common* 288(3):586-591.
Kumar, P. et al. (Sep. 2017, e-published May 26, 2017). "Normal and Cancerous Tissues Release Extrachromosomal Circular DNA (eccDNA) into the Circulation," *Mol Cancer Res* 15(9):1197-1205.
L'Abbate, A. et al. (Aug. 2014, e-published Jul. 17, 2014). "Genomic organization and evolution of double minutes/homogeneously staining regions with MYC amplification in human cancer," *Nucleic Acids Res* 42(14)9131-9145.
Lubs, H.A. Jr. et al. (Feb. 1965). "The Chromosomal Complement of Human Solid Tumors. II. Karyotypes of Glial Tumors," *J Neorosorg* 22:160-168.
Lundberg, G. et al. (Aug. 29, 2008). "Binomial mitotic segregation of MYCN-carrying double minutes in neuroblastoma illustrates the role of randomness in oncogene amplification," *PLoS One* 3(8):e3099.
Nikolaev, S. et al. (Dec. 4, 2014). "Extrachromosomal driver mutations in glioblastoma and low-grade glioma," *Nat Commun* 5:5690.
Raymond, E. et al. (May 2001). "Effects of hydroxyurea on extrachromosomal DNA in patients with advanced ovarian carcinomas," *Clin Cancer Res* 7(5):1171-1180.
Sanborn, J.Z. et al. (Oct. 1, 2013, e-published Aug. 12, 2013). "Double minute chromosomes in glioblastoma multiforme are revealed by precise reconstruction of oncogenic amplicons," *Cancer Res* 73(19):6036-6045.
Storlazzi, C.T. et al. (Sep. 2010, e-published Jul. 14, 2010). "Gene amplification as double minutes or homogeneously staining regions in solid tumors: origin and structure," *Genome Res* 20(9):1198-1206.

(Continued)

*Primary Examiner* — Samuel C Woolwine
*Assistant Examiner* — Carolyn L Greene
(74) *Attorney, Agent, or Firm* — Mintz, Levin, Cohn, Ferris, Glovsky and Popeo, P.C.

(57) ABSTRACT

Provided herein are, inter alia, methods and compositions to detect, monitor and treat cancer, wherein the cancer includes amplified extrachromosomal oncogenes. The methods are useful for personalized treatment and exploit differential expression of amplified extrachromosomal oncogenes in cancer cells versus healthy cells.

10 Claims, 43 Drawing Sheets
Specification includes a Sequence Listing.

(56) References Cited

OTHER PUBLICATIONS

Van Loon, N. et al. (Jul. 11, 1994). "Formation of extrachromosomal circular DNA in HeLa cells by nonhomologous recombination," *Nocleic Acids Res* 22(13):2447-2452.

Von Hoff, D.D. et al. (Jul. 1988). "Amplified human MYC oncogenes localized to replicating submicroscopic circular DNA molecules," *PNAS USA* 85(13):4804-4808.

Von Hoff, D.D. et al. (Jun. 1990). "Double minutes arise from circular extrachromosomal DNA intermediates which integrate into chromosomal sites in human HL-60 leukemia cells," *J Clin Invest* 85(6):1887-1895.

* cited by examiner

FIGS. 16A-16B
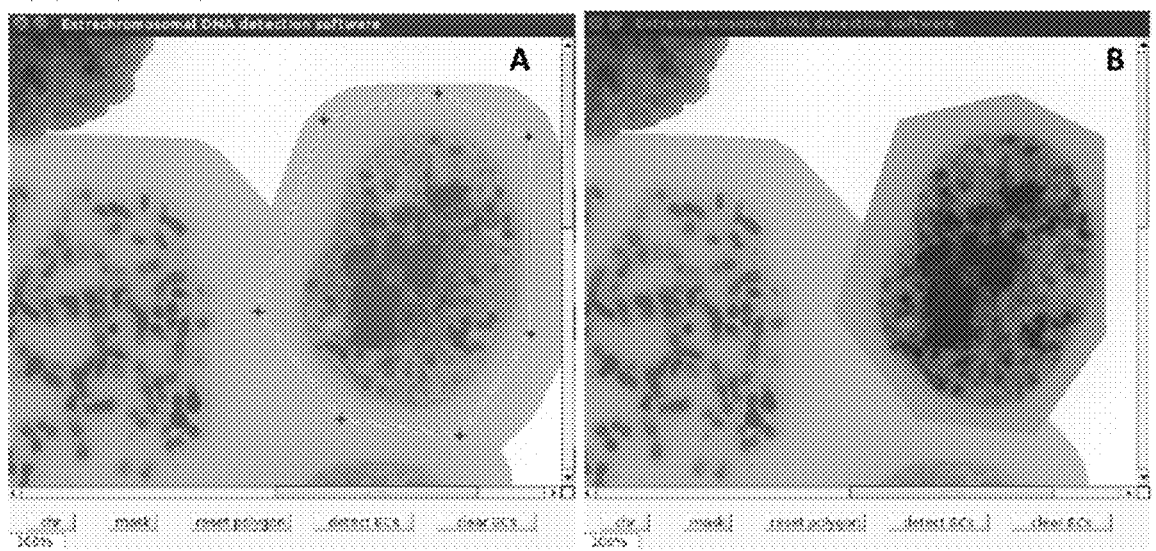
FIGS. 17A-17C
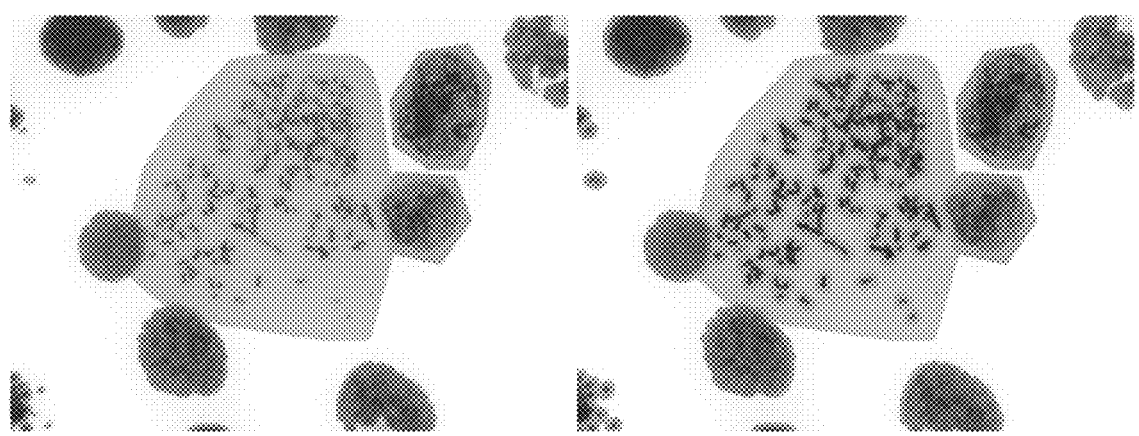
(a) Step 1: Verified ECDNA search ROI.
(b) Step 2: 15-pixel neighborhood of any larger than ECDNA structure is removed.
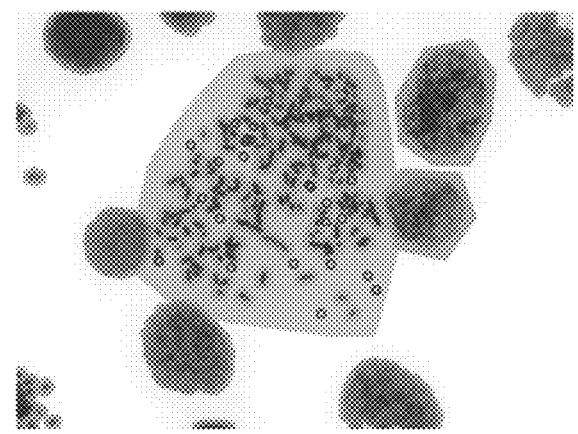
(c) Step 3: ECDNA detection on final search ROI.

METHODS OF DIAGNOSING AND TREATING CANCER TARGETING EXTRACHROMOSOMAL DNA

CROSS-REFERENCES TO RELATED APPLICATIONS

This application claims the benefit of U.S. Provisional Application No. 62/559,111 filed on Sep. 15, 2017, and U.S. Provisional Application No. 62/510,375, filed May 24, 2017, which are incorporated herein by reference in entirety and for all purposes.

REFERENCE TO A "SEQUENCE LISTING," A TABLE, OR A COMPUTER PROGRAM LISTING APPENDIX SUBMITTED AS AN ASCII FILE

The Sequence Listing written in file 048537-592001US Sequence Listing_ST25, created May 24, 2018, 3,976 bytes, machine format IBM-PC, MS Windows operating system, is hereby incorporated by reference.

BACKGROUND

Human cells have twenty-three pairs of chromosomes but in cancer, genes can be amplified in chromosomes or in circular extrachromosomal DNA (ECDNA), whose frequency and functional significance are not understood[1-4]. We performed whole genome sequencing, structural modeling and cytogenetic analyses of 17 different cancer types, including 2572 metaphases, and developed ECdetect to conduct unbiased integrated ECDNA detection and analysis. ECDNA was found in nearly half of human cancers varying by tumor type, but almost never in normal cells. Driver oncogenes were amplified most commonly on ECDNA, elevating transcript level. Mathematical modeling predicted that ECDNA amplification elevates oncogene copy number and increases intratumoral heterogeneity more effectively than chromosomal amplification, which we validated by quantitative analyses of cancer samples. These results suggest that ECDNA contributes to accelerated evolution in cancer.

Cancers evolve in rapidly changing environments from single cells into genetically heterogeneous masses. Darwinian evolution selects for those cells better fit to their environment. Heterogeneity provides a pool of mutations upon which selection can act[1,5-9]. Cells that acquire fitness-enhancing mutations are more likely to pass these mutations on to daughter cells, driving neoplastic progression and therapeutic resistance[10,11]. One common type of cancer mutation, oncogene amplification, can be found either in chromosomes or nuclear ECDNA elements, including double minutes (DMs)[2-4,12-14]. Relative to chromosomal amplicons, ECDNA is less stable, segregating unequally to daughter cells[15,16]. DMs are reported to occur in 1.4% of cancers with a maximum of 31.7% in neuroblastoma, based on the Mitelman database[4,17]. However, the scope of ECDNA in cancer has not been accurately quantified, the oncogenes contained therein have not been systematically examined, and the impact of ECDNA on tumor evolution has yet to be determined.

There is a need in the art for diagnostic tools and personalized treatment methods that make use of the differential expression of extrachromosomal DNA in cancer cell. The methods and compositions provided herein, inter alia, address these and other needs in the art.

BRIEF SUMMARY OF THE INVENTION

In one aspect is provided a method of detecting an amplified extrachromosomal oncogene in a human subject in need thereof, the method including: (i) obtaining a biological sample from a human subject; (ii) detecting whether an amplified extrachromosomal oncogene is present in the sample by contacting the biological sample with an oncogene-binding agent and detecting binding between the amplified extrachromosomal oncogene and the oncogene-binding agent.

In another aspect is provided a method of treating cancer in a subject in need thereof, the method including: (i) obtaining a biological sample from a human subject; (ii) detecting whether an amplified extrachromosomal oncogene is present in the sample by contacting the biological sample with an oncogene-binding agent and detecting binding between the amplified extrachromosomal oncogene and the oncogene-binding agent; and (iii) administering to the human subject an effective amount of an anti-cancer agent.

In another aspect is provided a method of detecting an amplified extrachromosomal oncogene in a cancer subject undergoing treatment for cancer, the method including: (i) obtaining a first biological sample from the cancer subject undergoing treatment for cancer; and (ii) detecting in the first biological sample a first level of an amplified extrachromosomal oncogene.

In another aspect is provided an extrachromosomal nucleic acid protein complex including an extrachromosomal cancer-specific nucleic acid bound to an endonuclease through an extrachromosomal cancer-specific nucleic acid binding RNA.

In another aspect is provided a method for inducing apoptosis in a cancer cell, the method including: (i) contacting a cancer cell with an effective amount of an extrachromosomal cancer-specific nucleic acid binding RNA bound to an endonuclease; (ii) allowing the extrachromosomal cancer-specific nucleic acid binding RNA to hybridize to an extrachromosomal cancer-specific nucleic acid, thereby binding the endonuclease to the extrachromosomal cancer-specific nucleic acid; and (iii) allowing the endonuclease to cleave the extrachromosomal cancer-specific nucleic acid, thereby inducing apoptosis in the cancer cell.

BRIEF DESCRIPTION OF THE DRAWINGS

FIG. 1A, Schematic diagram of experimental flow. FIG. 1B, Representative metaphases stained with DAPI and a genomic DNA FISH probe (ECDNA, arrows). FIG. 1C, DNase treatment abolishes DAPI staining of chromosomal and ECDNA (arrows). FIG. 1D, Pan-centromeric FISH reveals absence of a centromere in ECDNAs (arrows). FIG. 1E, Schematic illustration of ECdetect. FIG. 1E panel 1) DAPI-stained metaphase as input. FIG. 1E panel 2) Semi-automated identification of ECDNA search region via segmentation. FIG. 1E panel 3) Conservative filtering, removing non-ECDNA components. FIG. 1E panel 4) ECDNA detection and visualization. FIG. 1F, Pearson correlation between software-detected and manual calls of ECDNA (R: 0.98, $p<2.2\times10^{-16}$).

FIG. 2A, Distribution of ECDNA per metaphase from 72 cancer, 10 immortalized and 8 normal cell cultures, Wilcoxon rank sum test. FIG. 2B, ECDNA distribution per metaphase stratified by tumor type. FIG. 2C, Proportion of samples with ≥2 ECDNAs in ≥2 per 20 metaphases. Data shown as mean±SEM. (methods). FIG. 2D, Proportion of tumor cultures positive for ECDNA by tumor type. FIG. 2E, Shannon diversity index (SI). Each dot represents an individual cell line sampled with ≥20 metaphases. FIG. 2F, SI by tumor type. FIG. 2G, DAPI-stained metaphases with histograms.

FIG. 3A, Comparison of the frequency of focal amplifications detected by next generation sequencing of 117 cancer samples studied here, with those of matched tumor types in the TCGA, demonstrates significant overlap and representative sampling (p-value $10^{-6}$ based upon random permutations of TCGA amplicons; Methods). FIG. 3B, Localization of oncogenes by FISH. FIG. 3C, Representative FISH images of focal amplifications on ECDNA (arrows). FIG. 3D, EGFRvIII and c-Myc mRNA level, measured by qPCR (p<0.001, Mann-Whitney test), mean±SEM. n=17; each data point represents qPCR values from three technical replicates.

FIG. 4A, The selection function $f_{100}(k)$ reaches maximum for k=15, then decays logistically. FIG. 4B, Growth in amplicon copy number over time. FIG. 4C, DNA copy number stratified by oncogene location. (p<0.001, ANOVA/Tukey's multiple comparison). N=52; data points include top five amplified oncogenes, mean±SEM. FIG. 4D, Change in heterogeneity (SI) over time. FIG. 4E, Correlation between copy number and heterogeneity. FIG. 4F, Experimental data showing correlation between ECDNA counts and heterogeneity matches the simulation in panel E.

FIG. 5A, Images corresponding to FIG. 1B, FIG. 5B, images corresponding to FIG. 1C, FIG. 5C, images corresponding to FIG. 1D.

FIG. 12A, FISH images revealed EGFR gene on ECDNAs (top) and HSRs (bottom) on different passes of the GBM39 cell line. Analysis of the HSR FISH images shows evidence of multiple integration sites on different chromosomes. FIG. 12B, Next generation sequencing of DNA from 4 independent cultures of GBM39 was used to analyze the fine structure of amplifications (Supplementary Material Section 4.3). In 3 biological replicates (rows 1 to 3) of these cultures, EGFRvIII was exclusively on ECDNA, while one of the later passage cultures (row 4) was found to contain EGFRvIII entirely on HSRs, with no detectable ECDNA. The DNA derived from different ECDNA cultures shows identical structure with some heterogeneity (p<$2.18 \times 10^{-8}$ for all pairs), suggesting common origin. However, DNA derived from HSRs reveals a conserved structure that is identical to ECDNA structure (p<$1.98 \times 10^{-5}$, Supplementary Material Section 2.4), possibly with tandem duplications. FIG. 12C, A possible progression of normal genome to cancer genome with EGFRvIII ECDNAs and amplification to a copy count of around 100 copies. The EGFRvIII ECDNAs possibly aggregate into tandem duplications and reintegrate into multiple chromosomes as HSRs such that 5-6 HSRs accommodate around 100 copies of EGFRvIII.

FIG. 13A, FISH images of naive GBM39 cells, in response to Erlotinib Treatment (ERZ) and Drug Withdrawal displayed EC amplification, HSR amplification and EC amplification respectively (top to bottom). FIG. 13B, Next generation sequencing of DNA from 6 independent cultures of GBM39 was used to analyze the fine structure of amplifications (Supplementary Material Section 4.3). Average copy numbers of amplified intervals as determined from sequencing analysis in naive samples (biological replicates in rows 1 to 3): 110 to 150, ERZ sample (row 4): 5.4 and Erlotinib removed (biological replicates in rows 5 and 6): 100-105. All three categories show similar fine structure indicating common origin (Methods). Erlotinib removed replicates show additional rearrangements and heterogeneity as compared to naive samples. FIG. 13C, Cytogenetic and sequencing progression suggests the EGFRvIII ECDNAs in naive cells get reintegrated into HSRs after drug application and the copies in the HSRs break off from the chromosomes again to form ECDNAs with copy count similar to naive cells. Drug removed samples also show additional heterogeneity in structure.

FIG. 15A shows pre-segmented and original DAPI images. FIG. 15B shows overview of pre-segmentation.

FIGS. 16A-16B. The figures show non-chromosomal region masking. FIG. 16A shows selection of the undesired region. FIG. 16B shows masking and removing from the ECDNA search ROI.

FIGS. 17A-17C. The figures show ECDNA detection steps. FIG. 17A shows step 1: verified ECDNA search ROI. FIG. 17B shows step 2: 15-pixel neighborhood of any larger than ECDNA structure is removed. FIG. 17C shows step 3: ECDNA detection on final search ROI.

FIG. 19A shows cell line RXF623-003. FIG. 19B shows cell line OVCAR3-013. FIG. 19C shows cell line H23-032. FIG. 19D shows cell line M14-042. FIG. 19E shows cell line A549-029. FIG. 19F shows cell line M14-004.

The ratio of birth to death rate for a cell with k amplicon copies is given by $1+sf_m(k)$. 39B: Growth of cells over time with EC amplicon compared to growth with intrachromosomal amplification (HSR) with duplication probabilities 0.1; 0.05; 0.01. The dotted lines represent the number of cells containing amplicons, starting with 100 amplicon containing cells, while solid lines depict the total number of cells in the population. 39C: Increase in average amplicon copy number over time. 39D: Change in Shannon entropy with time. 39E: Change in entropy compared to change in copy number.

FIGS. 40A-40E. The figures show tumor evolution with $N_0=10^5$, s=1.0, m=300. 40A: The selection function $f_{300}(k)$. The ratio of birth to death rate for a cell with k amplicon copies is given by $1+sf_m(k)$. 40B: Growth of cells over time with EC amplicon compared to growth with intrachromosomal amplification (HSR) with duplication probabilities 0.1; 0.05; 0.01. The dotted lines represent the number of cells containing amplicons, starting with 100 amplicon containing cells, while solid lines depict the total number of cells in the population. 40C: Increase in average amplicon copy number over time. 40D: Change in Shannon entropy with time. 40E: Change in entropy compared to change in copy number.

FIGS. 41A-41E. The figures show tumor evolution with $N_0=10^5$, s=1.0, m=600. 41A: The selection function $f_{100}(k)$. The ratio of birth to death rate for a cell with k amplicon copies is given by $1+sf_m(k)$. 41B: Growth of cells over time with EC amplicon compared to growth with intrachromosomal amplification (HSR) with duplication probabilities 0.1; 0.05; 0.01. The dotted lines represent the number of cells containing amplicons, starting with 100 amplicon containing cells, while solid lines depict the total number of cells in the population. 41C: Increase in average amplicon copy number over time. 41D: Change in Shannon entropy with time. 41E: Change in entropy compared to change in copy number.

FIGS. 42A-42D. The figures show tumor evolution trajectories with $N_0=10^5$, s=1.0, m=50. 42A: The selection function $f_{50}(k)$. The ratio of birth to death rate for a cell with k amplicon copies is given by $1+sf_m(k)$. 42B-42D: 10 simulation trajectories showing growth of cells over time (42B); Increase in average amplicon copy number over time (42C); and, Change in Shannon entropy with time (42D). The trajectories are consistent, with variation due to difference in 'establishment time' of amplicon containing cells.

Figure 43:
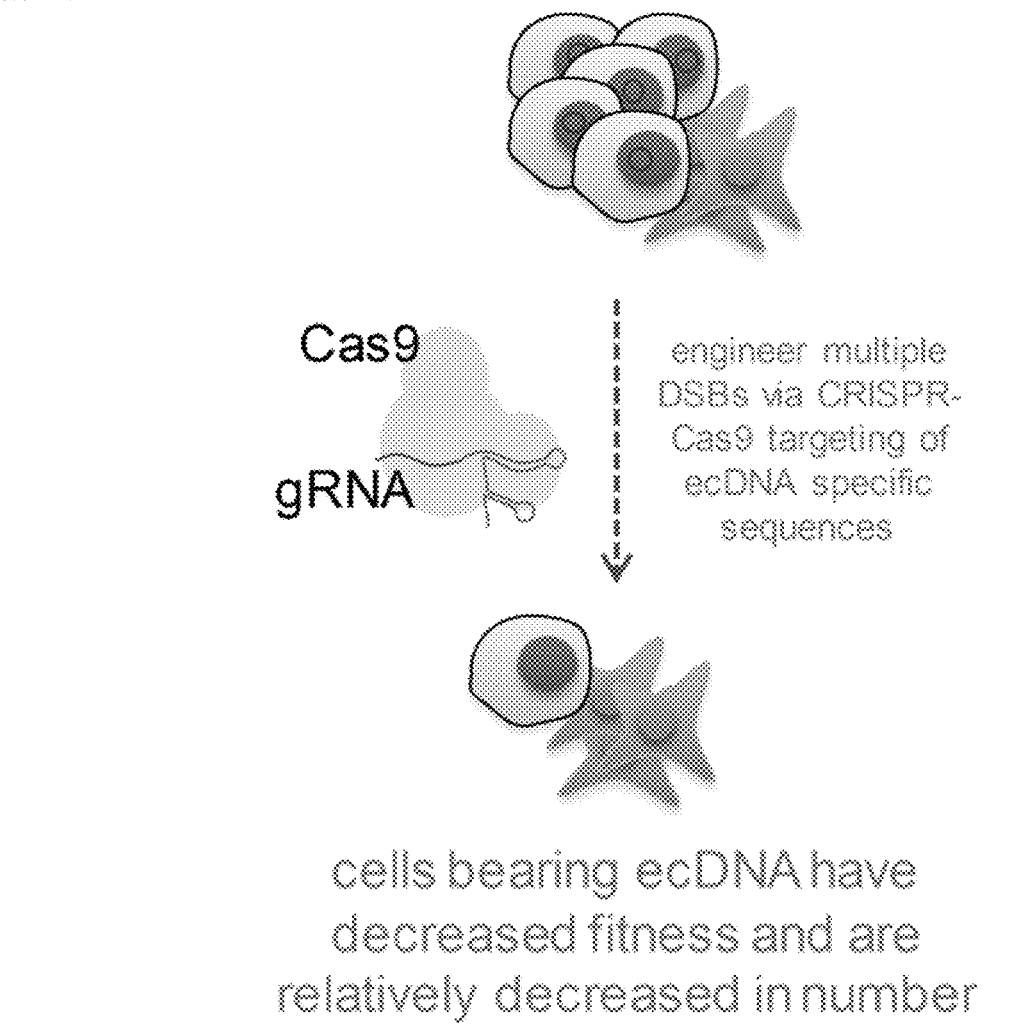
Figure 43:
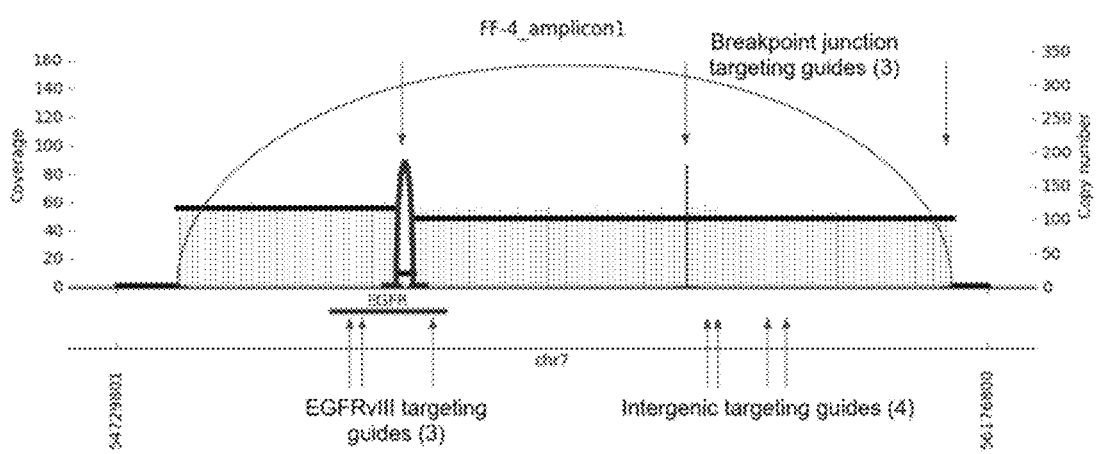

FIG. 43. The figure illustrates cancer therapeutics via engineering of ecDNA specific double strand breaks (DSBs). Engineering DSBs on ecDNA specific targets via genome engineering tools, e.g. CRISPRs/ZFNs/TALENs/mega-nucleases, could enable highly specific therapeutic killing or impaired growth of cancer cells that bear them, without any risk of genomic off-targeting in normal bystander cells which may take up the targeting agents. Multiple double-strand breaks (DSBs) can adversely impact cellular fitness. ecDNA are present in multiple copies, and typically bear unique sequences not found on the normal genome, e.g. junction sequences. We propose to deliver corresponding genome-engineer tools either via: 1) adeno-associated viruses, 2) oncolytic viruses, or 3) as naked proteins or ribonucleoprotein complexes bearing cell penetrating peptides, such as via multiple tethered copies of the SV40 NLS, or poly arginine tracts, and/or the HIV TAT protein.

Figure 44:
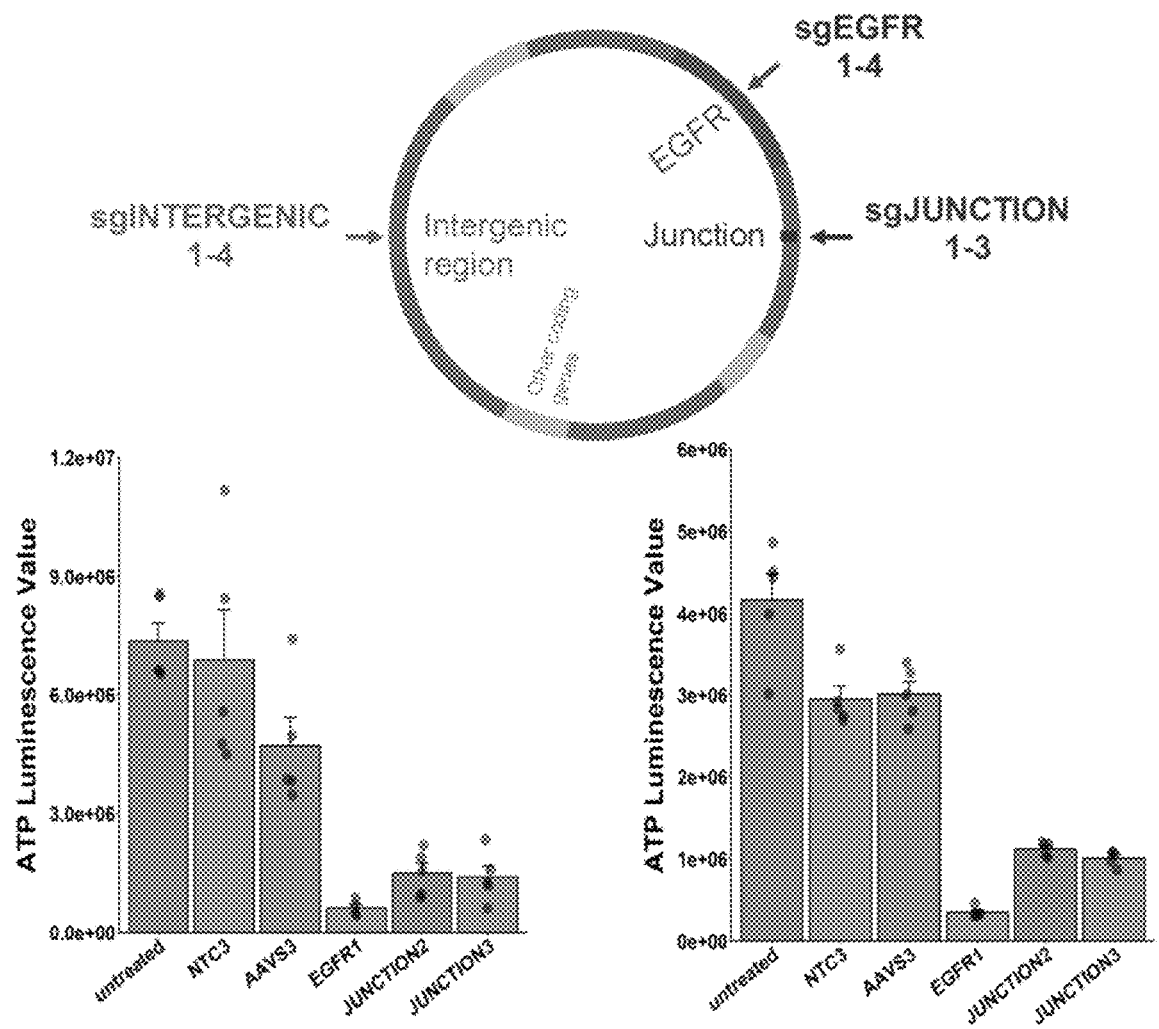

FIG. 44. The figure shows CRISPR-Cas9 targeting of unique junctions on ecDNA leads to markedly decreased viability of cancer cells.

Figure 45:
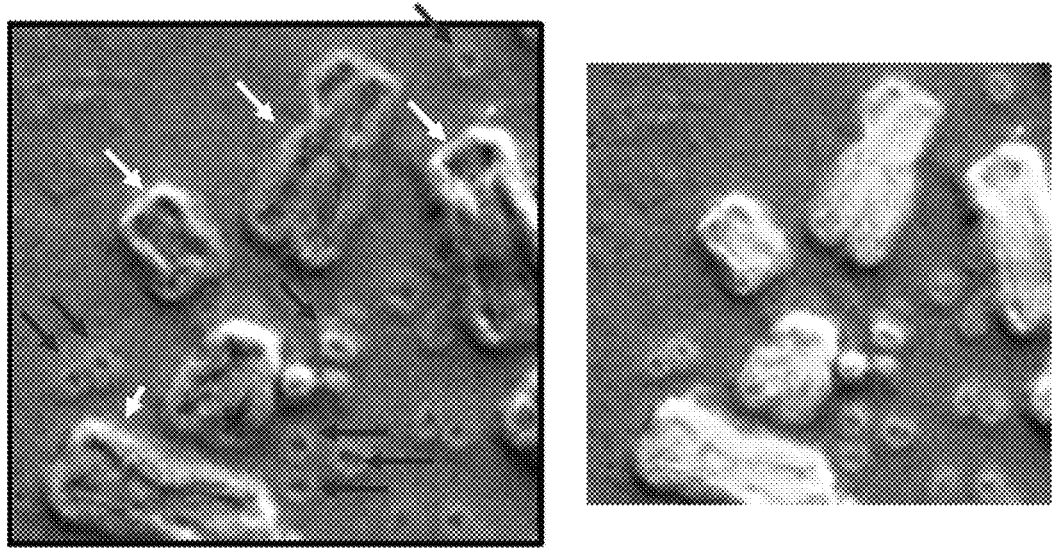

FIG. 45. The figure shows unambiguous proof that extrachromosomal DNA in cancer is circular. Data using the amplicon architect software we developed (Turner et al., Nature, 2017) indicates that oncogene-containing extrachromosomal DNA is circular. Circular DNA is structurally distinct from chromosomal DNA, creating different structural and functional properties and vulnerabilities. However, the circularity of ecDNA in cancer has never been conclusively visual demonstrated. We performed scanning electron of tumor cell metaphases, coupled with structured illumination microscopy of the same metaphases stained with the DNA binding dye DAPI to resolve the structure of ecDNA in 3 different cancer types—colon cancer, prostate cancer and glioblastoma. In the figure, the scanning electron microscopy of COLO320 colon cancer cells reveals circular DNA (dark grey arrows), and normal linear chromosomes (white arrows). Overlap of the scanning electron microscopy image with DAPI staining shows that the circular structures are DNA, as they stain blue with DAPI.

DETAILED DESCRIPTION

Definitions

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

The abbreviations used herein have their conventional meaning within the chemical and biological arts. The chemical structures and formulae set forth herein are constructed according to the standard rules of chemical valency known in the chemical arts.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, N.Y. 1994); Sambrook et al., MOLECULAR CLONING, A LABORATORY MANUAL, Cold Springs Harbor Press (Cold Springs Harbor, N Y 1989). Any methods, devices and materials similar or equivalent to those described herein can be used in the practice of this invention. The following definitions are provided to facilitate understanding of certain terms used frequently herein and are not meant to limit the scope of the present disclosure.

As used herein, the term "about" means a range of values including the specified value, which a person of ordinary skill in the art would consider reasonably similar to the specified value. In embodiments, the term "about" means within a standard deviation using measurements generally acceptable in the art. In embodiments, about means a range extending to +/−10% of the specified value. In embodiments, about means the specified value.

The term "small molecule" as used herein refers to a low molecular weight organic compound that may regulate a biological process. In embodiments, small molecules are drugs. In embodiments, small molecules have a molecular weight less than 900 daltons. In embodiments, small molecules are of a size on the order of one nanometer.

The term "organic compound" as used herein refers to any of a large class of chemical compounds in which one or more atoms of carbon are covalently linked to atoms of other elements.

"Nucleic acid" refers to deoxyribonucleotides or ribonucleotides and polymers thereof in either single- or double-stranded form, and complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA. Nucleic acid as used herein also refers to nucleic acids that have the same basic chemical structure as a naturally occurring nucleic acid. Such analogues have modified sugars and/or modified ring substituents, but retain the same basic chemical structure as the naturally occurring nucleic acid. A nucleic acid mimetic refers to chemical compounds that have a structure that is different from the general chemical structure of a nucleic acid, but that functions in a manner similar to a naturally occurring nucleic acid. Examples of such analogues include, without limitation, phosphorothiolates, phosphoramidates, methyl phosphonates, chiral-methyl phosphonates, 2-O-methyl ribonucleotides, and peptide-nucleic acids (PNAs).

Nucleic acids, including nucleic acids with a phosphothioate backbone can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amino acid on a protein or polypeptide through a covalent, non-covalent or other interaction.

The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphodiester derivatives including, e.g., phosphoramidate, phosphorodiamidate, phosphorothioate (also known as phosphothioate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA)), including those described in U.S. Pat. Nos. 5,235,033 and 5,034,506, and Chapters 6 and 7, ASC Symposium Series 580, *Carbohydrate Modifications in Antisense Research*, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

The term "gene" means the segment of DNA involved in producing a protein; it includes regions preceding and following the coding region (leader and trailer) as well as intervening sequences (introns) between individual coding segments (exons). The leader, the trailer, as well as the introns, include regulatory elements that are necessary during the transcription and the translation of a gene. Further, a "protein gene product" is a protein expressed from a particular gene.

The term "EGFR" or "EGFR protein" as provided herein includes any of the recombinant or naturally-occurring forms of the epidermal growth factor receptor (EGFR) or variants or homologs thereof that maintain EGFR activity (e.g. within at least 50%, 80%, 90%, 95%, 96%, 97%, 98%, 99% or 100% activity compared to EGFR). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring EGFR. In embodiments, EGFR is the protein as identified by the NCBI sequence reference GI: 29725609, homolog or functional fragment thereof.

The term "c-Myc" as provided herein includes any of the recombinant or naturally-occurring forms of the cancer Myelocytomatosis (c-Myc) or variants or homologs thereof that maintain c-Myc activity (e.g. within at least 50%, 80%, 90%, 95%, 96%, 97%, 98%, 99% or 100% activity compared to c-Myc). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring c-Myc. In embodiments, c-Myc is the protein as identified by Accession No. Q6LBK7, homolog or functional fragment thereof.

The terms "N-Myc" as provided herein includes any of the recombinant or naturally-occurring forms of the N-myc proto-oncogene protein (N-Myc) or variants or homologs thereof that maintain N-Myc activity (e.g. within at least 50%, 80%, 90%, 95%, 96%, 97%, 98%, 99% or 100% activity compared to N-Myc). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring N-Myc. In embodiments, N-Myc is the protein as identified by Accession No. P04198, homolog or functional fragment thereof.

The terms "cyclin D1" as provided herein includes any of the recombinant or naturally-occurring forms of the cyclin D1 protein (cyclin D1) or variants or homologs thereof that maintain cyclin D1 activity (e.g. within at least 50%, 80%, 90%, 95%, 96%, 97%, 98%, 99% or 100% activity compared to cyclin D1). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring cyclin D1. In embodiments, cyclin D1 is the protein as identified by Accession No. P24385, homolog or functional fragment thereof.

The terms "ErbB2", or "erythroblastic oncogene B," as provided herein includes any of the recombinant or naturally-occurring forms of the receptor tyrosine-protein kinase erbB-2 (ErbB2) or variants or homologs thereof that maintain ErbB2activity (e.g. within at least 50%, 80%, 90%, 95%, 96%, 97%, 98%, 99% or 100% activity compared to ErbB2). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring ErbB2. In embodiments, ErbB2 is the protein as identified by Accession No. P04626, homolog or functional fragment thereof.

The terms "CDK4", or "cyclin-dependent kinase 4" as provided herein includes any of the recombinant or naturally-occurring forms of the cyclin dependent kinase 4 (CDK4) or variants or homologs thereof that maintain CDK4activity (e.g. within at least 50%, 80%, 90%, 95%, 96%, 97%, 98%, 99% or 100% activity compared to CDK4). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CDK4. In embodiments, CDK4 is the protein as identified by Accession No. P11802, homolog or functional fragment thereof.

The terms "CDK6", or "cyclin-dependent kinase 6" as provided herein includes any of the recombinant or naturally-occurring forms of the cyclin dependent kinase 6 (CDK6) or variants or homologs thereof that maintain CDK6activity (e.g. within at least 50%, 80%, 90%, 95%, 96%, 97%, 98%, 99% or 100% activity compared to CDK6). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CDK6. In embodiments, CDK6 is the protein as identified by Accession No. Q00534, homolog or functional fragment thereof.

The terms "BRAF" as provided herein includes any of the recombinant or naturally-occurring forms of the serine/threonine-protein kinase B-Raf (BRAF) or variants or homologs thereof that maintain BRAF activity (e.g. within at least 50%, 80%, 90%, 95%, 96%, 97%, 98%, 99% or 100% activity compared to BRAF). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring BRAF. In embodiments, BRAF is the protein as identified by Accession No. P15056, homolog or functional fragment thereof.

The terms "MDM2", or "mouse double minute 2" as provided herein includes any of the recombinant or naturally-occurring forms of the mouse double minute 2 homolog (MDM2) or variants or homologs thereof that maintain MDM2 activity (e.g. within at least 50%, 80%, 90%, 95%, 96%, 97%, 98%, 99% or 100% activity compared to MDM2). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring MDM2. In embodiments, MDM2 is the protein as identified by Accession No. Q00987, homolog or functional fragment thereof.

The terms "MDM4", or "mouse double minute 4" as provided herein includes any of the recombinant or naturally-occurring forms of the mouse double minute 4 homolog (MDM4) or variants or homologs thereof that maintain MDM4 activity (e.g. within at least 50%, 80%, 90%, 95%, 96%, 97%, 98%, 99% or 100% activity compared to MDM4). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring MDM4. In embodiments, MDM4 is the protein as identified by Accession No. O15151, homolog or functional fragment thereof.

The term "extrachromosomal DNA" or "ecDNA" as used herein, refers to a deoxyribonucleotide polymer having a chromosomal composition (including histone proteins) that does not form part of a cellular chromosome. ecDNA molecules have a circular structure and are not linear, as compared to cellular chromosomes.

As used herein, the term "oncogene" refers to a gene capable of transforming a healthy cell into a cancer cell due to mutation or increased expression levels of said gene relative to a healthy cell. The terms "amplified oncogene" or "oncogene amplification" refer to an oncogene being present at multiple copy numbers (e.g., at least 2 or more) in a chromosome. Likewise, an "amplified extrachromosomal oncogene" is an oncogene, which is present at multiple copy numbers and the multiple copies of said oncogene form part of an extrachromosomal DNA molecule. In embodiments, the oncogene forms part of an extrachromosomal DNA. In embodiments, the amplified oncogene forms part of an extrachromosomal DNA. In embodiments, the extrachromosomal oncogene is EGFR. In embodiments, the extrachromosomal oncogene is c-Myc. In embodiments, the extrachromosomal oncogene is N-Myc. In embodiments, the extrachromosomal oncogene is cyclin D1. In embodiments, the extrachromosomal oncogene is ErbB2. In embodiments, the extrachromosomal oncogene is CDK4. In embodiments, the extrachromosomal oncogene is CDK6. In embodiments, the extrachromosomal oncogene is BRAF. In embodiments, the extrachromosomal oncogene is MDM2. In embodiments, the extrachromosomal oncogene is MDM4.

The word "expression" or "expressed" as used herein in reference to a gene means the transcriptional and/or translational product of that gene. The level of expression of a DNA molecule in a cell may be determined on the basis of either the amount of corresponding mRNA that is present within the cell or the amount of protein encoded by that DNA produced by the cell. The level of expression of non-coding nucleic acid molecules (e.g., siRNA) may be detected by standard PCR or Northern blot methods well known in the art. See, Sambrook et al., 1989 *Molecular Cloning: A Laboratory Manual,* 18.1-18.88.

Expression of a transfected gene can occur transiently or stably in a cell. During "transient expression" the transfected gene is not transferred to the daughter cell during cell division. Since its expression is restricted to the transfected cell, expression of the gene is lost over time. In contrast, stable expression of a transfected gene can occur when the gene is co-transfected with another gene that confers a selection advantage to the transfected cell. Such a selection advantage may be a resistance towards a certain toxin that is presented to the cell.

The term "plasmid" or "expression vector" refers to a nucleic acid molecule that encodes for genes and/or regulatory elements necessary for the expression of genes. Expression of a gene from a plasmid can occur in cis or in trans. If a gene is expressed in cis, gene and regulatory elements are encoded by the same plasmid. Expression in trans refers to the instance where the gene and the regulatory elements are encoded by separate plasmids.

As used herein, the term "vector" refers to a nucleic acid molecule capable of transporting another nucleic acid to which it has been linked. One type of vector is a "plasmid", which refers to a linear or circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions. Additionally, some viral vectors are capable of targeting a particular cells type either specifically or non-specifically. Replication-incompetent viral vectors or replication-defective viral vectors refer to viral vectors that are capable of infecting their target cells and delivering their viral payload, but then fail to continue the typical lytic pathway that leads to cell lysis and death.

The terms "transfection", "transduction", "transfecting" or "transducing" can be used interchangeably and are defined as a process of introducing a nucleic acid molecule and/or a protein to a cell. Nucleic acids may be introduced to a cell using non-viral or viral-based methods. The nucleic acid molecule can be a sequence encoding complete proteins or functional portions thereof. Typically, a nucleic acid vector, comprising the elements necessary for protein expression (e.g., a promoter, transcription start site, etc.). Non-viral methods of transfection include any appropriate method that does not use viral DNA or viral particles as a delivery system to introduce the nucleic acid molecule into the cell. Exemplary non-viral transfection methods include calcium phosphate transfection, liposomal transfection, nucleofection, sonoporation, transfection through heat shock, magnetifection and electroporation. For viral-based methods, any useful viral vector can be used in the methods described herein. Examples of viral vectors include, but are not limited to retroviral, adenoviral, lentiviral and adeno-associated viral vectors. In some aspects, the nucleic acid molecules are introduced into a cell using a retroviral vector following standard procedures well known in the art. The terms "transfection" or "transduction" also refer to introducing proteins into a cell from the external environment. Typically, transduction or transfection of a protein relies on attachment of a peptide or protein capable of crossing the cell membrane to the protein of interest. See, e.g., Ford et al. (2001) Gene Therapy 8:1-4 and Prochiantz (2007) Nat. Methods 4:119-20.

The terms "transcription start site" and transcription initiation site" may be used interchangeably to refer herein to the 5' end of a gene sequence (e.g., DNA sequence) where RNA polymerase (e.g., DNA-directed RNA polymerase) begins synthesizing the RNA transcript. The transcription start site may be the first nucleotide of a transcribed DNA sequence where RNA polymerase begins synthesizing the RNA transcript. A skilled artisan can determine a transcription start site via routine experimentation and analysis, for example, by performing a run-off transcription assay or by definitions according to FANTOM5 database.

The term "promoter" as used herein refers to a region of DNA that initiates transcription of a particular gene. Promoters are typically located near the transcription start site of a gene, upstream of the gene and on the same strand (i.e., 5' on the sense strand) on the DNA. Promoters may be about 100 to about 1000 base pairs in length.

The term "enhancer" as used herein refers to a region of DNA that may be bound by proteins (e.g., transcription factors) to increase the likelihood that transcription of a gene will occur. Enhancers may be about 50 to about 1500 base pairs in length. Enhancers may be located downstream or upstream of the transcription initiation site that it regulates and may be several hundreds of base pairs away from the transcription initiation site.

The term "silencer" as used herein refers to a DNA sequence capable of binding transcription regulation factors known as repressors, thereby negatively effecting transcription of a gene. Silencer DNA sequences may be found at many different positions throughout the DNA, including, but not limited to, upstream of a target gene for which it acts to repress transcription of the gene (e.g., silence gene expression).

A "guide RNA" or "gRNA" as provided herein refers to any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that may be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids sequences encode any given amino acid residue. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

The terms "polypeptide," "peptide" and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "antibody" refers to a polypeptide encoded by an immunoglobulin gene or functional fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The term "aptamer" as used herein refers to an oligonucleotide or peptide molecule that binds to a specific target molecule.

The term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, 95%, 98%, or 99% identity over a specified region, e.g., of the entire polypeptide sequences of the invention or individual domains of the polypeptides of the invention), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. Optionally, the identity exists over a region that is at least about 50 nucleotides in length, or more preferably over a region that is 100 to 500 or 1000 or more nucleotides in length. The present invention includes polypeptides that are substantially identical to any of SEQ ID NOs: 1, 2, 3, 4, and 5.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of, e.g., a full length sequence or from 20 to 600, about 50 to about 200, or about 100 to about 150 amino acids or nucleotides in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

An example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross-reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The words "complementary" or "complementarity" refer to the ability of a nucleic acid in a polynucleotide to form a base pair with another nucleic acid in a second polynucleotide. For example, the sequence A-G-T is complementary to the sequence T-C-A. Complementarity may be partial, in which only some of the nucleic acids match according to base pairing, or complete, where all the nucleic acids match according to base pairing.

As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part 1, Second Chapter "Overview of principles of hybridization and the strategy of nucleic acid probe assay", Elsevier, N.Y.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence.

"Contacting" is used in accordance with its plain ordinary meaning and refers to the process of allowing at least two distinct species (e.g. nucleic acids and/or proteins) to become sufficiently proximal to react, interact or physically touch. It should be appreciated, that the resulting reaction product can be produced directly from a reaction between the added reagents or from an intermediate from one or more of the added reagents which can be produced in the reaction mixture.

The term "contacting" may include allowing two or more species to react, interact, or physically touch (e.g., bind), wherein the two or more species may be, for example, an extrachromosomal cancer-specific nucleic acid as described herein, aextrachromosomal cancer-specific nucleic acid binding RNA as described herein, and an endonuclease as described herein. In embodiments, contacting includes, for example, allowing an extrachromosomal cancer-specific nucleic acid, a cancer-specific nucleic acid binding RNA, and an endonuclease to contact one another to form an extrachromosomal nucleic acid peptide complex.

As used herein, the terms "binding," "specific binding" or "specifically binds" refer to two or more molecules forming a complex (e.g., an extrachromosomal nucleic acid protein complex) that is relatively stable under physiologic conditions.

A "cell" as used herein, refers to a cell carrying out metabolic or other functions sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., *spodoptera*) and human cells. Cells may be useful when they are naturally nonadherent or have been treated not to adhere to surfaces, for example by trypsinization.

"Biological sample" or "sample" refer to materials obtained from or derived from a subject or patient. A biological sample includes sections of tissues such as biopsy and autopsy samples, and frozen sections taken for histological purposes. Such samples include bodily fluids such as blood and blood fractions or products (e.g., serum, plasma, platelets, red blood cells, and the like), sputum, tissue, cultured cells (e.g., primary cultures, explants, and transformed cells) stool, urine, synovial fluid, joint tissue, synovial tissue, synoviocytes, fibroblast-like synoviocytes, macrophage-like synoviocytes, immune cells, hematopoietic cells, fibroblasts, macrophages, T cells, etc. A biological sample is typically obtained from a eukaryotic organism, such as a mammal such as a primate e.g., chimpanzee or human; cow; dog; cat; a rodent, e.g., guinea pig, rat, mouse; rabbit; or a bird; reptile; or fish. In some embodiments, the sample is obtained from a human.

A "control" or "standard control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of side effects). One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

"Patient" or "subject in need thereof" refers to a living organism suffering from or prone to a disease or condition that can be treated by administration of a composition or pharmaceutical composition as provided herein. Non-limiting examples include humans, other mammals, bovines, rats, mice, dogs, monkeys, goat, sheep, cows, deer, and other non-mammalian animals. In some embodiments, a patient is human.

The terms "disease" or "condition" refer to a state of being or health status of a patient or subject capable of being treated with a compound, pharmaceutical composition, or method provided herein. In embodiments, the disease is cancer (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma (Mantel cell lymphoma), head and neck cancer, colorectal cancer, prostate cancer, pancreatic cancer, melanoma, breast cancer, neuroblastoma).

As used herein, the term "cancer" refers to all types of cancer, neoplasm or malignant tumors found in mammals, including leukemias, lymphomas, melanomas, neuroendocrine tumors, carcinomas and sarcomas. Exemplary cancers that may be treated with a compound, pharmaceutical composition, or method provided herein include lymphoma (e.g., Mantel cell lymphoma, follicular lymphoma, diffuse large B-cell lymphoma, marginal zona lymphoma, Burkitt's lymphoma), sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g. triple negative, ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g., hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme, glioma, melanoma, prostate cancer, castration-resistant prostate cancer, breast cancer, triple negative breast cancer, glioblastoma, ovarian cancer, lung cancer, squamous cell carcinoma (e.g., head, neck, or esophagus), colorectal cancer, leukemia (e.g., lymphoblastic leukemia, chronic lymphocytic leukemia, hairy cell leukemia), acute myeloid leukemia, lymphoma, B cell lymphoma, or multiple myeloma. Additional examples include, cancer of the thyroid, endocrine system, brain, breast, cervix, colon, head & neck, esophagus, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). The P388 leukemia model is widely accepted as being predictive of in vivo anti-leukemic activity. It is believed that a compound that tests positive in the P388 assay will generally exhibit some level of anti-leukemic activity in vivo regardless of the type of leukemia being treated. Accordingly, the present application includes a method of treating leukemia, and, preferably, a method of treating acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, and undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound, pharmaceutical composition, or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound, pharmaceutical composition, or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound, pharmaceutical composition, or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, ductal carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tubular carcinoma, tuberous carcinoma, verrucous carcinoma, or carcinoma villosum.

As used herein, the terms "metastasis," "metastatic," and "metastatic cancer" can be used interchangeably and refer to the spread of a proliferative disease or disorder, e.g., cancer, from one organ or another non-adjacent organ or body part.

Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

The term "associated" or "associated with" in the context of a substance or substance activity or function associated with a disease (e.g., cancer (e.g. leukemia, lymphoma, B cell lymphoma, or multiple myeloma)) means that the disease (e.g. cancer, (e.g. leukemia, lymphoma, B cell lymphoma, or multiple myeloma)) is caused by (in whole or in part), or a symptom of the disease is caused by (in whole or in part) the substance or substance activity or function.

The term "prevent" refers to a decrease in the occurrence of disease symptoms in a patient. As indicated above, the prevention may be complete (no detectable symptoms) or partial, such that fewer symptoms are observed than would likely occur absent treatment.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. In embodiments, the administering does not include administration of any active agent other than the recited active agent.

"Co-administer" it is meant that a composition described herein is administered at the same time, just prior to, or just after the administration of one or more additional therapies. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present invention can be delivered transdermally, by a topical route, or formulated as applicator sticks, solutions, suspensions, emulsions, gels, creams, ointments, pastes, jellies, paints, powders, and aerosols.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

Cancer model organism, as used herein, is an organism exhibiting a phenotype indicative of cancer, or the activity of cancer causing elements, within the organism. The term cancer is defined above. A wide variety of organisms may serve as cancer model organisms, and include for example, cancer cells and mammalian organisms such as rodents (e.g. mouse or rat) and primates (such as humans). Cancer cell lines are widely understood by those skilled in the art as cells exhibiting phenotypes or genotypes similar to in vivo cancers. Cancer cell lines as used herein includes cell lines from animals (e.g. mice) and from humans.

An "anticancer agent" as used herein refers to a molecule (e.g. compound, peptide, protein, nucleic acid, antibody)

used to treat cancer through destruction or inhibition of cancer cells or tissues. Anticancer agents may be selective for certain cancers or certain tissues. In embodiments, anticancer agents herein may include epigenetic inhibitors and multi-kinase inhibitors.

An "epigenetic inhibitor" as used herein, refers to an inhibitor of an epigenetic process, such as DNA methylation (a DNA methylation Inhibitor) or modification of histones (a Histone Modification Inhibitor). An epigenetic inhibitor may be a histone-deacetylase (HDAC) inhibitor, a DNA methyltransferase (DNMT) inhibitor, a histone methyltransferase (HMT) inhibitor, a histone demethylase (HDM) inhibitor, or a histone acetyltransferase (HAT). Examples of HDAC inhibitors include Vorinostat, romidepsin, CI-994, Belinostat, Panobinostat, Givinostat, Entinostat, Mocetinostat, SRT501, CUDC-101, JNJ-26481585, or PCI24781. Examples of DNMT inhibitors include azacitidine and decitabine. Examples of HMT inhibitors include EPZ-5676. Examples of HDM inhibitors include pargyline and tranylcypromine. Examples of HAT inhibitors include CCT077791 and garcinol.

A "multi-kinase inhibitor" is a small molecule inhibitor of at least one protein kinase, including tyrosine protein kinases and serine/threonine kinases. A multi-kinase inhibitor may include a single kinase inhibitor. Multi-kinase inhibitors may block phosphorylation. Multi-kinases inhibitors may act as covalent modifiers of protein kinases. Multi-kinase inhibitors may bind to the kinase active site or to a secondary or tertiary site inhibiting protein kinase activity. A multi-kinase inhibitor may be an anti-cancer multi-kinase inhibitor. Exemplary anti-cancer multi-kinase inhibitors include dasatinib, sunitinib, erlotinib, bevacizumab, vatalanib, vemurafenib, vandetanib, cabozantinib, poatinib, axitinib, ruxolitinib, regorafenib, crizotinib, bosutinib, cetuximab, gefitinib, imatinib, lapatinib, lenvatinib, mubritinib, nilotinib, panitumumab, pazopanib, trastuzumab, or sorafenib.

"Selective" or "selectivity" or the like of a compound refers to the compound's ability to discriminate between molecular targets (e.g. a compound having selectivity toward HMT SUV39H1 and/or HMT G9a).

"Specific", "specifically", "specificity", or the like of a compound refers to the compound's ability to cause a particular action, such as inhibition, to a particular molecular target with minimal or no action to other proteins in the cell (e.g. a compound having specificity towards HMT SUV39H1 and/or HMT G9a displays inhibition of the activity of those HMTs whereas the same compound displays little-to-no inhibition of other HMTs such as DOT1, EZH1, EZH2, GLP, MLL1, MLL2, MLL3, MLL4, NSD2, SET1b, SET7/9, SETS, SETMAR, SMYD2, SUV39H2).

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. In embodiments inhibition means negatively affecting (e.g. decreasing) the concentration or levels of the protein relative to the concentration or level of the protein in the absence of the inhibitor. In embodiments inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g. an inhibitor binds to the target protein). In embodiments, inhibition refers to a reduction of activity of a target protein from an indirect interaction (e.g. an inhibitor binds to a protein that activates the target protein, thereby preventing target protein activation). A "ecDNA inhibitor" is a compound that negatively affects (e.g. decreases) the activity or function of ecDNA relative to the activity or function of ecDNA in the absence of the inhibitor.

The terms "inhibitor," "repressor" or "antagonist" or "downregulator" interchangeably refer to a substance capable of detectably decreasing the expression or activity of a given gene or protein. The antagonist can decrease expression or activity 10%, 20%, 30%, 40%, 50%, 60%, 70%, 80%, 90% or more in comparison to a control in the absence of the antagonist. In certain instances, expression or activity is 1.5-fold, 2-fold, 3-fold, 4-fold, 5-fold, 10-fold or lower than the expression or activity in the absence of the antagonist.

The term "RNA-guided DNA endonuclease" and the like refer, in the usual and customary sense, to an enzyme that cleave a phosphodiester bond within a DNA polynucleotide chain, wherein the recognition of the phosphodiester bond is facilitated by a separate RNA sequence (for example, a single guide RNA).

The term "Class II CRISPR endonuclease" refers to endonucleases that have similar endonuclease activity as Cas9 and participate in a Class II CRISPR system. An example Class II CRISPR system is the type II CRISPR locus from *Streptococcus pyogenes* SF370, which contains a cluster of four genes Cas9, Cas1, Cas2, and Csn1, as well as two non-coding RNA elements, tracrRNA and a characteristic array of repetitive sequences (direct repeats) interspaced by short stretches of non-repetitive sequences (spacers, about 30 bp each). The Cpf1 enzyme belongs to a putative type V CRISPR-Cas system. Both type II and type V systems are included in Class II of the CRISPR-Cas system.

A "detectable agent" or "detectable moiety" is a composition detectable by appropriate means such as spectroscopic, photochemical, biochemical, immunochemical, chemical, magnetic resonance imaging, or other physical means. For example, useful detectable agents include $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{77}$As, $^{86}$Y, $^{90}$Y, $^{89}$Sr, $^{89}$Zr, $^{94}$Tc, $^{94}$Tc, $^{99m}$Tc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154-1581}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra, $^{225}$Ac, Cr, V, Mn, Fe, Co, Ni, Cu, La, Ce, Pr, Nd, Pm, Sm, Eu, Gd, Tb, Dy, Ho, Er, Tm, Yb, Lu, $^{32}$P, fluorophore (e.g. fluorescent dyes), electron-dense reagents, enzymes (e.g., as commonly used in an ELISA), biotin, digoxigenin, paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monochrystalline iron oxide nanoparticles, monochrystalline iron oxide, nanoparticle contrast agents, liposomes or other delivery vehicles containing Gadolinium chelate ("Gd-chelate") molecules, Gadolinium, radioisotopes, radionuclides (e.g. carbon-11, nitrogen-13, oxygen-15, fluorine-18, rubidium-82), fluorodeoxyglucose (e.g. fluorine-18 labeled), any gamma ray emitting radionuclides, positron-emitting radionuclide, radiolabeled glucose, radiolabeled water, radiolabeled ammonia, biocolloids, microbubbles (e.g. including microbubble shells including albumin, galactose, lipid, and/or polymers; microbubble gas core including air, heavy gas(es), perfluorocarbon, nitrogen, octafluoropropane, perflexane lipid microsphere, perflutren, etc.), iodinated contrast agents (e.g. iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, or haptens and proteins or other entities which can be made detectable, e.g., by incorporating a radiolabel into a peptide or antibody specifically reactive with a target peptide. A detectable moiety is a monovalent detectable agent or a detectable agent capable of forming a bond with another composition. In embodiments, the detectable agent is an HA tag. In embodiments, the HA tag includes the sequence set forth by SEQ ID NO:24. In embodiments, the HA tag is the sequence set forth by SEQ ID NO:24. In embodiments, the detectable agent is blue fluorescent protein (BFP). In embodiments, the BFP includes the sequence set forth by SEQ ID NO:30. In embodiments, the BFP is the sequence set forth by SEQ ID NO:30.

Radioactive substances (e.g., radioisotopes) that may be used as imaging and/or labeling agents in accordance with the embodiments of the disclosure include, but are not limited to $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{77}$As, $^{86}$Y, $^{90}$Y, $^{89}$Sr, $^{89}$Zr, $^{94}$Tc, $^{94}$Tc, $^{99m}$Tc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154\text{-}158}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra, $^{225}$Ac. Paramagnetic ions that may be used as additional imaging agents in accordance with the embodiments of the disclosure include, but are not limited to, ions of transition and lanthanide metals (e.g. metals having atomic numbers of 21-29, 42, 43, 44, or 57-71). These metals include ions of Cr, V, Mn, Fe, Co, Ni, Cu, La, Ce, Pr, Nd, Pm, Sm, Eu, Gd, Tb, Dy, Ho, Er, Tm, Yb and Lu.

Compositions and Methods of Use

Provided herein are, inter alia, compositions and methods for diagnosing, treating and monitoring treatment of cancer. The methods provided herein include diagnosing cancer and monitoring cancer treatment by detecting and mapping amplified extrachromosomal oncogene sequences which are selectively expressed in cancer cells versus healthy cells. Further, compositions and methods are provided herein that induce apoptosis specifically in cancer cells by targeting extrachromosomal DNA present in cancer cells. The resultant DNA damage can destabilizes the extrachromosomal DNA and promotes apoptosis. The unique molecular composition and physical structure of the extrachromosomal DNA in each patient's cancer cells allows for personalized cancer treatment.

Methods of Diagnosing and Monitoring

In some embodiments, the disclosure provides methods for detecting cancer, or methods for diagnosing cancer, or methods for monitoring the progression of cancer, or methods for monitoring cancer treatment by the following steps: (i) obtaining a biological sample from a patient; (ii) detecting oncogene amplification on circular extrachromosomal DNA in the biological sample. Oncogene amplification on the circular extrachromosomal DNA in the biological sample indicates that the patient has cancer. In some embodiments, this may further involve measuring the genetic heterogeneity of the circular extrachromosomal DNA, or mapping the circular extrachromosomal DNA. In some embodiments, this may involve repeating steps (i) and (ii) to monitor changes in the oncogene amplification on the circular extrachromosomal DNA throughout the cancer treatment. Changes can be monitored by comparing the oncogene amplification to a baseline sample. In aspects, the baseline sample can be a patient (or sample population) who does not have cancer and/or a patient (or sample population) that has the same or a similar cancer. In aspects, the baseline sample can be the results of an earlier test of a patient to identify the effectiveness of cancer treatment. In some embodiments, the biological sample may be a tumor, blood, or a tumor fluid. In some embodiments, the oncogene may be EGFR, c-Myc, N-Myc, cyclin D1, ErbB2, CDK4, CDK6, BRAF, MDM2, or MDM4. In some embodiments, the oncogene is EGFR. In some embodiments, the oncogene is c-Myc. In some embodiments, the oncogene is N-Myc. In some embodiments, the oncogene is cyclin D1. In some embodiments, the oncogene is ErbB2. In some embodiments, the oncogene is CDK4. In some embodiments, the oncogene is CDK6. In some embodiments, the oncogene is BRAF. In some embodiments, the oncogene is MDM2. In some embodiments, the oncogene is MDM4.

In another aspect is provided a method of detecting an amplified extrachromosomal oncogene in a human subject in need thereof, the method including: (i) obtaining a biological sample from a human subject; (ii) detecting whether an amplified extrachromosomal oncogene is present in the sample by contacting the biological sample with an oncogene-binding agent and detecting binding between the amplified extrachromosomal oncogene and the oncogene-binding agent. In embodiments, the amplified extrachromosomal oncogene forms part of a circular extrachromosomal DNA. In embodiments, the detecting comprises detecting an intracellular location of said amplified extrachromosomal oncogene relative to a standard control. In embodiments, the detecting comprises detecting a level of said circular extrachromosomal DNA relative to a standard control. In embodiments, the detecting comprises mapping said circular extrachromosomal DNA. In embodiments, the detecting comprises detecting genetic heterogeneity of said circular extrachromosomal DNA relative to a standard control. In embodiments, the amplified extrachromosomal oncogene is EGFT, c-Myc, N-Myc, cyclin D1, ErbB2, CDK4, CDK6, BRAF, MDM2, or MDM4. In embodiments, the oncogene-binding agent is a labeled nucleic acid probe. In embodiments, the biological sample is a blood-derived biological sample, a urine-derived biological sample, a tumor sample, or a tumor fluid sample. In embodiments, the method further comprises selecting a subject that has or is at risk for developing cancer. In embodiments, the method further comprises administering to said subject an effective amount of an anti-cancer agent.

In another aspect is provided a method of detecting an amplified extrachromosomal oncogene in a cancer subject undergoing treatment for cancer, the method including: (i) obtaining a first biological sample from the cancer subject undergoing treatment for cancer; and (ii) detecting in the first biological sample a first level of an amplified extrachromosomal oncogene. In embodiments, the method further comprises, after step (ii), (iii) obtaining a second biological sample from said subject; (iv) detecting a second level of said amplified extrachromosomal oncogene; and (v) comparing said first level to said second level. In embodiments, the first biological sample from said subject is obtained at a time $t_0$, and said second biological sample from said subject is obtained at a later time $t_1$. In embodiments, the amplified extrachromosomal oncogene forms part of a circular extrachromosomal DNA. In embodiments, the detecting comprises detecting an intracellular location of said amplified extrachromosomal oncogene relative to a standard control. In embodiments, the detecting comprises detecting a level of said circular extrachromosomal DNA relative to a standard control. In embodiments, the detecting comprises mapping said circular extrachromosomal DNA. In embodiments, the detecting comprises detecting genetic heterogeneity of said circular extrachromosomal DNA relative to a standard control. In embodiments, the amplified extrachromosomal oncogene is EGFT, c-Myc, N-Myc, cyclin D1, ErbB2, CDK4, CDK6, BRAF, MDM2, or MDM4. In embodiments, the oncogene-binding agent is a labeled nucleic acid probe. In embodiments, the biological sample is a blood-derived biological sample, a urine-derived biological sample, a tumor sample, or a tumor fluid sample. In embodiments, the method further includes administering to said subject an effective amount of an anti-cancer agent.

Methods of Treatment

In an aspect, a method of treating cancer in a subject in need thereof is provided, the method including delivering to the subject a therapeutically effective amount of an extrachromosomal cancer-specific nucleic acid binding RNA and an endonuclease, thereby treating cancer in the subject.

In embodiments, the cancer includes an extrachromosomal oncogene amplification.

In another aspect is provided a method for inducing apoptosis in a cancer cell, the method including: (i) contacting a cancer cell with and effective amount of an extrachromosomal cancer-specific nucleic acid binding RNA bound to an endonuclease; (ii) allowing the extrachromosomal cancer-specific nucleic acid binding RNA to hybridize to an extrachromosomal cancer-specific nucleic acid, thereby binding the endonuclease to the extrachromosomal cancer-specific nucleic acid; and (iii) allowing the endonuclease to cleave the extrachromosomal cancer-specific nucleic acid, thereby inducing apoptosis in the cancer cell. In some embodiments, the nucleic acid encoding gRNA is transfected. In embodiments, the endonuclease is transfected. In embodiments, both the nucleic acid encoding gRNA and the endonuclease are transfected.

In some embodiments, a method of treating cancer in a patient may involve the following steps: (i) obtaining a biological sample from a patient; (ii) detecting oncogene amplification on circular extrachromosomal DNA in the biological sample; and (iii) administering a therapeutically effective amount of an anti-cancer drug to the patient to treat the cancer when oncogene amplification on the circular extrachromosomal DNA is detected in the biological sample. In some embodiments, this may further involve measuring the genetic heterogeneity of the circular extrachromosomal DNA, or mapping the circular extrachromosomal DNA. In some embodiments, this may involve repeating steps (i) and (ii) to monitor changes in the oncogene amplification on the circular extrachromosomal DNA throughout the cancer treatment. In some embodiments, the biological sample may be a tumor, blood, or a tumor fluid. In some embodiments, the oncogene may be EGFR, c-Myc, N-Myc, cyclin D1, ErbB2, CDK4, CDK6, BRAF, MDM2, or MDM4. In some embodiments, the oncogene is EGFR. In some embodiments, the oncogene is c-Myc. In some embodiments, the oncogene is N-Myc. In some embodiments, the oncogene is cyclin D1. In some embodiments, the oncogene is ErbB2. In some embodiments, the oncogene is CDK4. In some embodiments, the oncogene is CDK6. In some embodiments, the oncogene is BRAF. In some embodiments, the oncogene is MDM2. In some embodiments, the oncogene is MDM4.

In another aspect is provided a method of treating cancer in a subject in need thereof, the method including: (i) obtaining a biological sample from a human subject; (ii) detecting whether an amplified extrachromosomal oncogene is present in the sample by contacting the biological sample with an oncogene-binding agent and detecting binding between the amplified extrachromosomal oncogene and the oncogene-binding agent; and (iii) administering to the human subject an effective amount of an anti-cancer agent. In embodiments, the amplified extrachromosomal oncogene forms part of a circular extrachromosomal DNA. In embodiments, the detecting comprises detecting an intracellular location of said amplified extrachromosomal oncogene relative to a standard control. In embodiments, the detecting comprises detecting a level of said circular extrachromosomal DNA relative to a standard control. In embodiments, the detecting comprises mapping said circular extrachromosomal DNA. In embodiments, the detecting step includes detecting genetic heterogeneity of the circular extrachromosomal DNA relative to a standard control. In some embodiments, the control is a cancer cell. In some embodiments, the control is a plurality of cancer cells. In some embodiments, the control is a healthy cell. In some embodiments, the control is a plurality of healthy cells. In embodiments, the amplified extrachromosomal oncogene is EGFT, c-Myc, N-Myc, cyclin D1, ErbB2, CDK4, CDK6, BRAF, MDM2, or MDM4. In some embodiments, the oncogene is EGFR. In some embodiments, the oncogene is c-Myc. In some embodiments, the oncogene is N-Myc. In some embodiments, the oncogene is cyclin D1. In some embodiments, the oncogene is ErbB2. In some embodiments, the oncogene is CDK4. In some embodiments, the oncogene is CDK6. In some embodiments, the oncogene is BRAF. In some embodiments, the oncogene is MDM2. In some embodiments, the oncogene is MDM4. In embodiments, the oncogene-binding agent is a labeled nucleic acid probe. In embodiments, the biological sample is a blood-derived biological sample, a urine-derived biological sample, a tumor sample, or a tumor fluid sample. In embodiments, the anti-cancer agent is a peptide, small molecule, nucleic acid, antibody or aptamer.

As used herein, "treatment" or "treating," or "palliating" or "ameliorating" are used interchangeably herein. These terms refer to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made. Treatment includes preventing the disease, that is, causing the clinical symptoms of the disease not to develop by administration of a protective composition prior to the induction of the disease; suppressing the disease, that is, causing the clinical symptoms of the disease not to develop by administration of a protective composition after the inductive event but prior to the clinical appearance or reappearance of the disease; inhibiting the disease, that is, arresting the development of clinical symptoms by administration of a protective composition after their initial appearance; preventing re-occurring of the disease and/or relieving the disease, that is, causing the regression of clinical symptoms by administration of a protective composition after their initial appearance. For example, certain methods herein treat cancer (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma). For example certain methods herein treat cancer by decreasing or reducing or preventing the occurrence, growth, metastasis, or progression of cancer; or treat cancer by decreasing a symptom of cancer. Symptoms of cancer (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma) would be known or may be determined by a person of ordinary skill in the art.

As used herein the terms "treatment," "treat," or "treating" refers to a method of reducing the effects of one or more symptoms of a disease or condition characterized by expression of the protease or symptom of the disease or condition characterized by expression of the protease. Thus in the disclosed method, treatment can refer to a 10%, 20%, 30%, 40%, 50%, 60%, 70%, 80%, 90%, or 100% reduction in the severity of an established disease, condition, or symptom of the disease or condition. For example, a method for treating a disease is considered to be a treatment if there is a 10% reduction in one or more symptoms of the disease in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition. Further, as used herein, references to decreasing, reducing, or inhibiting include a change of 10%, 20%, 30%, 40%, 50%, 60%, 70%, 80%, 90% or greater as compared to a control level and such terms can include but do not necessarily include complete elimination.

An "effective amount" is an amount sufficient to accomplish a stated purpose (e.g. achieve the effect for which it is administered, treat a disease, reduce enzyme activity, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme or protein relative to the absence of the antagonist. A "function disrupting amount," as used herein, refers to the amount of antagonist required to disrupt the function of an enzyme or protein relative to the absence of the antagonist. Guidance can be found in the literature for appropriate dosages for given classes of pharmaceutical products. For example, for the given parameter, an effective amount will show an increase or decrease of at least 5%, 10%, 15%, 20%, 25%, 40%, 50%, 60%, 75%, 80%, 90%, or at least 100%. Efficacy can also be expressed as "-fold" increase or decrease. For example, a therapeutically effective amount can have at least a 1.2-fold, 1.5-fold, 2-fold, 5-fold, or more effect over a control. The exact amounts will depend on the purpose of the treatment, and will be ascertainable by one skilled in the art using known techniques (see, e.g., Lieberman, Pharmaceutical Dosage Forms (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies, for example cancer therapies such as chemotherapy, hormonal therapy, radiotherapy, or immunotherapy. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols.

Formulations suitable for oral administration can consist of (a) liquid solutions, such as an effective amount of the antibodies provided herein suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

Pharmaceutical compositions can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes). Additionally, these carriers can function as immuno stimulating agents (i.e., adjuvants).

Suitable formulations for rectal administration include, for example, suppositories, which consist of the packaged nucleic acid with a suppository base. Suitable suppository bases include natural or synthetic triglycerides or paraffin hydrocarbons. In addition, it is also possible to use gelatin rectal capsules which consist of a combination of the compound of choice with a base, including, for example, liquid triglycerides, polyethylene glycols, and paraffin hydrocarbons.

Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration, oral administration, and intravenous administration are the preferred methods of administration. The formulations of compounds can be presented in unit-dose or multi-dose sealed containers, such as ampules and vials.

Injection solutions and suspensions can be prepared from sterile powders, granules, and tablets of the kind previously described. Cells transduced by nucleic acids for ex vivo therapy can also be administered intravenously or parenterally as described above.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents.

The combined administration contemplates co-administration, using separate formulations or a single pharmaceutical formulation, and consecutive administration in either order, wherein preferably there is a time period while both (or all) active agents simultaneously exert their biological activities.

Effective doses of the compositions provided herein vary depending upon many different factors, including means of administration, target site, physiological state of the patient, whether the patient is human or an animal, other medications administered, and whether treatment is prophylactic or therapeutic. However, a person of ordinary skill in the art would immediately recognize appropriate and/or equivalent doses looking at dosages of approved compositions for treating and preventing cancer for guidance.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Compositions

In an aspect, an extrachromosomal nucleic acid protein complex is provided wherein the extrachromosomal nucleic acid protein complex includes an extrachromosomal cancer-specific nucleic acid bound to an endonuclease through a cancer-specific nucleic acid binding RNA.

The term "extrachromosomal cancer-specific nucleic acid" as used herein refers to a nucleic acid that forms part of an extrachromosomal DNA present in a cancer cell. The extrachromosomal cancer-specific nucleic acid may recombine with chromosomal DNA in a cancer cell and thereby become part of the cellular chromosome. The methods provided herein including embodiments thereof may detect extrachromosomal cancer-specific nucleic acids or amplified extrachromosomal oncogenes which originate from ecDNA, but during replication of the cancer cell become part of the cellular chromosome. In embodiments, the extrachromosomal cancer-specific nucleic acid is an oncogene. In embodiments, the extrachromosomal cancer-specific nucleic acid is an oncogene nucleic acid. In embodiments, the extrachromosomal cancer-specific nucleic acid is a non-essential gene nucleic acid. In embodiments, the extrachromosomal cancer-specific nucleic acid is an intragenic nucleic acid sequence. In embodiments, the extrachromosomal cancer-specific nucleic acid is a junction nucleic acid sequence. In embodiments, the extrachromosomal cancer-specific nucleic acid is amplified.

The term "cancer-specific nucleic acid binding RNA" refers to a polynucleotide sequence including the crRNA sequence and optionally the tracrRNA sequence. The crRNA sequence includes a guide sequence (i.e., "guide" or "spacer") and a tracr mate sequence (i.e., direct repeat(s)). The term "guide sequence" refers to the sequence that specifies the target site (i.e., extrachromosomal cancer-specific nucleic acid).

In certain embodiments, the cancer-specific nucleic acid binding RNA is a single-stranded ribonucleic acid. In certain embodiments, the cancer-specific nucleic acid binding RNA is 10, 20, 30, 40, 50, 60, 70, 80, 90, 100 or more nucleic acid residues in length. In certain embodiments, the cancer-specific nucleic acid binding RNA is from 10 to 30 nucleic acid residues in length. In certain embodiments, the cancer-specific nucleic acid binding RNA is 20 nucleic acid residues in length. In certain embodiments, the length of the pcancer-specific nucleic acid binding RNA can be at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more nucleic acid residues or sugar residues in length. In certain embodiments, the cancer-specific nucleic acid binding RNA is from 5 to 50, 10 to 50, 15 to 50, 20 to 50, 25 to 50, 30 to 50, 35 to 50, 40 to 50, 45 to 50, 5 to 75, 10 to 75, 15 to 75, 20 to 75, 25 to 75, 30 to 75, 35 to 75, 40 to 75, 45 to 75, 50 to 75, 55 to 75, 60 to 75, 65 to 75, 70 to 75, 5 to 100, 10 to 100, 15 to 100, 20 to 100, 25 to 100, 30 to 100, 35 to 100, 40 to 100, 45 to 100, 50 to 100, 55 to 100, 60 to 100, 65 to 100, 70 to 100, 75 to 100, 80 to 100, 85 to 100, 90 to 100, 95 to 100, or more residues in length. In certain embodiments, the cancer-specific nucleic acid binding RNA is from 10 to 15, 10 to 20, 10 to 30, 10 to 40, or 10 to 50 residues in length.

In certain embodiments, the cancer-specific nucleic acid binding RNA has the sequence of SEQ ID NO:1. In certain embodiments, the cancer-specific nucleic acid binding RNA has the sequence of SEQ ID NO:2. In certain embodiments, the cancer-specific nucleic acid binding RNA has the sequence of SEQ ID NO:3. In certain embodiments, the cancer-specific nucleic acid binding RNA has the sequence of SEQ ID NO:4. In certain embodiments, the cancer-specific nucleic acid binding RNA has the sequence of SEQ ID NO:5. In certain embodiments, the cancer-specific nucleic acid binding RNA has the sequence of SEQ ID NO:6. In certain embodiments, the cancer-specific nucleic acid binding RNA has the sequence of SEQ ID NO:7. In certain embodiments, the cancer-specific nucleic acid binding RNA has the sequence of SEQ ID NO:8. In certain embodiments, the cancer-specific nucleic acid binding RNA has the sequence of SEQ ID NO:9. In certain embodiments, the cancer-specific nucleic acid binding RNA has sequence of SEQ ID NO:10. In certain embodiments, the cancer-specific nucleic acid binding RNA has the sequence of SEQ ID NO:11. In certain embodiments, the cancer-specific nucleic acid binding RNA has the sequence of SEQ ID NO:12. In certain embodiments, the cancer-specific nucleic acid binding RNA has the sequence of SEQ ID NO:13. In certain embodiments, the cancer-specific nucleic acid binding RNA has the sequence of SEQ ID NO:14. In certain embodiments, the cancer-specific nucleic acid binding RNA has the sequence of SEQ ID NO:15. In certain embodiments, the cancer-specific nucleic acid binding RNA has the sequence of SEQ ID NO:16. In certain embodiments, the cancer-specific nucleic acid binding RNA has the sequence of SEQ ID NO:17. In certain embodiments, the cancer-specific nucleic acid binding RNA has the sequence of SEQ ID NO:18.

The term "non-essential gene" as used herein refers to a gene of an extrachromosomal DNA that is not an oncogene and is located in close proximity to an oncogene. The non-essential gene may be amplified during oncogene amplification. Likewise, the term "intragenic sequence" as used herein refers to a nucleic acid sequence proximal to an oncogene. The intragenic sequence may be amplified during oncogene amplification. Amplification, as used herein, refers to the presence of multiple copies of a nucleic acid sequence.

The term "junction nucleic acid sequence" refers to a nucleic acid sequence that forms part of an extrachromosomal DNA and is formed upon the circularization of the extrachromosomal DNA. Inter- and intra-chromosomal rearrangements that occur during replication of a cancer cell within extrachromosomal DNA generate unique and novel nucleic acid junction sequences. The junction nucleic acid sequence may be targeted for the insertion of DNA double strand breaks in cancer cells since the junction nucleic acid sequences are specific for cancer cells and are not present in healthy cells.

In embodiments, the endonuclease is CRISPR associated protein 9 (Cas9), CxxC finger protein 1(Cpf1), or a Class II CRISPR endonuclease.

For specific proteins described herein (e.g., Cas9, Cpf1, and the like), the named protein includes any of the protein's naturally occurring forms, or variants or homologs that maintain the protein transcription factor activity (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In other embodiments, the protein is the protein as identified by its NCBI sequence reference. In other embodiments, the protein is the protein as identified by its NCBI sequence reference or functional fragment or homolog thereof.

Thus, a "CRISPR associated protein 9," "Cas9," "Csn1" or "Cas9 protein" as referred to herein includes any of the recombinant or naturally-occurring forms of the Cas9 endonuclease or variants or homologs thereof that maintain Cas9 endonuclease enzyme activity (e.g. within at least 50%, 80%, 90%, 95%, 96%, 97%, 98%, 99% or 100% activity compared to Cas9). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Cas9 protein. In embodiments, the Cas9 protein is substantially identical to the protein identified by the UniProt reference number Q99ZW2 or a variant or homolog having substantial identity thereto. Cas9 refers to the protein also known in the art as "nickase". In embodiments, Cas9 is an RNA-guided DNA endonuclease enzyme that binds a CRISPR (clustered regularly interspaced short palindromic repeats) nucleic acid sequence. In embodiments, the CRISPR nucleic acid sequence is a prokaryotic nucleic acid sequence. In embodiments, the Cas9 nuclease from *Streptococcus pyogenes* is targeted to genomic DNA by a synthetic guide RNA consisting of a 20-nt guide sequence and a scaffold. The guide sequence base-pairs with the DNA target, directly upstream of a requisite 5'-NGG protospacer adjacent motif (PAM), and Cas9 mediates a double-stranded break (DSB) about 3-base pair upstream of the PAM. In embodiments, the CRISPR nuclease from *Streptococcus aureus* is targeted to genomic DNA by a synthetic guide RNA consisting of a 21-23-nt guide sequence and a scaffold. The guide sequence base-pairs with the DNA target, directly upstream of a requisite 5'-NNGRRT protospacer adjacent motif (PAM), and Cas9 mediates a double-stranded break (DSB) about 3-base pair upstream of the PAM.

A "Cfp1" or "Cfp1 protein" as referred to herein includes any of the recombinant or naturally-occurring forms of the Cfp1 (CxxC finger protein 1) endonuclease or variants or homologs thereof that maintain Cfp1 endonuclease enzyme activity (e.g. within at least 50%, 80%, 90%, 95%, 96%, 97%, 98%, 99% or 100% activity compared to Cfp1). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Cfp1protein. In embodiments, the Cfp1 protein is substantially identical to the protein identified by the UniProt reference number Q9POU4 or a variant or homolog having substantial identity thereto.

The term "Class II CRISPR endonuclease" refers to endonucleases that have similar endonuclease activity as Cas9 and participate in a Class II CRISPR system. An example Class II CRISPR system is the type II CRISPR locus from *Streptococcus pyogenes* SF370, which contains a cluster of four genes Cas9, Cas1, Cas2, and Csn1, as well as two non-coding RNA elements, tracrRNA and a characteristic array of repetitive sequences (direct repeats) interspaced by short stretches of non-repetitive sequences (spacers, about 30 bp each). In this system, targeted DNA double-strand break (DSB) may generated in four sequential steps. First, two non-coding RNAs, the pre-crRNA array and tracrRNA, may be transcribed from the CRISPR locus. Second, tracrRNA may hybridize to the direct repeats of pre-crRNA, which is then processed into mature crRNAs containing individual spacer sequences. Third, the mature crRNA:tracrRNA complex may direct Cas9 to the DNA target consisting of the protospacer and the corresponding PAM via heteroduplex formation between the spacer region of the crRNA and the protospacer DNA. Finally, Cas9 may mediate cleavage of target DNA upstream of PAM to create a DSB within the protospacer.

In general, a guide sequence is any polynucleotide sequence having sufficient complementarity with a target polynucleotide sequence to hybridize with the target sequence (i.e., an extrachromosomal cancer-specific nucleic acid) and direct sequence-specific binding of a CRISPR complex to the target sequence (i.e., the extrachromosomal cancer-specific nucleic acid). In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies, ELAND (Illumina, San Diego, Calif.), SOAP (available at soap.genomics.org.cn), and Maq (available at maq.sourceforge.net). In embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In embodiments, a guide sequence is less than about 75, 50, 45, 40, 35, 30, 25, 20, 15, 12, or fewer nucleotides in length. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

A guide sequence may be selected to target any extrachromosomal cancer-specific nucleic acid. A guide sequence is designed to have complementarity with an extrachromosomal cancer-specific nucleic acid. Hybridization between the extrachromosomal cancer-specific nucleic acid and the guide sequence promotes the formation of a CRISPR complex. Full complementarity is not necessarily required, provided there is sufficient complementarity to cause hybridization and promote formation of a CRISPR complex. A guide sequence (spacer) may comprise any polynucleotide, such as DNA or RNA polynucleotides.

In general, a tracr mate sequence includes any sequence that has sufficient complementarity with a tracr sequence (i.e., a tracrRNA sequence) to promote one or more of: (1) excision of a guide sequence flanked by tracr mate sequences in a cell containing the corresponding tracr sequence; and (2) formation of a CRISPR complex at an extrachromosomal cancer-specific nucleic acid, wherein the CRISPR complex comprises the tracr mate sequence hybridized to the tracr sequence. In general, degree of complementarity is with reference to the optimal alignment of the tracr mate sequence and tracr sequence, along the length of the shorter of the two sequences. Optimal alignment may be determined by any suitable alignment algorithm, and may further account for secondary structures, such as self-complementarity within either the tracr sequence or tracr mate sequence. In some embodiments, the degree of complementarity between the tracr sequence and tracr mate sequence along the length of the shorter of the two when optimally aligned is about or more than about 25%, 30%, 40%, 50%, 60%, 70%, 80%, 90%, 95%, 97.5%, 99%, or higher. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and tracr mate sequence are contained within a single transcript, such that hybridization between the two produces a transcript having a secondary structure, such as a hairpin.

Without wishing to be bound by theory, the tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of a CRISPR complex, such as by hybridization along at least a portion of the tracr sequence to all or a portion of a tracr mate sequence that is operably linked to the guide sequence. In some embodiments, the tracr sequence has sufficient complementarity to a tracr mate sequence to hybridize and participate in formation of a CRISPR complex. As with the target sequence (i.e., the extrachromosomal cancer-specific nucleic acid), it is believed that complete complementarity is not needed, provided there is sufficient to be functional. In some embodiments, the tracr sequence has at least 50%, 60%, 70%, 80%, 90%, 95% or 99% of sequence complementarity along the length of the tracr mate sequence when optimally aligned. Where the tracrRNA sequence is less than 100 (99 or less) nucleotides in length the sequence is one of 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, or 20 nucleotides in length.

In embodiments, the extrachromosomal cancer-specific nucleic acid binding RNA is at least in part complementary to the extrachromosomal cancer-specific nucleic acid.

In embodiments, the extrachromosomal nucleic acid protein complex forms part of a cell. In embodiments, the cell is a cancer cell. In embodiments, the cancer cell includes an extrachromosomal oncogene amplification.

In another aspect is provided an extrachromosomal nucleic acid protein complex including an extrachromosomal cancer-specific nucleic acid bound to an endonuclease through an extrachromosomal cancer-specific nucleic acid binding RNA. In embodiments, the extrachromosomal cancer-specific nucleic acid is an oncogene nucleic acid. In embodiments, the extrachromosomal cancer-specific nucleic acid is a non-essential gene nucleic acid. In embodiments, the extrachromosomal cancer-specific nucleic acid is an intragenic nucleic acid sequence. In embodiments, the extrachromosomal cancer-specific nucleic acid is a junction nucleic acid sequence. In embodiments, the extrachromosomal cancer-specific nucleic acid is an amplified extrachromosomal cancer-specific nucleic acid. In embodiments, the endonuclease is a CRISPR associated protein 9 (Cas9), a CxxC finger protein 1(Cpf1), or a Class II CRISPR endonuclease. In embodiments, the endonuclease is a TALEN. In embodiments, the endonuclease is a zinc finger. In embodiments, the endonuclease is a mega-nuclease. In embodiments, the extrachromosomal cancer-specific nucleic acid binding RNA is at least in part complementary to said extrachromosomal cancer-specific nucleic acid. In embodiments, the extrachromosomal nucleic acid protein complex forms part of a cell. In embodiments, the cell is a cancer cell. In embodiments, the cancer cell comprises an amplified extrachromosomal oncogene.

In another aspect is provided a method for inducing apoptosis in a cancer cell, the method including: (i) contacting a cancer cell with an effective amount of an extrachromosomal cancer-specific nucleic acid binding RNA bound to an endonuclease; (ii) allowing the extrachromosomal cancer-specific nucleic acid binding RNA to hybridize to an extrachromosomal cancer-specific nucleic acid, thereby binding the endonuclease to the extrachromosomal cancer-specific nucleic acid; and (iii) allowing the endonuclease to cleave the extrachromosomal cancer-specific nucleic acid, thereby inducing apoptosis in the cancer cell. In embodiments, the nucleic acid encoding gRNA and/or endonuclease is transfected.

EXAMPLES

Example 1: Personalized Therapy Approach for Treatment of Patients Whose Cancers have Oncogenes Amplified on ecDNA Gene amplification is one of the most frequent somatic genetic alterations in cancer and has been shown to play a key role in cancer development and progression. Genes can be amplified on extrachromosomal DNA elements (ecDNA), which Applicants have recently found to occur in close to half of cancers. The driver oncogenes that are most frequently amplified in cancer, and which form some of the most compelling targets, are found either exclusively on ecDNA or as part of a continuum being found on ecDNA and jumping on to chromosomes in abnormal locations (HSRs). Thus, oncogene amplification plays a key role in cancer pathogenesis. Currently, the treatment approaches using targeted agents have in general not benefited most patients when the oncogenes are amplified at high copy number. This stands in contrast to the relative success treating patients with targeted inhibitors for genes that contain gain of function mutations on chromosomes. New strategies are needed to treat patients whose cancers have high copy number alterations.

Applicants have developed a partially personalized, multi-tiered strategy for treating cancer patients whose tumors contain driver oncogenes amplified on ecDNA (nearly half of cancer patients). This strategy utilizes a range of different targeting strategies, including CRISPR to cause DNA double strand breaks at specific loci within the genome. Recent studies suggest that CRISPR targeting of highly amplified regions may cause more cell death because of increased DNA damage in amplified regions. Motivated by the need to develop tumor-selective treatments, Applicants are taking advantage of the unique structure of ecDNA to develop tumor-specific, personalized treatments based on the molecular composition and physical structure of ecDNA in each patient's tumor.

Multi-tiered approach: The strategy uses 3 different sets of tools:

1.) Oncogene targeting strategy: CRISPR strategies using guide RNAs that target oncogenes that are highly amplified by residing on ecDNA—Sequence specific information is used to design guides that will cause DNA double strand breaks within the oncogene. The relative sensitivity of cells that bear highly amplified genes to cell death in response to this treatment, will be used to cause tumor-selective killing. Of note, this strategy can be partially personalized, because the set of highly amplified oncogenes that are recurrently found in cancer is discrete. This approach can be used for many patients suffering from many different cancer types.

2.) Enhanced selectivity strategy: An additional opportunity resides in the relatively vulnerability of tumor cells with highly amplified sequences to undergo cell death in response to CRISPR-mediated DNA double strand breaks. Non-essential genes and intragenic sequences that are in close proximity to driver oncogenes may also be highly amplified by residing on ecDNA, thus using CRISPR strategies to cause DNA double strand breaks in these non-essential genes and intragenic DNA will also provide a compelling approach to cause selective anti-tumor efficacy. The tools we have already developed—ecDETECT plus AMPLICONARCHITECT will facilitate design of these CRISPR strategies in a "partially" personalized fashion.

3.) Highly personalized selective strategy—the circularization of ecDNA, as well as inter and intra-chromosomal rearrangements within the ecDNA, generate unique and novel junctions as targets for highly personalized CRISPR attack. Using guide RNAs designed to cause DNA double strand breaks specifically targeting these junctions, which don't exist in normal cells, coupled with the sensitivity of tumors to CRISPR-induced DNA double strand breaks in highly amplified regions, this strategy leads to a highly specific, highly personalized cancer treatment approach. Further, this approach leverages the ecDETECT and AMPLICONARCHITECT tools which Applicants have developed, to facilitate their design.

Applicants envision a path forward in which every cancer patient's tumor undergoes sequencing (as is currently becoming standard of care). Applicant's suite of diagnostic tools would be added on top, first by making tumor cell metaphases, then applying ecDETECT to determine the presence of ecDNA and quantify it, coupled with FISH-based confirmation of oncogenes on ecDNA. Following this, AMPLICONArchitect-based analysis would permit the design of the CRISPR strategies, leading to personalized cancer treatment.

Example 2: Managing Cancer Therapy Using Extrachromosomal DNA

The Unmet Medical Need: Human cells have 23 pairs of chromosomes, but in cancer, genes can be amplified in chromosomes or in circular extrachromosomal DNA (ecDNA) particles. The existence of circular extrachromosomal DNA has been known about for over 30 years, but it was thought to be a very rare event (approximately 1.4% of cancers) of unknown functional significance. In a 2014 paper in Science magazine, it was shown that the circular extrachromosomal oncogene amplification plays a role in targeted therapy resistance (Nathanson et al., Science, 2014). Oncogene amplification is one of the most frequent somatic genetic alterations in cancer and has been shown to play a key role in cancer development and progression. It was discovered that the most common genetic drivers of cancer, amplified oncogenes, which are also compelling targets for drug development, are not found on their native chromosomal locus as they are shown to be on the maps produced by The Cancer Genome Atlas (TCGA) or International Genome Consortium (ICGC), but rather, on circular extrachromosomal DNA (Turner et al., Nature, 2017). This is not simply a curious manifestation of tumor genome instability, but rather a crucial mechanism that allows tumors to develop, diversify and resist treatment.

Surprisingly, the inventors discovered that: 1) all of 17 different cancer types studied displayed evidence of having oncogene amplification on extrachromosomal DNA; 2) nearly half of human cancers possess amplified oncogenes on circular extrachromosomal DNA and 3) most commonly amplified oncogenes are found on circular extrachromosomal DNA (Turner et al., Nature, 2017); 4) oncogenes that are amplified on circular extrachromosomal DNA can relocate to aberrant chromosomal regions, demonstrating a critical role for circular extrachromosomal DNA in oncogene amplification across the genome and 5) because of its inheritance through random selection, extrachromosomal DNA dramatically elevates oncogene copy number and drives intratumoral genetic heterogeneity, potently accelerating tumor evolution Based on these discoveries, the inventors concluded: Current pathology diagnostic approaches cannot resolve the sub-nuclear location of amplified driver oncogenes in tumor cells or quantify it. In the early days of cancer diagnostics, tumors were examined by looking at chromosomes in metaphase spreads with FISH probes, which provided the ability to look at a discrete number of genes. More powerful technology moving from array based approaches to next generation sequencing facilitated detection of driver oncogene copy number alterations and mutations, but at the cost of spatial resolution. The sub-nuclear localization of many amplified driver oncogenes is assumed to be on their native chromosomal locus based on Cancer Genome Atlas maps created upon known locations within a normal human cell. This turns out to be an erroneous assumption. Because the inventors have demonstrated that oncogene amplification on ecDNA promotes resistance to a variety of therapies, the Inventors have discovered that the ability to detect ecDNA in patients, quantify it, provide a direct measure of its heterogeneity within a tumor sample, and map its contents, will help guide new treatments to patients most likely to benefit. Inventors now report that they have developed a highly quantitative method for ecDNA detection, mapping and quantification from clinical tumor samples, that can be used as a new diagnostic tool to guide cancer therapy.

Quantitative detection and mapping of extrachromosomal DNA in clinical cancer samples be used to: a. Detect, quantify and map the contents of ecDNA at baseline in tumor samples and provide a measure of intratumoral genetic heterogeneity; b. Guide treatment decisions for targeted therapies directed against oncogenes amplified on ecDNA, including EGFR, c-Myc, N-Myc, cyclin D1, ErbB2, CDK4, CDK6, BRAF, MDM2, MDM4, among others; c. Guide cytotoxic chemotherapies that have differential efficacy for patients whose tumors have ecDNA; and d. Monitor changes in ecDNA in response to treatments.

The method and process for Quantitative Detection and Mapping involves 4 steps: Step 1. "Low coverage" next generation sequencing to detect amplified oncogenes; Step 2. Making of tumor metaphases from live tumor samples from tumor biopsies, blood or tumor fluids, coupled with FISH based analysis of oncogenes; Step 3. ecDETECT analysis of metaphases to quantify ecDNA levels and to produce plots that accurately measure ecDNA heterogeneity; and Step 4. Amplicon architect analysis of NGS data to map ecDNA fine structure.

The inventors envision a path forward in which every cancer patient's tumor undergoes this 4-step diagnostic process to guide cancer treatment.

Example 3: Extrachromosomal Oncogene Amplification Drives Tumor Evolution and Genetic Heterogeneity Human cells have twenty-three pairs of chromosomes but in cancer, genes can be amplified in chromosomes or in circular extrachromosomal DNA (ECDNA), whose frequency and functional significance are not understood[1-4]. We performed whole genome sequencing, structural modeling and cytogenetic analyses of 17 different cancer types, including 2572 metaphases, and developed ECdetect to conduct unbiased integrated ECDNA detection and analysis. ECDNA was found in nearly half of human cancers varying by tumor type, but almost never in normal cells. Driver oncogenes were amplified most commonly on ECDNA, elevating transcript level. Mathematical modeling predicted that ECDNA amplification elevates oncogene copy number and increases intratumoral heterogeneity more effectively than chromosomal amplification, which we validated by quantitative analyses of cancer samples. These results suggest that ECDNA contributes to accelerated evolution in cancer.

Cancers evolve in rapidly changing environments from single cells into genetically heterogeneous masses. Darwinian evolution selects for those cells better fit to their environment. Heterogeneity provides a pool of mutations upon which selection can act[1,5-9]. Cells that acquire fitness-enhancing mutations are more likely to pass these mutations on to daughter cells, driving neoplastic progression and therapeutic resistance[10,11]. One common type of cancer mutation, oncogene amplification, can be found either in chromosomes or nuclear ECDNA elements, including double minutes (DMs)[2-4,12-14]. Relative to chromosomal amplicons, ECDNA is less stable, segregating unequally to daughter cells[18,16]. DMs are reported to occur in 1.4% of cancers with a maximum of 31.7% in neuroblastoma, based on the Mitelman database[4,17]. However, the scope of ECDNA in cancer has not been accurately quantified, the oncogenes contained therein have not been systematically examined, and the impact of ECDNA on tumor evolution has yet to be determined.

Figures 12A, 12B, 12C:
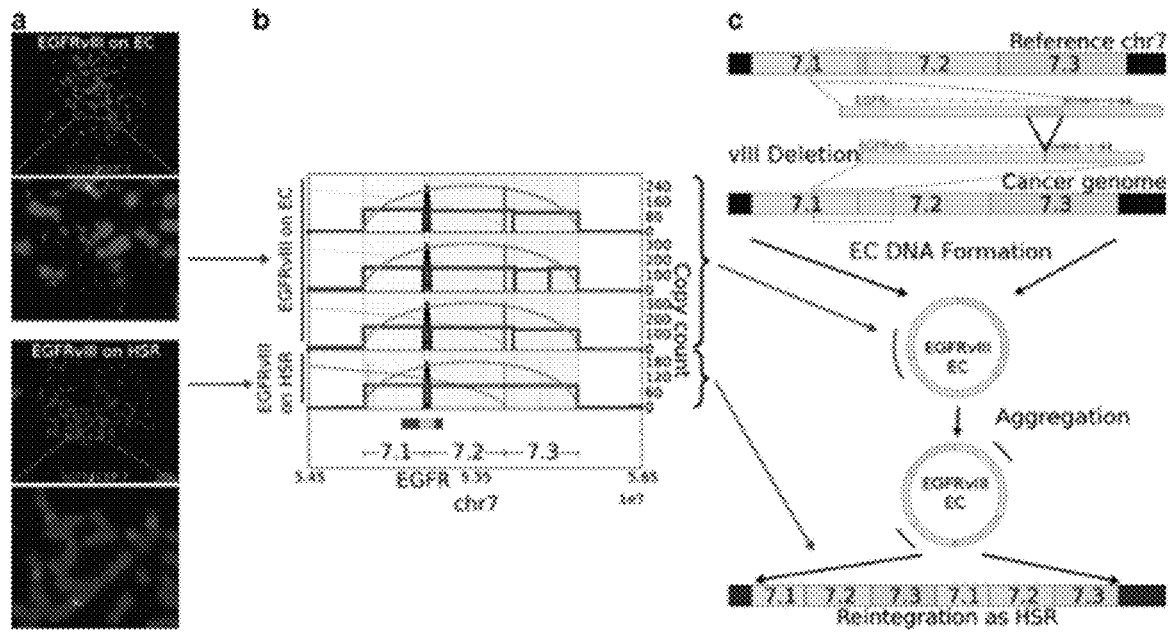
FIGS. 12A-12C. The figures show fine structure analysis of EGFRvIII Amplification in Extrachromosomal or Chromosomal DNA in GBM39 Cells.

DNA sequencing permits unbiased analysis of cancer genomes, but it cannot spatially resolve amplicons to specific chromosomal or EC regions. Bioinformatic analyses can potentially infer DNA circularity[18], but EC amplicons may vary from cell to cell. Consequently, ECDNA oncogene amplification may be greatly underestimated. Cytogenetic analysis of tumor cell metaphases can localize amplicons, but this technique does not permit unbiased discovery. To quantify the spectrum of ECDNA in human cancer and systematically interrogate its contents, we integrated whole genome sequencing (WGS) of 117 cancer cell lines, patient-derived tumor cell cultures and tumor tissues from a range of cancer types (FIG. 12A), with bioinformatic and cytogenetic analysis of 2049 metaphases from 72 cancer cell samples for which metaphases could be obtained. Additionally, 290 metaphases from 10 immortalized cell cultures, and 233 metaphases from 8 normal tissue cultures were analyzed, for a total of 2572 metaphases (Methods).

Figure 1A:
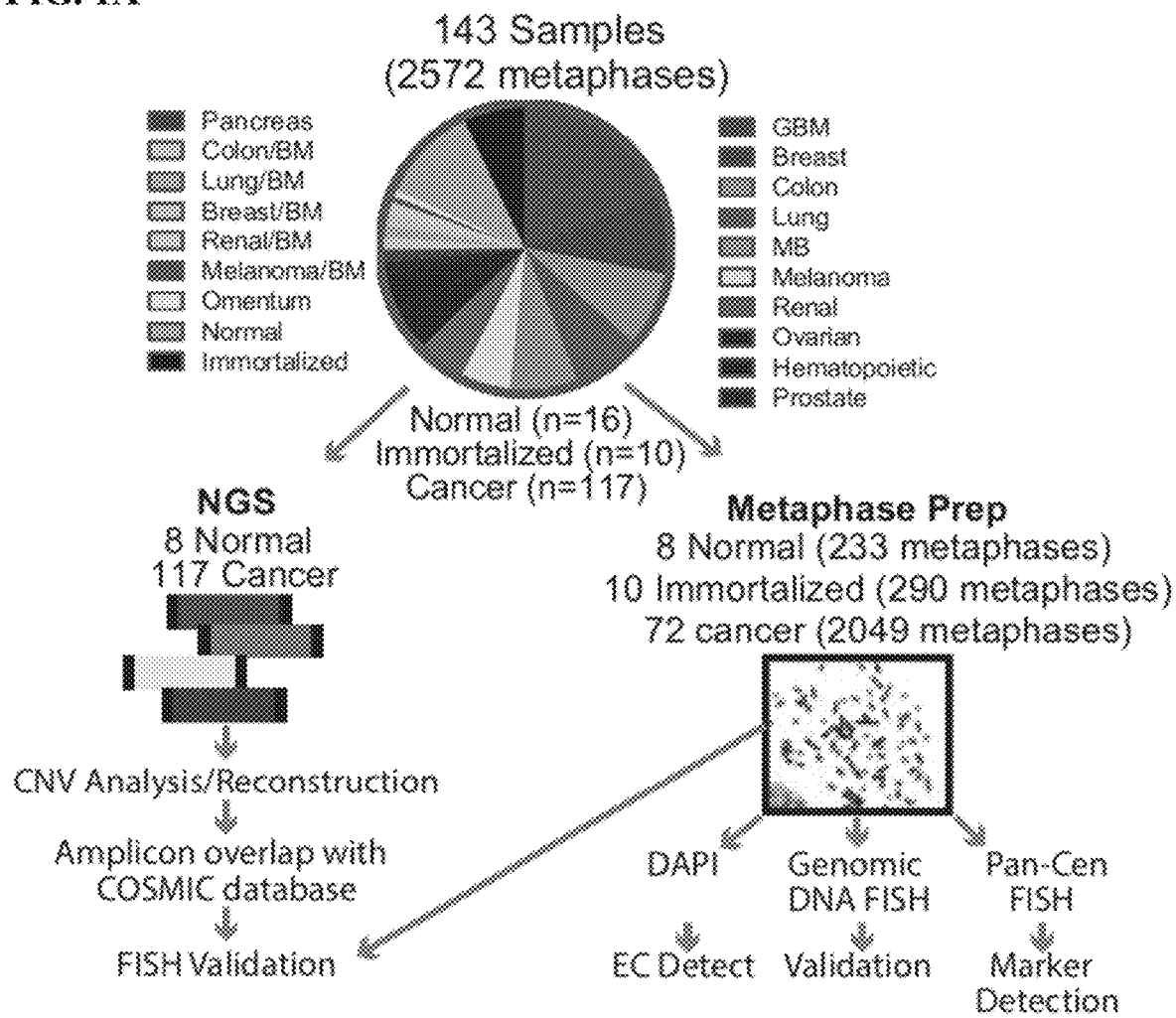
FIGS. 1A-1F. The figures show integrated next-generation DNA sequencing and cytogenetic analysis of ECDNA.
Figure 1B:
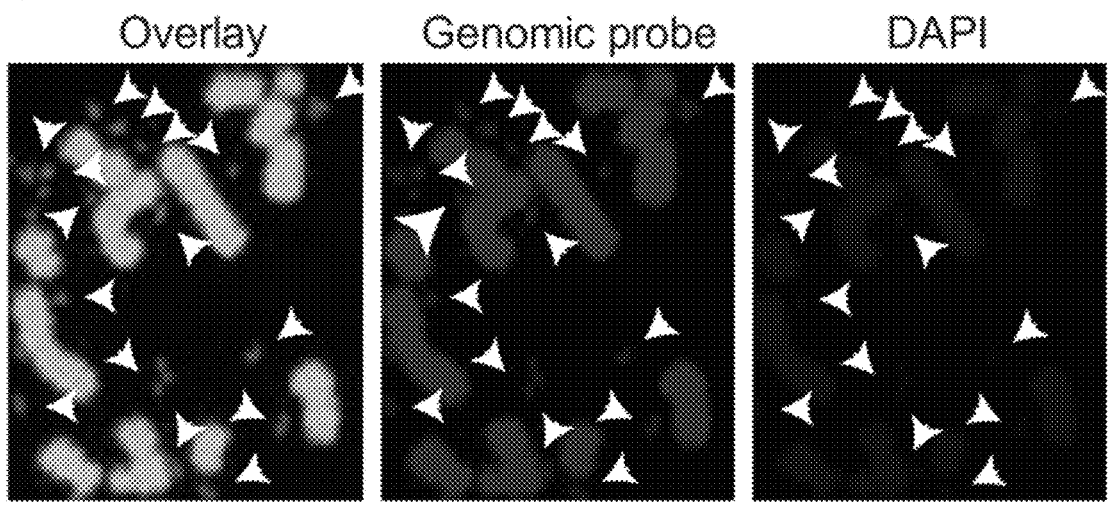
Figure 1C:
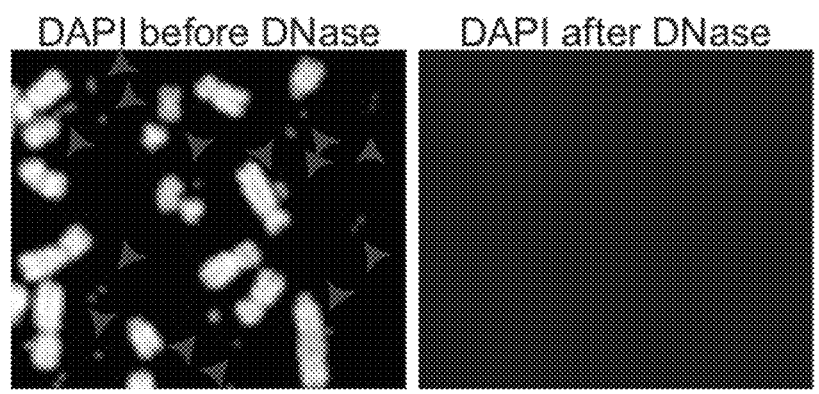
Figure 1D:
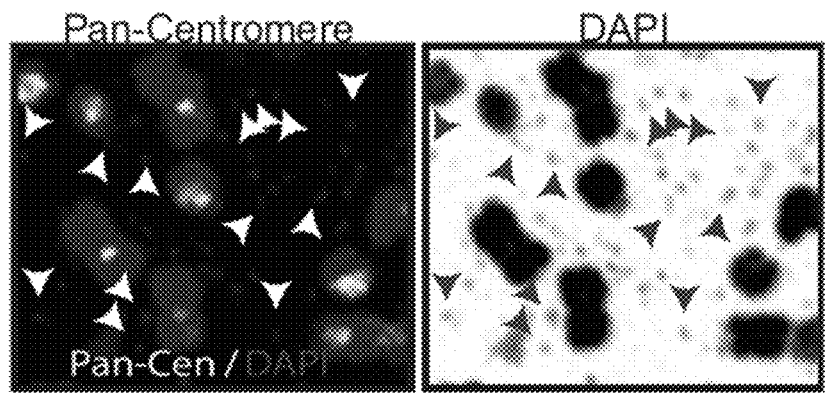
Figure 1E:
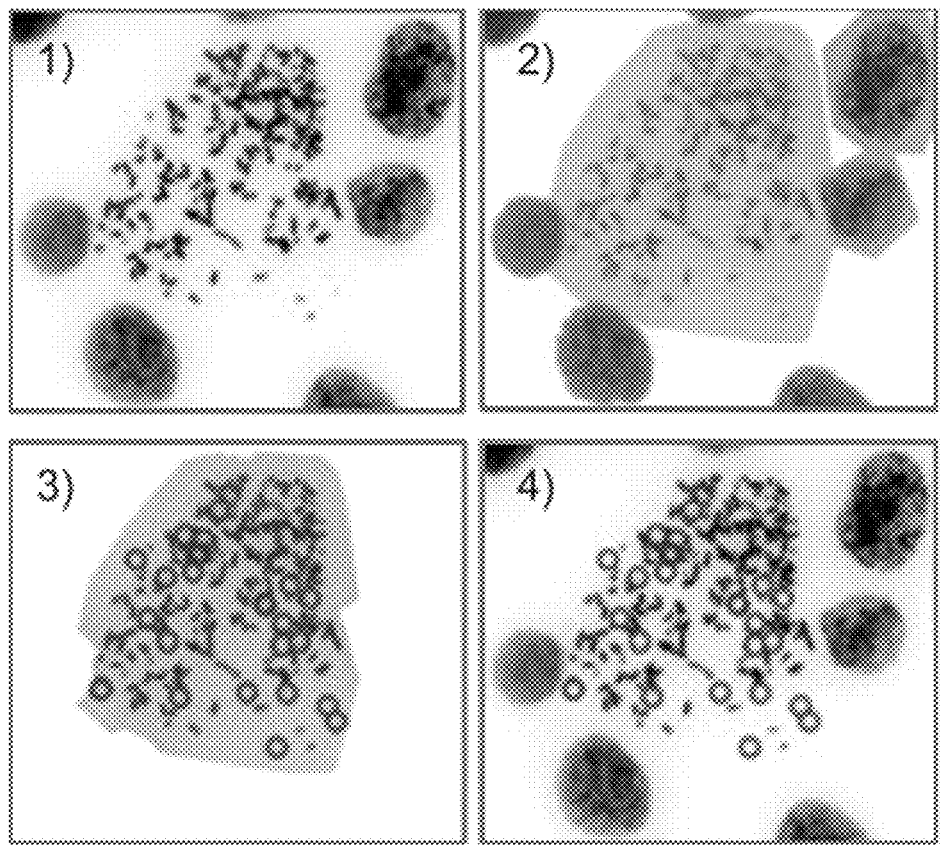
Figure 5A:
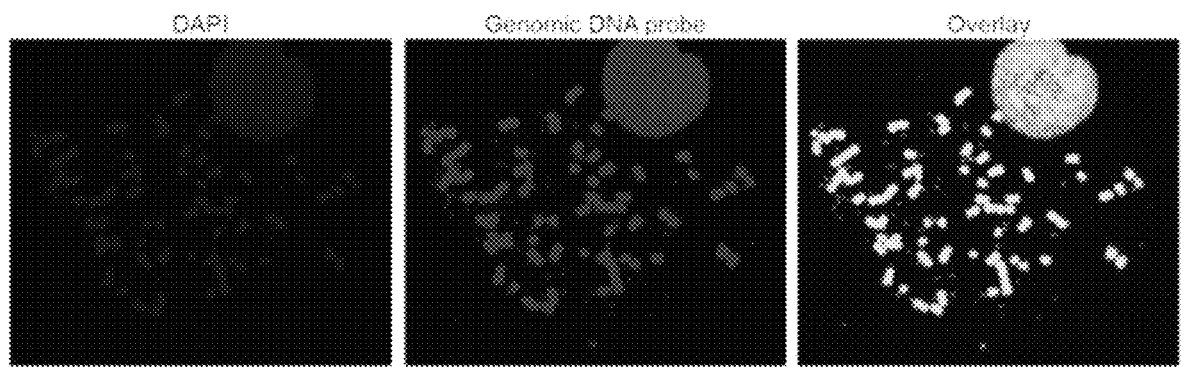
FIGS. 5A-5C. The figures show full metaphase spreads corresponding to the partial metaphase spreads shown in FIG. 1.
Figure 5B:
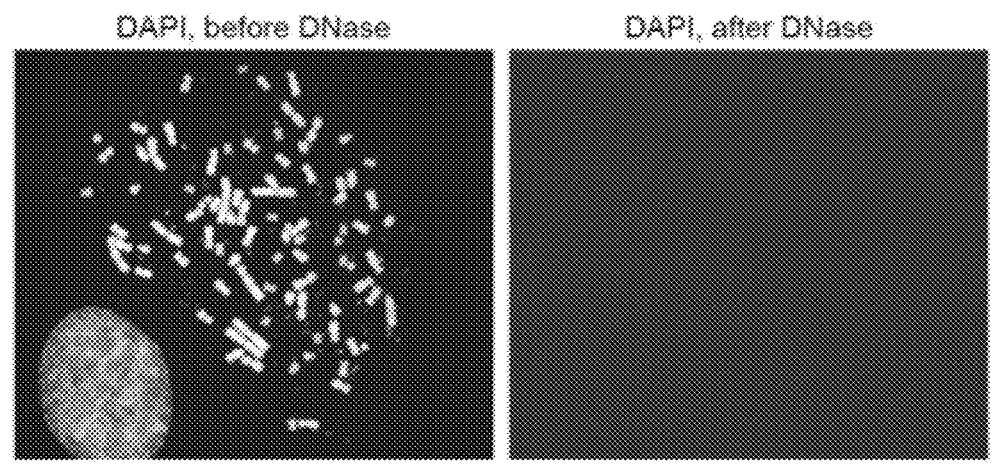
Figure 5C:
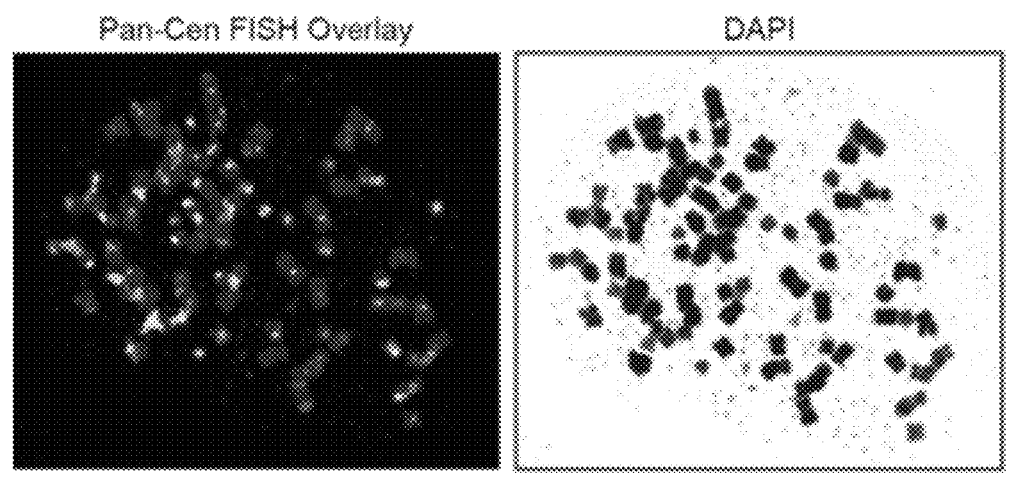

The fluorescent dye DAPI, 4', 6-diamidino-2-phenylindole, permits ECDNA detection (FIG. 1B), as confirmed using genomic DNA and centromeric FISH probes (FIG. 1B-1D; FIG. 5). We developed an image analysis software package ECdetect (FIG. 1E; Methods), providing a robust, reproducible and highly accurate method for quantifying ECDNA from DAPI-stained metaphases in an unbiased, semi-automated fashion. ECdetect accurately detected ECDNA and was highly correlated with visual detection (r=0.98, p<$2.2×10^{-16}$, FIG. 1F), permitting quantification in 2572 metaphases, including at least 20 metaphases from each sample.

Figure 2A:
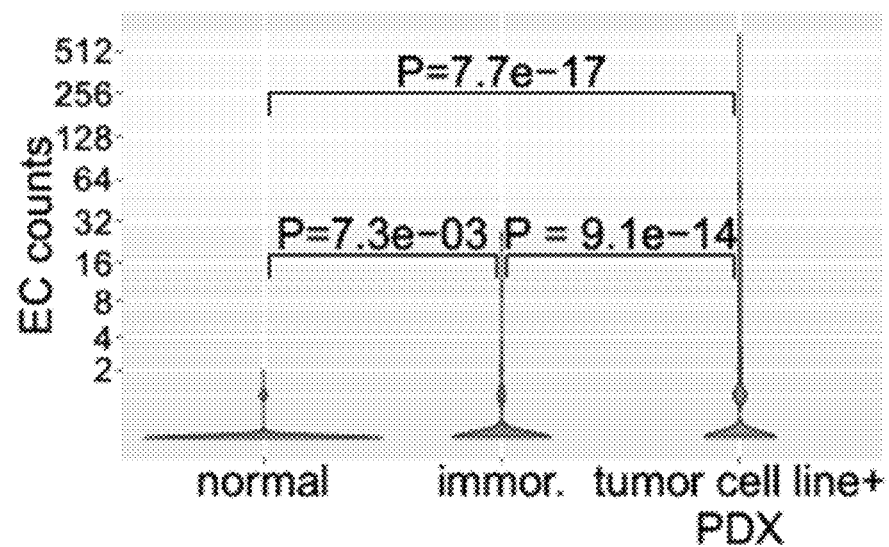
FIGS. 2A-2G. The figures show ECDNA is found in nearly half of cancers and contributes to intra-tumoral heterogeneity.
Figure 2B:
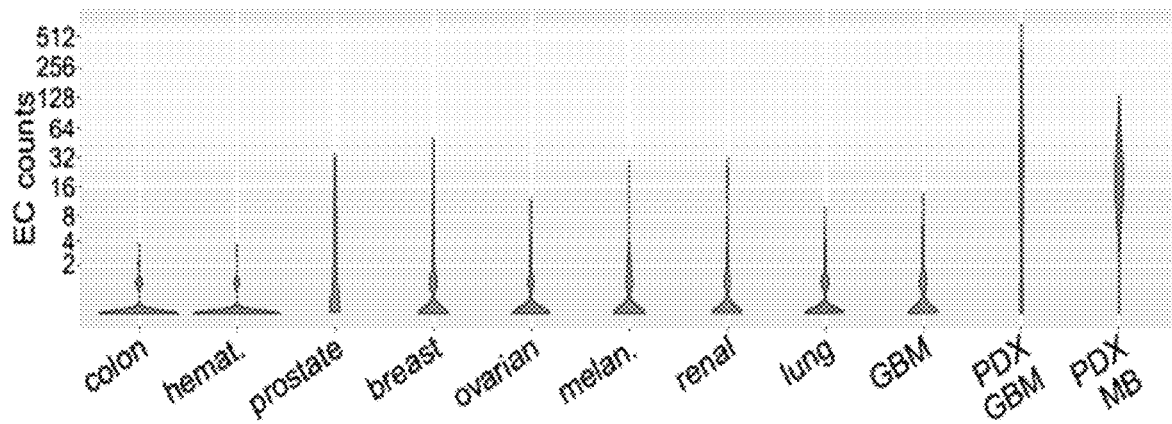
Figure 2C:
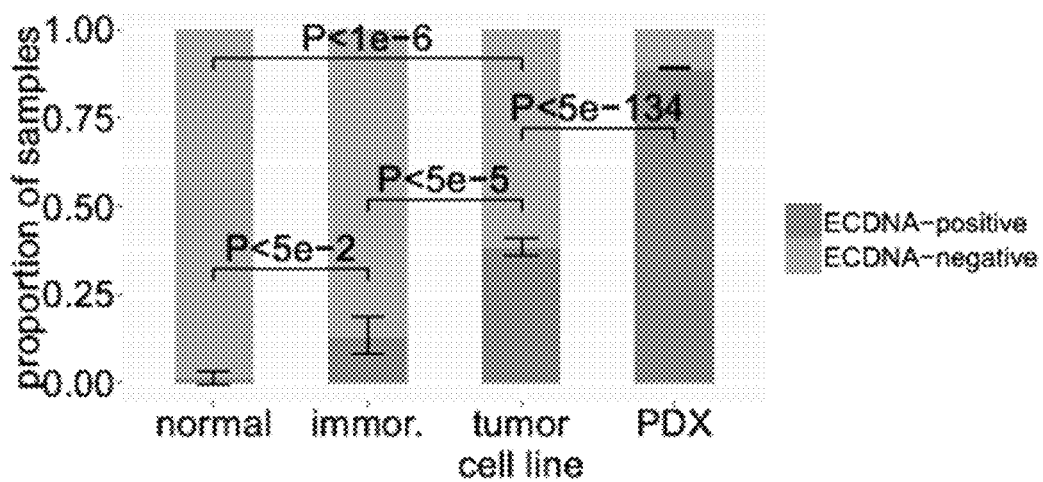
Figure 2D:
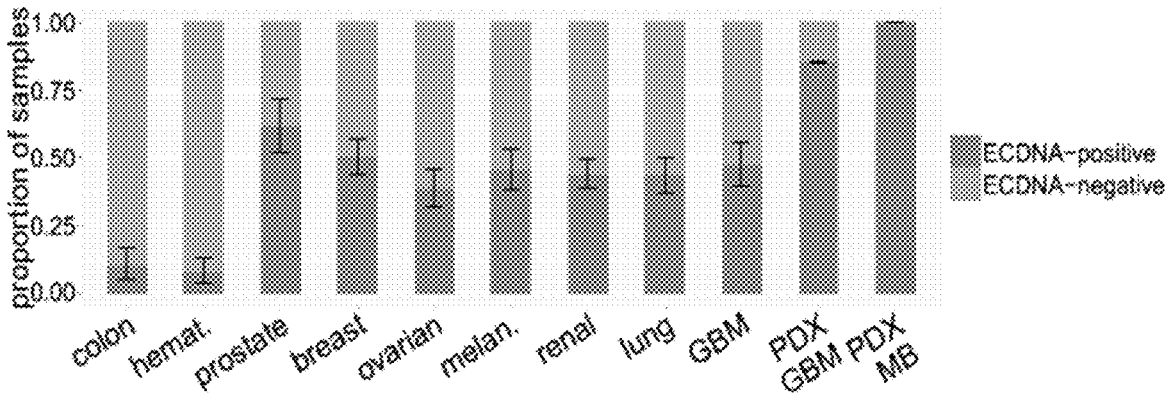
Figure 2E:
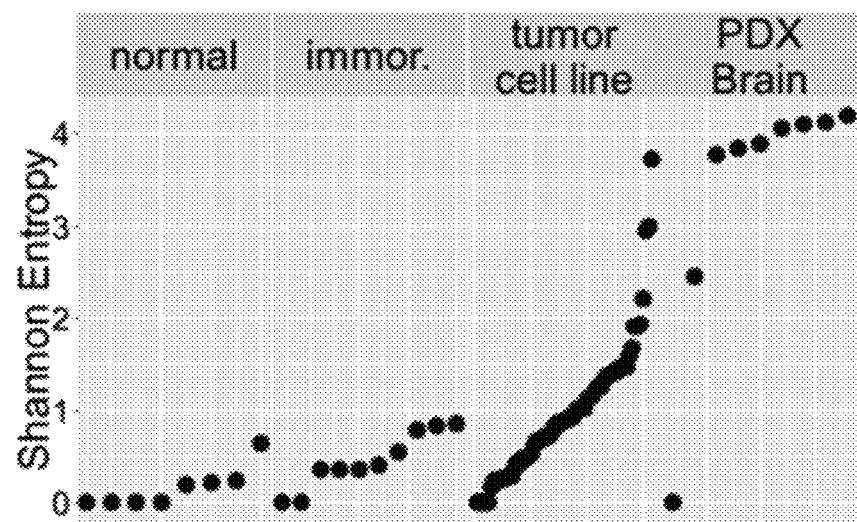
Figure 2F:
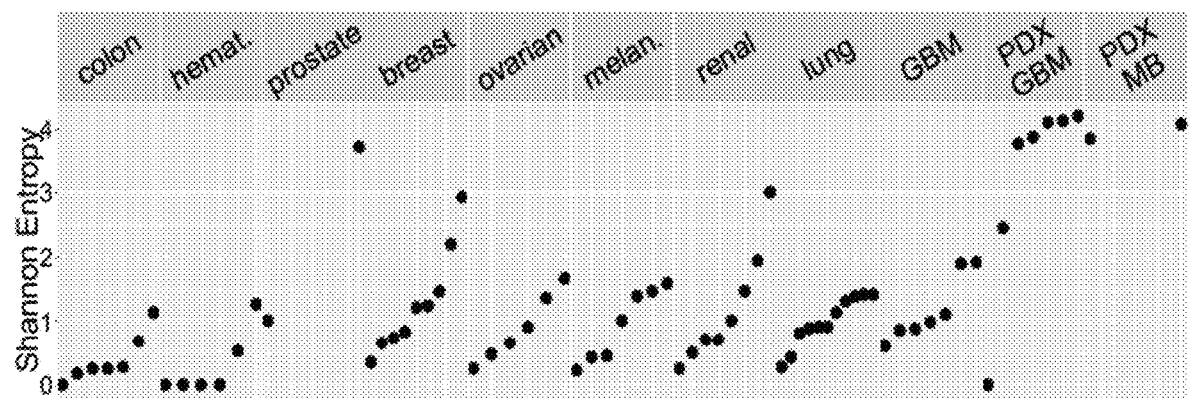
Figure 2G:
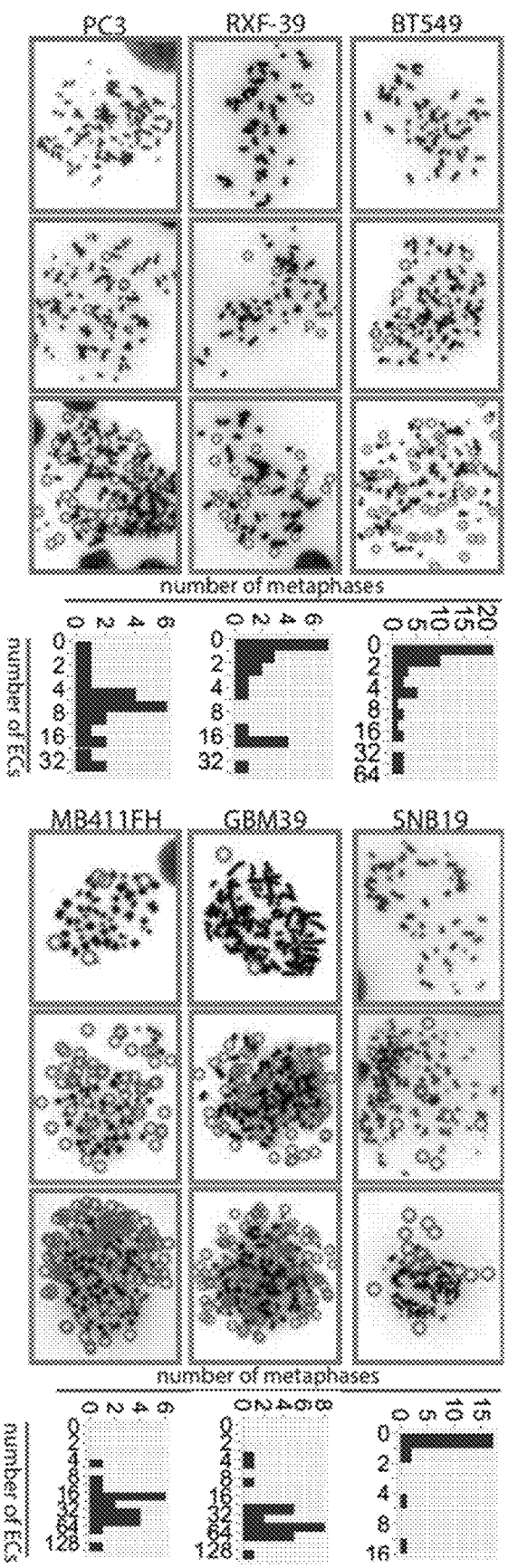
Figure 6:
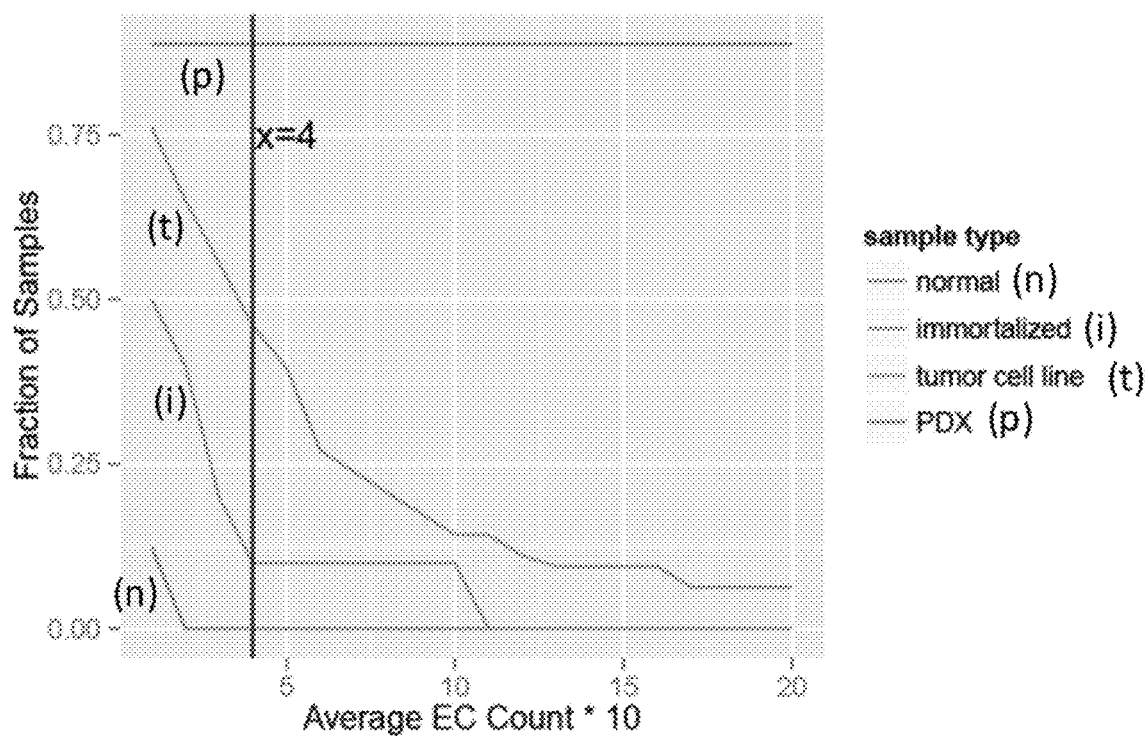
FIG. 6. The figure shows alternative analysis of ECDNA presence according to varying criteria, stratified by sample type: Samples with a minimum number of ECDNA per 10 metaphases in average shown in x-axis are classified ECDNA-positive, and their fraction is displayed on the y-axis. The vertical line at x=4 shows that for a minimum of 4 ECDNA per 10 metaphases on average, 0% of normal, 10% of immortalized, 46% of tumor cell line and 89% of PDX samples are classified as ECDNA positive.
Figure 7:
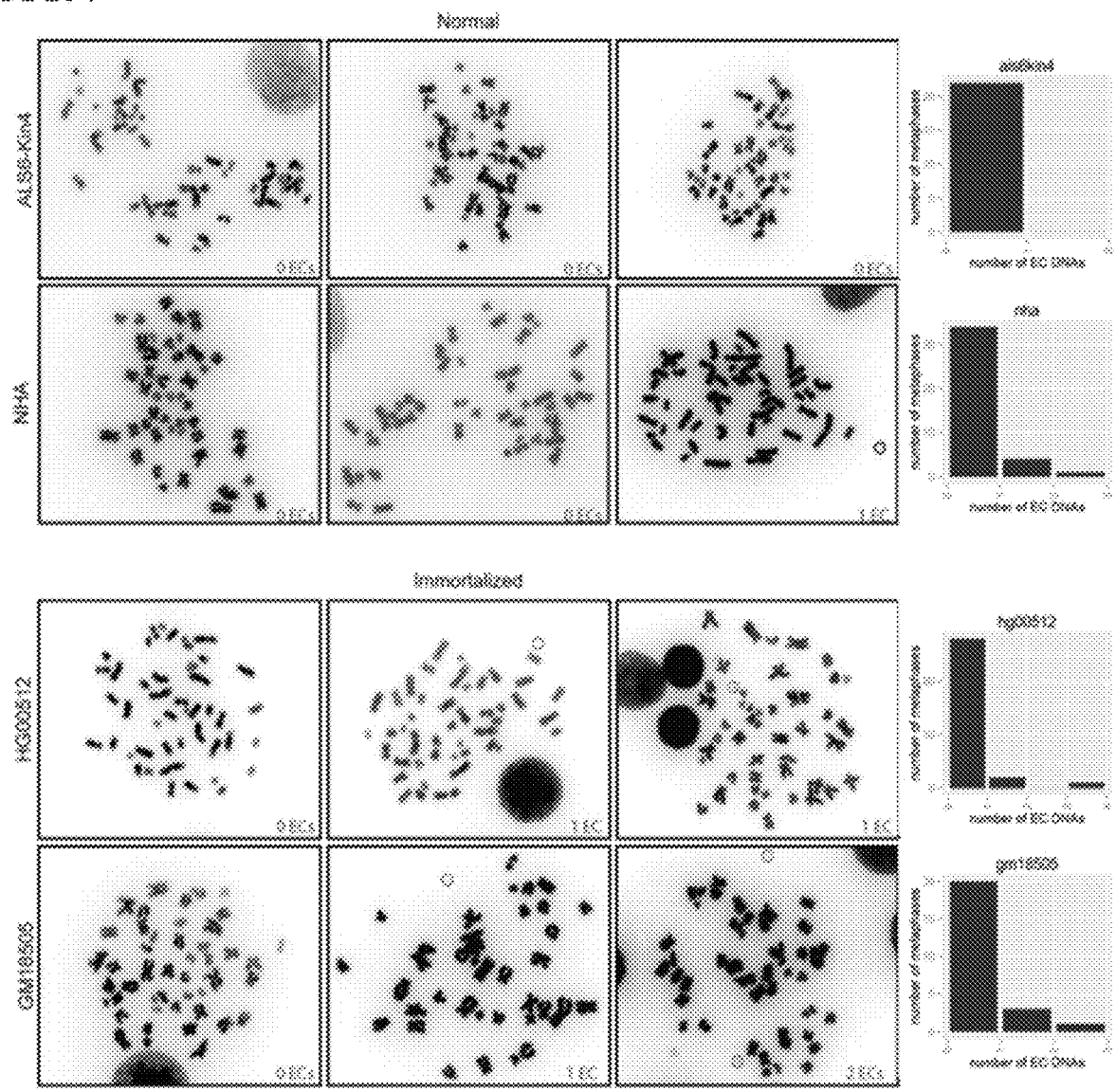
FIG. 7. The figure shows ECDNA counts in normal and immortalized cells.

ECDNA was abundant in the cancer samples (FIG. 2A), but was rarely found in normal cells. Approximately 30% of the ECDNAs were paired DMs. ECDNA levels varied among tumor types, with substantially higher levels in patient-derived cultures (FIG. 2B). Using the conservative metric of at least 2 ECDNAs in ≥10% (2 of 20) metaphases, ECDNA was detected in nearly 40% of tumor cell lines and nearly 90% of patient-derived brain tumor models (FIG. 2C-2D; Methods; FIG. 6). No significant associations between ECDNA level and either: a) primary vs. metastatic status; b) untreated vs. treated samples or c) un-irradiated vs. post-irradiated tumors were detected. The diverse array of treatments relative to sample size limited our ability to definitively determine the impact of specific therapies on ECDNA levels. ECDNA number varied greatly from cell to cell within a tumor culture (FIG. 2E-2G; FIG. 7; Supplementary Section 2.3), as quantified by the Shannon Index[19]. These data demonstrate that ECDNA is common in cancer, varies greatly from cell to cell, and is very rare in normal tissue.

Figure 3A:
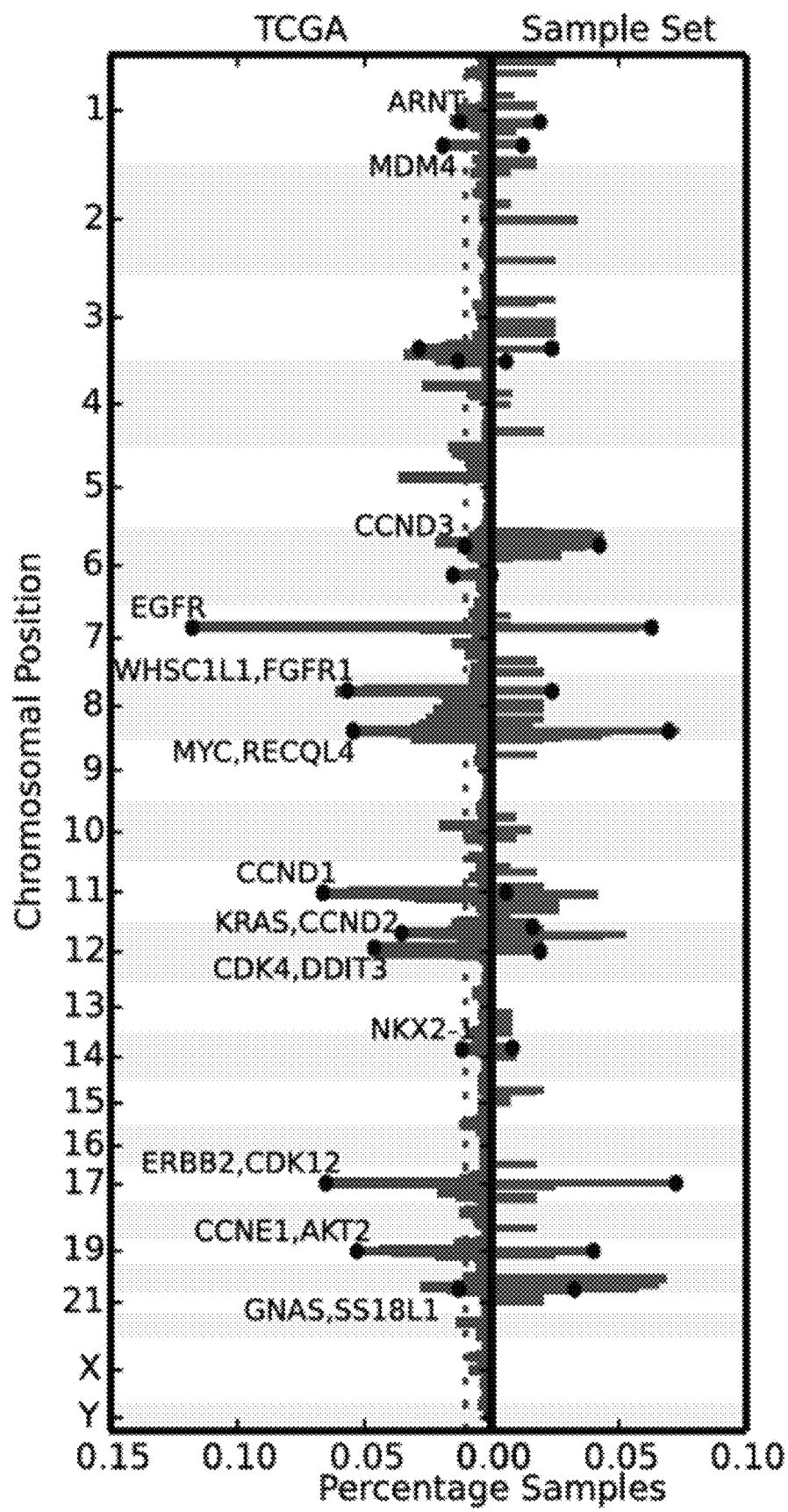
FIGS. 3A-3D. The figures show the most common focal amplifications in cancer are contained on ECDNA.
Figure 3B:
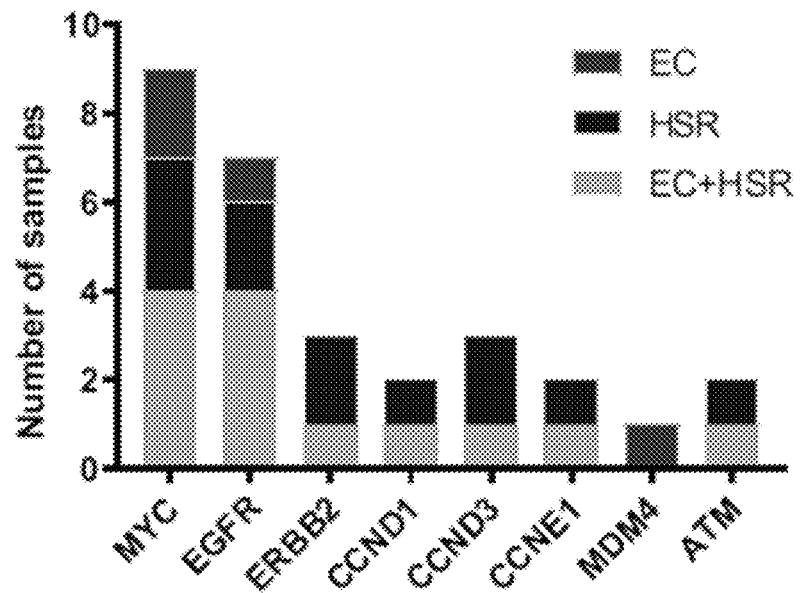
Figure 3C:
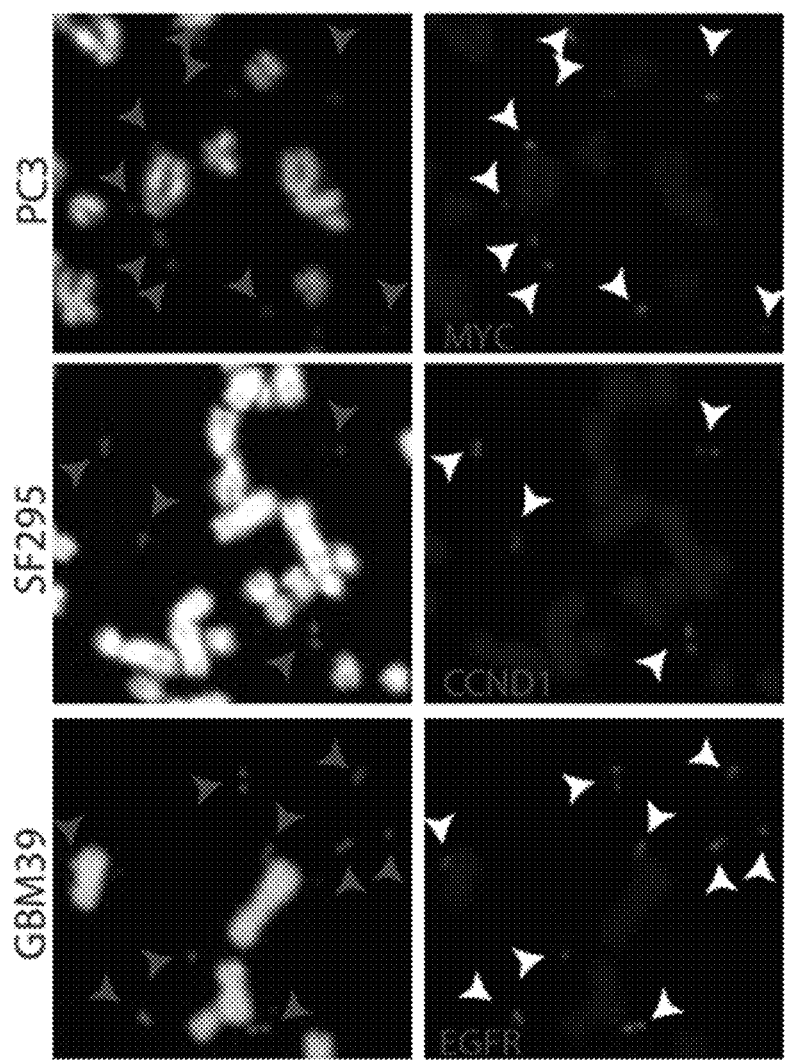
Figure 3D:
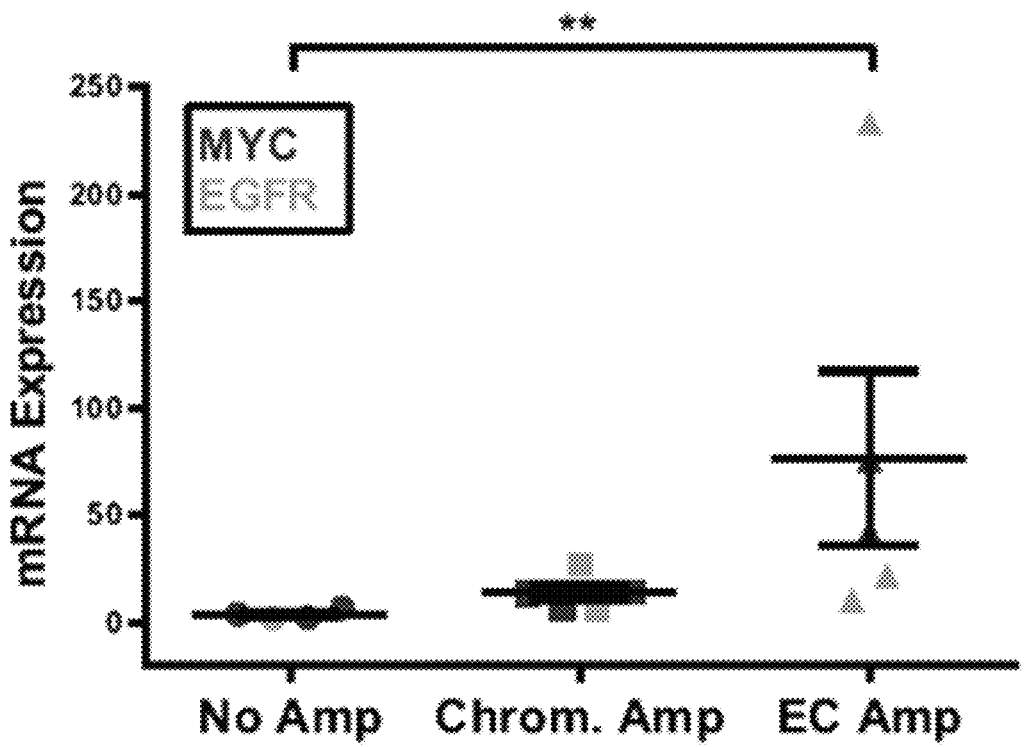
Figure 8:
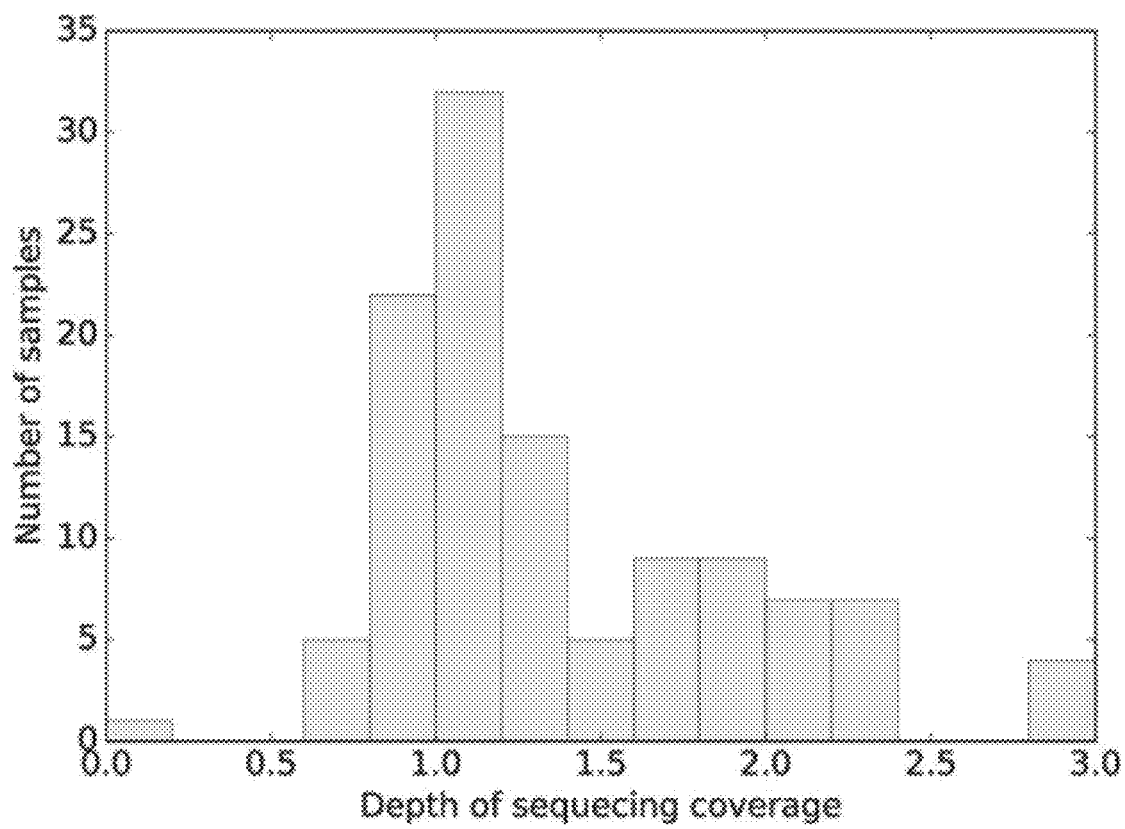
FIG. 8. The figure shows histogram of depth of coverage for next-generation sequencing of tumor samples. We sequenced 117 tumor samples including 63 cell lines, 19 neurospheres (PDX) and 35 cancer tissues with coverage ranging from 0.6× to 3.89× (excluding one sample with 0.06×coverage) with median coverage of 1.19×.
Figure 9:
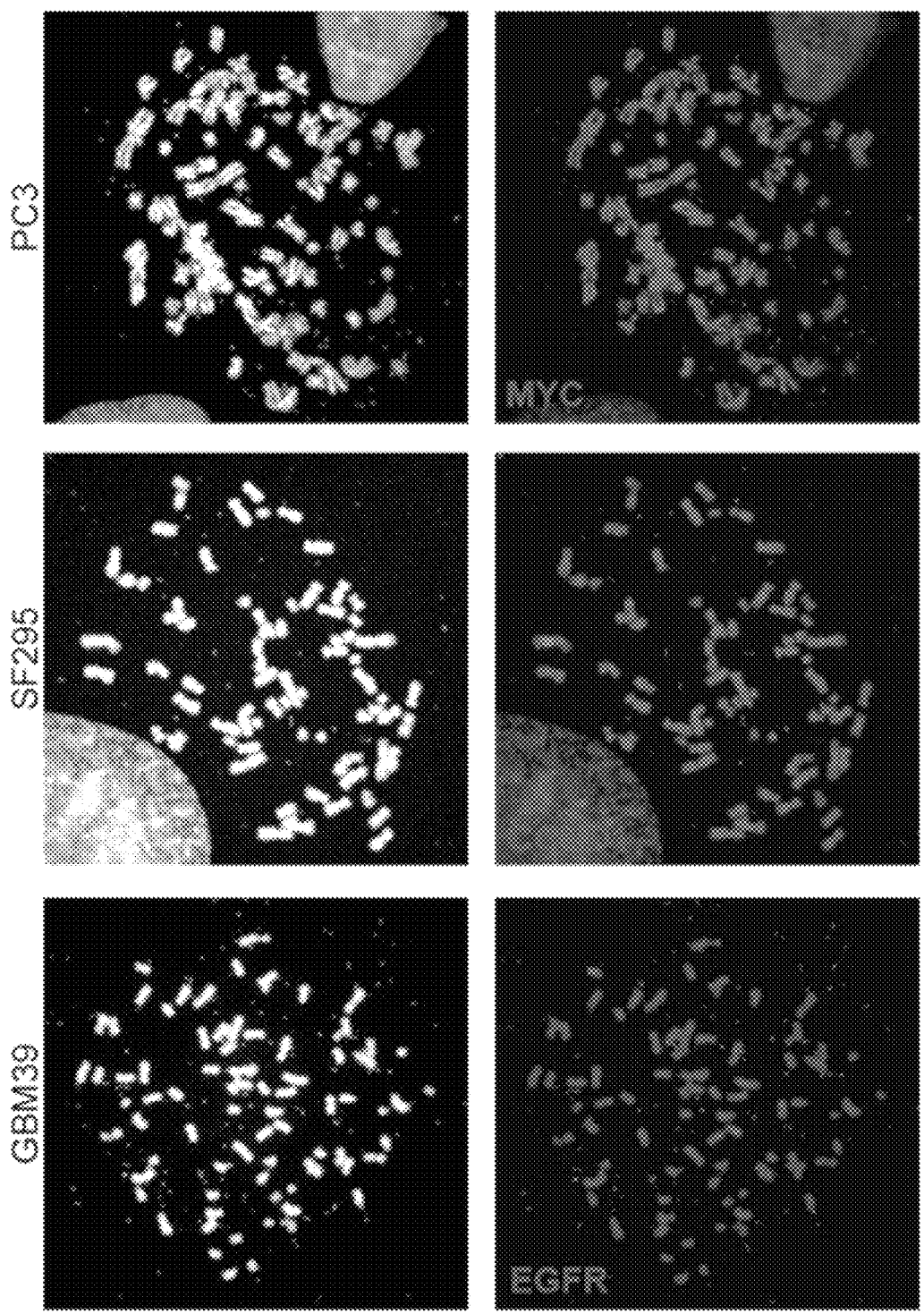
FIG. 9. The figure shows full metaphase spreads corresponding to the partial metaphase spreads shown in FIG. 14C.
Figure 10:
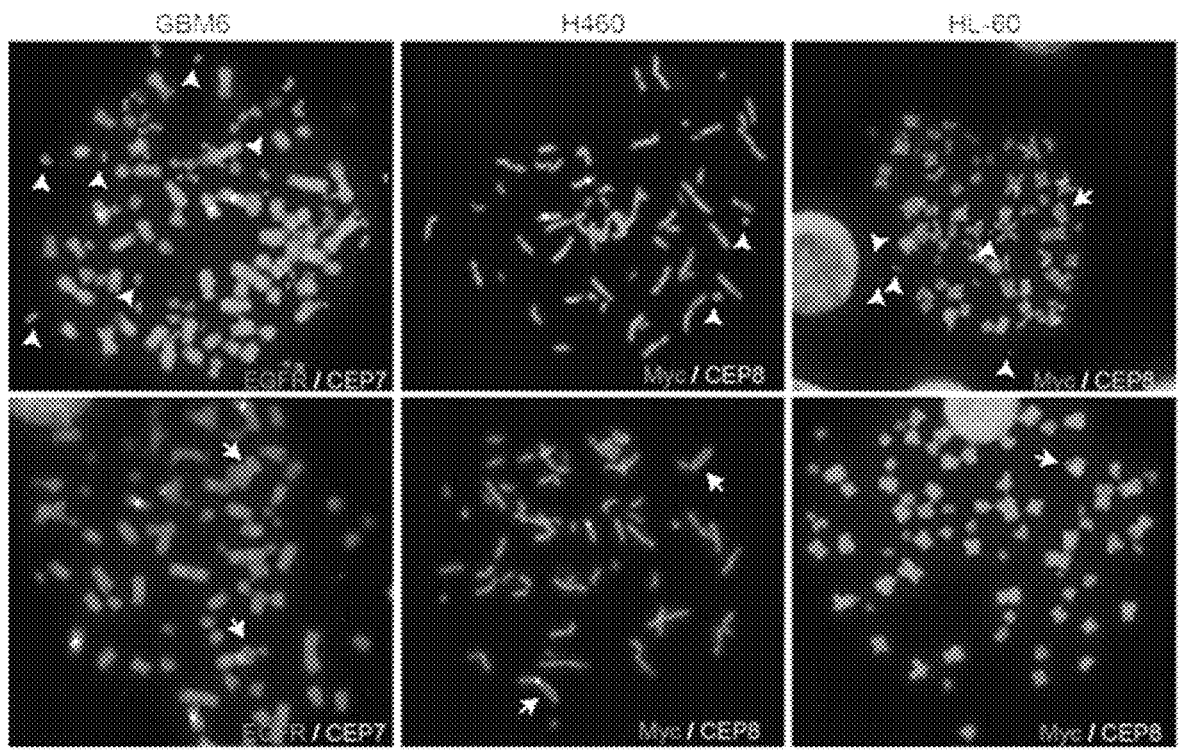
FIG. 10. The figure shows FISH images displaying both ECDNAs and HSRs in cells from the same sample.
Figure 11:
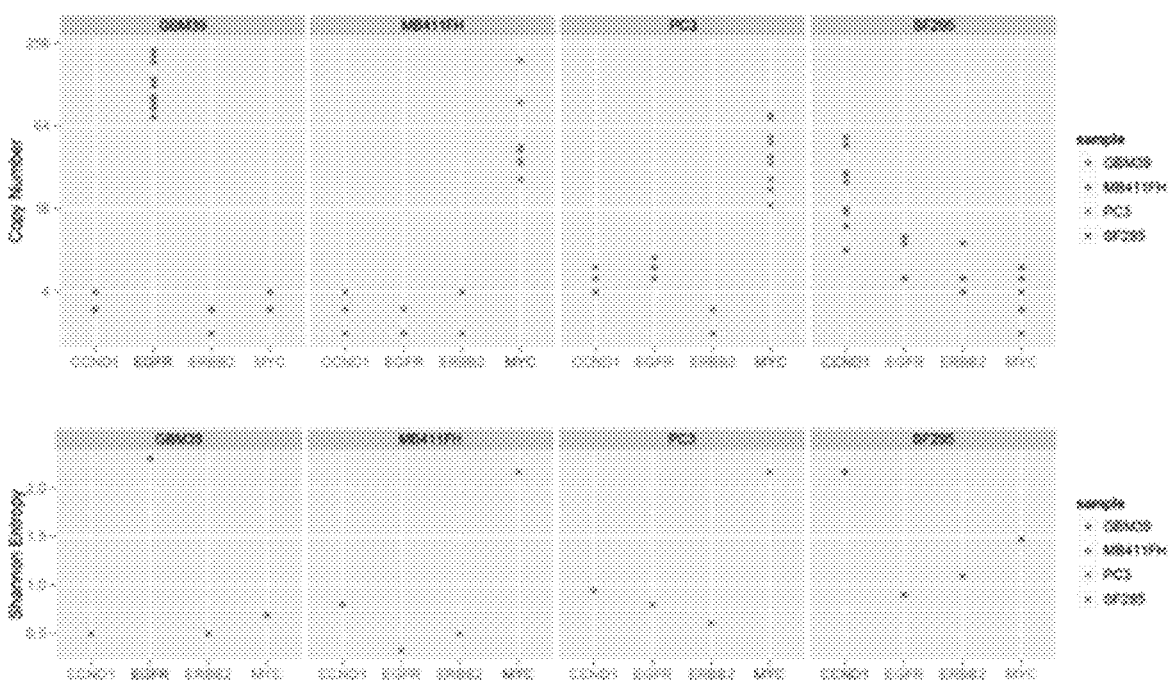
FIG. 11. The figure shows copy number amplification and diversity due to ECDNA. To test how much of the copy number and diversity could be attributed to ECDNA, we chose FISH probes that bind to four of the most commonly amplified oncogenes in our sample set, EGFR, MYC, CCND1 or ERBB2, and quantified the cell-to-cell variability in their DNA copy number in metaphase spreads, from four tumor cell lines: GBM39, MB411FH, SF295 and PC3 cancer cells. For each cell line, only the target oncogene marked in red is known to be amplified on ECDNA (EGFR in GBM39; MYC in MB411FH and PC3, and CCND1 in SF295). The other 3 genes reside on chromosomal loci. The target oncogene shows consistently higher copy numbers (Top Panel) and diversity (Bottom Panel).

WGS with median coverage of 1.19× (FIG. 8) revealed focal amplifications that were nearly identical to the amplifications found in the TCGA analyses of the same cancer types (FIG. 3A), including amplified oncogenes found in a pan-cancer analysis of 13 different cancer types[20]. All of the amplified oncogenes tested were found solely on ECDNA, or concurrently on ECDNA and chromosomal homogenous staining regions (HSRs) (FIG. 3B-3C; FIGS. 9-10). Oncogenes amplified in ECDNA expressed high levels of mRNA transcripts (FIG. 3D) and the copy number diversity of commonly amplified oncogenes in ECDNA far exceeded their copy number diversity if they were on other chromosomal loci (FIG. 11).

Figures 13A, 13B, 13C:
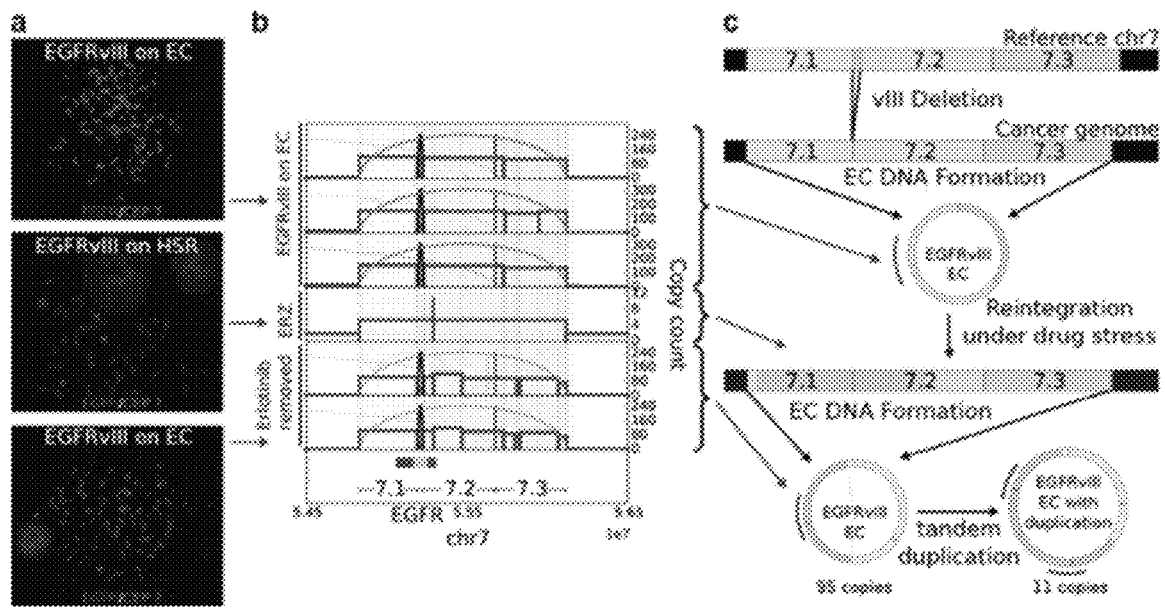
FIGS. 13A-13C. The figures show fine structure analysis of EGFRvIII Amplification in Extrachromosomal or Chromosomal DNA in naive GBM39 cells and in response to Erlotinib Treatment (ERZ) and Drug Withdrawal.

To determine whether extra- and intrachromosomal structures had a common origin, we developed 'AmpliconArchitect' to elucidate the finer genomic structure using sequencing data (Methods). To better understand the relationship between subnuclear location and amplicon structure, we took advantage of spontaneously occurring subclone of GBM39 cells in which high copy EGFRvIII shifted from ECDNA exclusively to HSRs. Independent replicates of GBM39 containing an ECDNA amplicon, revealed a consistent circular structure of 1.29 MB containing one copy of EGFRvIII (FIG. 12). Remarkably, the GBM39 subclone harboring EGFRvIII exclusively on HSRs had an identical structure with tandem duplications containing multiple copies of EGFRvIII, indicating that the HSRs arose from reintegration of EGFRvIII-containing ECDNA elements (FIG. 12)[14]. In GBM39 cells, resistance to the EGFR tyrosine kinase inhibitors is caused by reversible loss of EGFRvIII on ECDNA[21]. Structural analysis revealed a conservation of the fine structure of the EGFRvIII amplicon containing ECDNA in naive cells, in treatment, and upon regrowth with discontinuation of therapy (FIG. 13), indicating that ECDNA can dynamically relocate to chromosomal HSRs while maintaining key structural features[14,22].

Figure 4A:
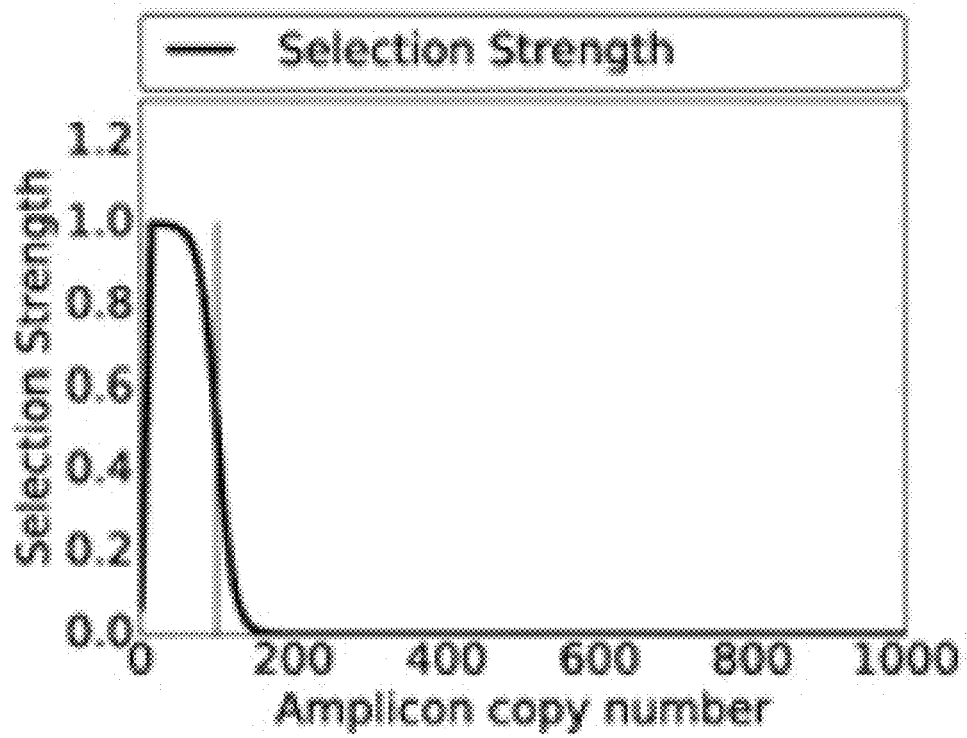
FIGS. 4A-4F. The figures show theoretical model for focal amplification via extrachromosomal (EC) and intrachromosomal (HSR) mechanisms. Simulated change in copy number via random segregation (EC) or mitotic recombination (HSR), starting with $10^5$ cells, 100 of which carry amplifications.
Figure 4B:
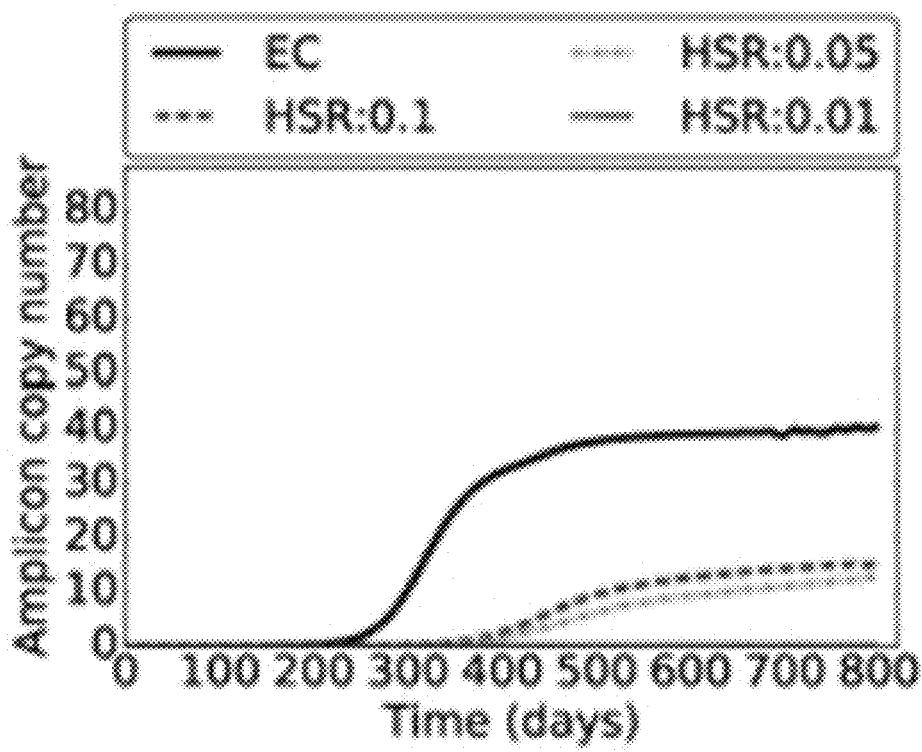
Figure 4C:
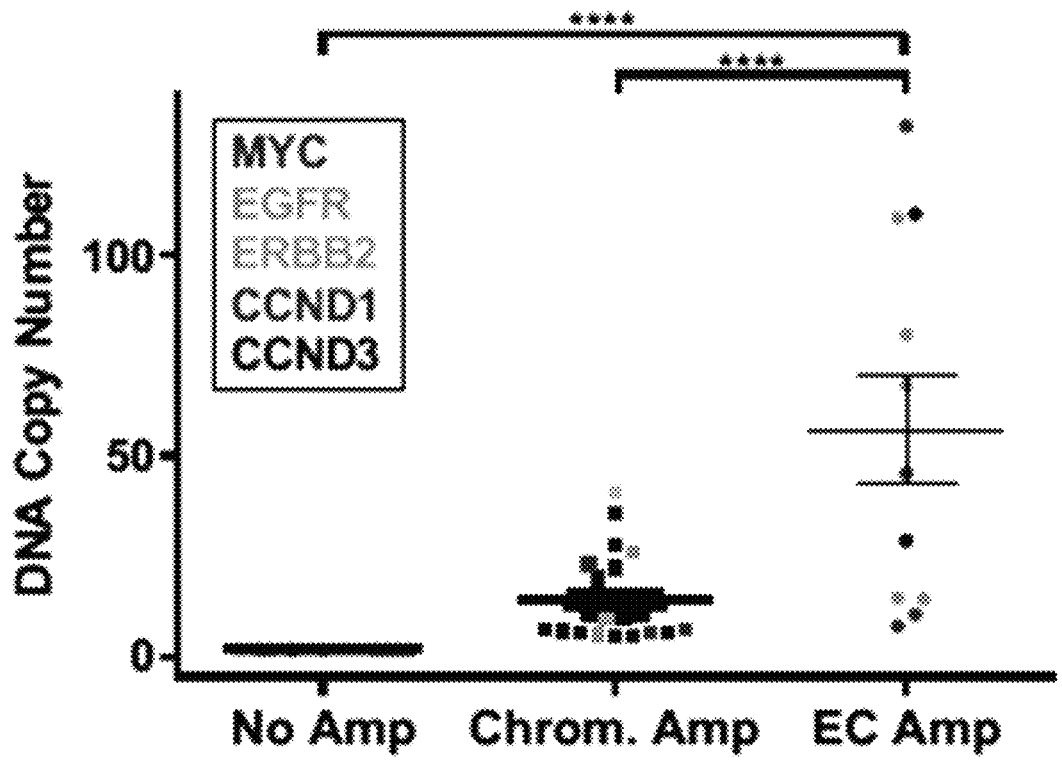
Figure 4D:
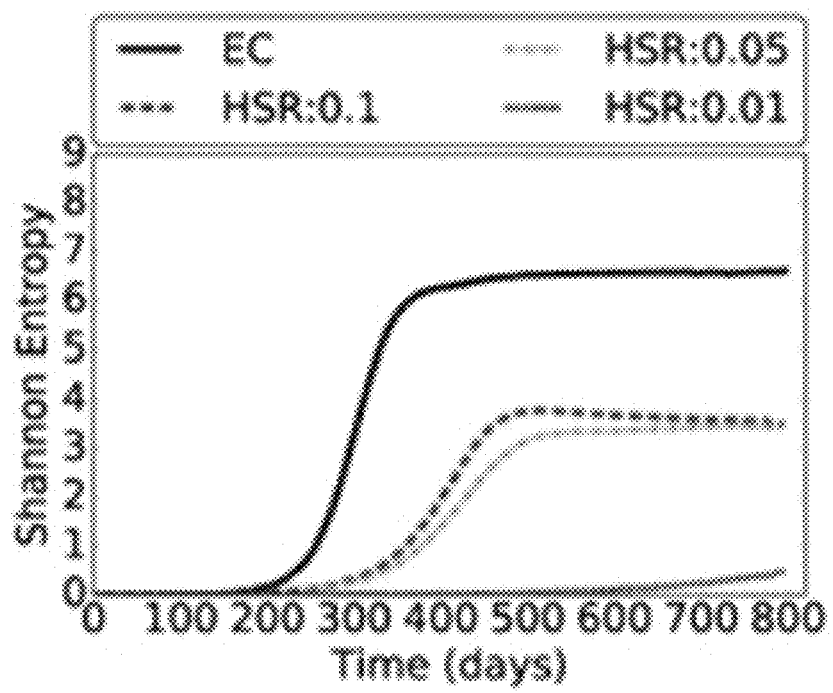
Figure 4E:
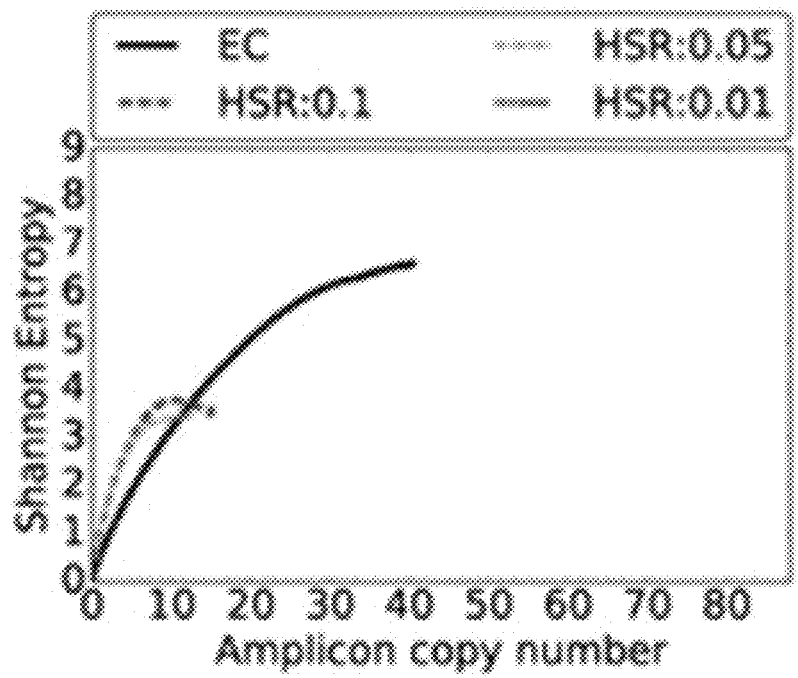
Figure 14:
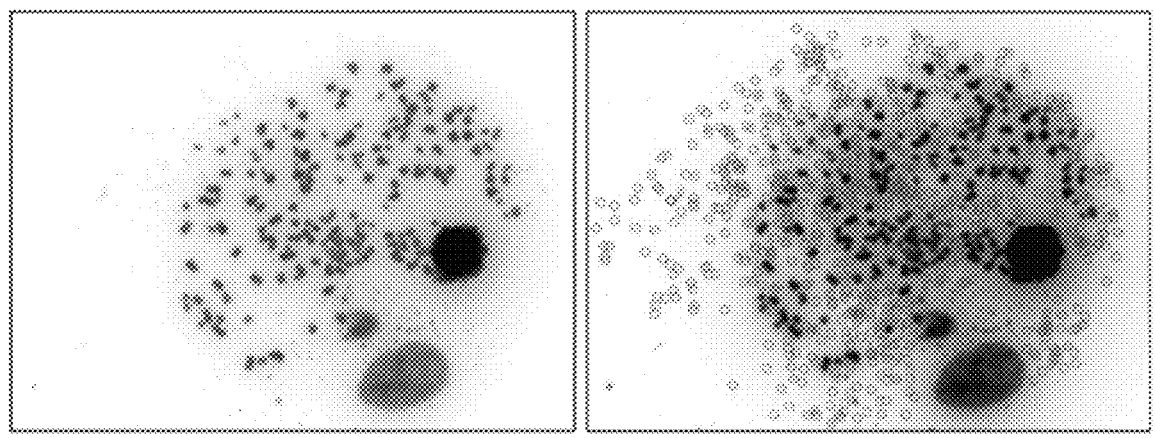
FIG. 14. The figure shows a GBM metaphase spread with large ECDNA counts (>600), as determined by manual counting and ECdetect.

Does ECDNA localization confer any particular benefit? We hypothesized ECDNA amplification may enable an oncogene to rapidly reach higher copy number because of the unequal segregation to daughter cells[15] than would be possible by intrachromosomal amplification. We used a simplified Galton-Watson branching process to model the evolution of a tumor[23], where each cell in the current generation either replicates or dies to create the next generation. A cell with k copies of the amplicon is selected for replication with probability $b_k$; $b_k/(1-b_k)=1+sf_m(k)$. We provided a positive selection bias towards cells with higher ECDNA counts by choosing s∈{0.5,1} along with different selection functions for f. Specifically, $f_m(k)$ increases to a maximum value $f_m(15)=1$, then declines in a logistic manner with $f_m(m)=0.5$ to reflect metabolic constraints (Methods). We allowed the amplicon copy number to grow to 1000 copies (FIG. 14), but set $b_k=0$ for k≥$10^3$. During cell division, the 2 k copies resulting from the replication of each of the k ECDNA copies segregate independently into the two daughter cells. We contrasted this with an intrachromosomal model of duplication with identical selection constraints, but with the change in copy number affected by mitotic recombination, and achieved by incrementing or decrementing k by 1, with duplication probability $p_d$. A range of values for $p_d$, (0.01≤$p_d$≤0.1) was used, where the upper bound reflects a change in copy number once every 5 divisions. The full assumptions of the model are explained in detail in Supplementary Material Section 4. Starting with an initial population of $10^5$ cells, with s=0.5 and m=100 and a selection function $f_{100}(k)$ (FIG. 4A), we find that an oncogene can reach much higher copy number in a tumor if it is amplified on ECDNA, rather than on a chromosome (FIG. 4B). As predicted by the model, we detected significantly higher copy number of the most frequently amplified oncogenes EGFR (including EGFRvIII) and c-MYC, when they were contained within ECDNA instead of within chromosomes (FIG. 4C). We also reasoned that if an oncogene is amplified intra-chromosomally, the heterogeneity of the tumor (in terms of the distribution of copies of the oncogene) would stabilize at a much lower level. In contrast, unequal segregation of ECDNA would be likely to rapidly enhance heterogeneity and maintain it. Our model confirmed this prediction (FIG. 4D), consistently for a wide range of simulation parameters (Supplementary Material Section 4.3). The heterogeneity of copy number change stabilizes and even decreases over time[10,24], much as predicted in FIG. 4C-4D. We also tested the validity of the model by comparing the Shannon entropy against the average number of amplicons per cell in our tumor samples. Heterogeneity of a tumor with respect to oncogene copy number would be more likely to rise relatively slowly if it is present on a chromosome, but would rise more rapidly and be maintained much longer, if that oncogene is present on ECDNA, as confirmed by a plot of Shannon entropy vs copy number (FIG. 4E). Moreover, the predicted correlation in FIG. 4E is completely recapitulated by the experimental data (FIG. 4F), thereby validating the central tenets of the model.

There is growing evidence that genetically heterogeneous tumors are remarkably difficult to treat[10]. The data presented here identifies a mechanism by which tumors maintain cell-to-cell variability in the copy number and transcriptional level of oncogenes that drive tumor progression and drug resistance. We suggest that EC oncogene amplification may enable tumors to adapt more effectively to variable environmental conditions by increasing the likelihood that a subpopulation of cells will express that oncogene at a level that maximizes its proliferation and survival[12,21,25-28], rendering tumors progressively more aggressive and difficult to treat over time. Even when using a selection function that only mildly depends on copy number, we detected a very large difference between intra- and extrachromosomal amplification mechanisms leading to higher copy number of amplicons and greater heterogeneity of copy number. Thus, even small increases in selection advantage conferred by oncogenes amplified on ECDNA would be expected to yield a very high fitness advantage (Supplementary Material Section 4.3). The strikingly high frequency of ECDNA in cancer, as shown here, coupled to the benefits to tumors of EC gene amplification relative to chromosomal inheritance, suggest that oncogene amplification on ECDNA may be a driving force in tumor evolution and the development of genetic heterogeneity in human cancer. Understanding the underlying molecular mechanisms of tumor evolution, including oncogene amplification in ECDNA, may help to identify more effective treatments that either prevent cancer progression or more effectively eradicate it.

Methods

Cytogenetics. Metaphase cells were obtained by treating cells with Karyomax (Gibco) at a final concentration of 0.01 µg/ml for 1-3 hours. Cells were collected, washed in PBS, and resuspended in 0.075 M KCl for 15-30 minutes. Carnoy's fixative (3:1 methanol/glacial acetic acid) was added dropwise to stop the reaction. Cells were washed an additional 3 times with Carnoy's fixative, before being dropped onto humidified glass sides for metaphase cell preparations. For ECdetect analyses, DAPI was added to the slides. Images in the main figures were captured with an Olympus FV1000 confocal microscope. All other images were captured at a magnification of 1000 with an Olympus BX43 microscope equipped with a QiClick cooled camera. FISH was performed by adding the appropriate DNA FISH probe onto the fixed metaphase spreads. A coverslip was added and sealed with rubber cement. DNA denaturation was carried out at 75° C. for 3-5 minutes and the slides were allowed to hybridize overnight at 37° C. in a humidified chamber. Slides were subsequently washed in 0.4×SSC at 50° C. for 2 minutes, followed by a final wash in 2×SSC/0.05% Tween-20. Metaphase cells and interphase nuclei were counterstained with DAPI, a coverslip was applied, and images were captured.

Cell culture. The NCI-60 cell line panel (gift from Andrew Shiau-obtained from NCI) was grown in RPMI-1640 with 10% FBS under standard culture conditions. Cell lines were not authenticated, as they were obtained from the NCI. The PDX cell lines were cultured in DMEM/F-12 media supplemented with Glutamax, B27, EGF, FGF, and Heparin. Lymphoblastoid cells (gifts from Bing Ren) were grown in RPMI-1640, supplemented with 2 mM glutamine and 15% FBS. IMR90 and ALS6-Kin4 (gift from John Ravits and Don Cleveland) cells were grown in DMEM/F-12 supplemented with 20% FBS. Normal human astrocytes (NHA) and normal human dermal fibroblasts (NHDF) were obtained from Lonza and cultured according to Lonza-specific recommendation. Cell lines were not tested for mycoplasma contamination.

Tissue samples. Tissues were obtained from the Moores Cancer Center Biorepository Tissue Shared Resource with IRB approval (#090401). All samples were de-identified and patient consent was obtained. Additional tissue samples that were obtained were approved by the UCSD IRB (#120920).

DNA library preparation. DNA was sonicated to produce 300-500 bp fragments. DNA end repair was performed using End-it (Epicentre), DNA library adapters (Illumina) were ligated, and the DNA libraries were amplified. Paired-end next generation sequencing was performed and samples were run on the Illumina Hi-Seq using 100 cycles.

DNA extraction. Cells were collected and washed with 1× cold PBS. Cell pellets were resuspended in Buffer 1 (50 mM Tris, pH 7.5, 10 mM EDTA, 50 µg/ml RNase A), and incubated in Buffer 2 (1.2% SDS) for 5 minutes on ice. DNA was acidified by the addition of Buffer 3 (3 M CsCl, 1 M potassium acetate, 0.67 M acetic acid) and incubated for 15 minutes on ice. Samples were centrifuged at 14,000×g for 15 minutes at 4° C. The supernatant was added to a Qiagen column and briefly centrifuged. The column was washed (60% ethanol, 10 mM Tris pH 7.5, 50 µM EDTA, 80 mM potassium acetate) and eluted in water.

DNase treatment. Metaphase cells were dropped onto slides and visualized via DAPI. Coverslips were removed and slides washed in 2×SSC, and subsequently treated with 2.5% trypsin, and incubated at 25° C. for 3 minutes. Slides were then washed in 2×SSC, DNase solution (1 mg/ml) was applied to the slide, and cells were incubated at 37° C. for 3 hours. Slides were washed in 2×SSC and DAPI was again applied to the slide to visualize DNA.

ECDNA count statistics. In FIGS. 2A and 2B, the violin plots represent the distribution of ECDNA counts in different sample types. In order to compare the ECDNA counts between the different samples, we use a one-sided Wilcoxon rank sum test, where the null hypothesis assumes the mean ECDNA count ranks of the compared sample types equal.

Estimation of frequency of samples containing ECDNA. There is a wide variation in the number of ECDNA across different samples and within metaphases of the same sample. We want to estimate and compare the frequency of samples containing ECDNA for each sample type. We label a sample as being ECDNA-positive by using the pathology standard: a sample is deemed to be ECDNA-positive if we observe ≥2 ECDNA in ≥2 images out of 20 metaphase images. Therefore, we ensure that every sample contains at least 20 metaphases.

We define indicator variable $X_{ij}=1$ if metaphase image j in sample i has ≥2 ECDNA; $X_{ij}=0$ otherwise. Let $n_i$ be the number of metaphase images acquired from sample i. We assume that $X_{ij}$ is the outcome of the $j^{th}$ Bernoulli trial, where the probability of success $p_i$ is drawn at random from a beta distribution with parameters determined by $\Sigma_j X_{ij}$. Formally, $$p_i \mid \alpha_i, \beta_i \sim \text{Beta}\left(\alpha_i = \max\left\{\epsilon, \sum_j X_{ij}\right\}, \beta_i = \max\{\epsilon, n_i - \alpha_i\}\right)$$

We model the likelihood of observing k successes in n=20 trials using the binomial density function as:

$$k \mid p_i \sim \text{Binom}(p_i, n=20)$$

Finally, the predictive distribution p(k), is computed using the product of the Binomial likelihood and Beta prior, modeled as a "beta-binomial distribution"[29].

$$p(k) = E[k \mid p_i] = \int_0^1 k|p_i \cdot p_i|\alpha_i, \beta_i dp_i$$

$$= \binom{n}{k} \frac{B(k+\alpha_i, n-k+\beta_i)}{B(\alpha_i, \beta_i)}$$

We model the probability for sample i being ECDNA-positive with the random variable $Y_i$ such that:

$$Y_i = 1 - (k=1|p_i) - (k=0|p_i)$$

The expected value of $Y_i$ is:

$$E(Y_i) = 1 - p(k=1) - p(k=0)$$

Let T be the set of samples belonging to a certain sample type t, e.g. immortalized samples.
We define $$Y_T = \frac{\Sigma_{i \in T} Y_i}{|T|}$$

We estimate the frequency of samples under sample t containing ECDNA (bar heights on FIGS. 2C and 2D) as $$E[Y_T] = \frac{\Sigma_{i \in T} E[Y_i]}{|T|}$$

and error bar heights (FIGS. 2C and 2D) as:

$$sd(Y_T) = \frac{(\Sigma_{i \in T} \text{Var}[Y_i])^{\frac{1}{2}}}{|T|}$$

assuming independence among samples i∈T. For any $\alpha_i$ or $\beta_i = 0$, we assign them a sufficiently small ε. For more detail, please see Supplementary Material Section 1.

Comparison of ECDNA presence between different sample types. We construct binary ECDNA presence distributions, based on the ECDNA counts, such that an image with ≥2 ECDNA is represented as a 1, and 0 otherwise. In order to compare the ECDNA presence between the different samples, we use a one-sided Wilcoxon rank sum test using the binary ECDNA presence distributions, where the null hypothesis assumes the mean ranks of the compared sample types equal.

ECdetect: Software for detection of extrachromosomal DNA from DAPI staining metaphase images. The software applies an initial coarse adaptive thresholding[30,31] on the DAPI images to detect the major components in the image with a window size of 150×150 pixels, and T=10%. Components breaching 3000 pixels and 80% of solidity are masked, and small components discarded. Weakly connected components (CC) of the remaining binary image are computed to find the separate chromosomal regions. CC breaching a cumulative pixel count of 5000 are considered as candidate search regions, and their convex hull with a dilation of 100 pixels are added into the ECDNA search region. Following the manual masking and verification of the ECDNA search region, a second finer adaptive thresholding with a window size of 20×20 pixels and T=7% is performed. Components that are greater than 75 pixels are designated as non-ECDNA structures and their 15 pixel neighborhood is removed from the ECDNA search region. Any component detected with a size less than or equal to 75 and greater than or equal to 3 pixels inside the search region is detected as ECDNA. For more detail, please see Supplementary Material Section 2.

Bioinformatic datasets. We sequenced 117 tumor samples including 63 cell lines, 19 neurospheres and 35 cancer tissues with coverage ranging from 0.6× to 3.89× and an additional 8 normal tissues as controls. See FIG. 19 for the coverage distribution across samples. We mapped the sequencing reads from each sample to hg19 (GRCh37) human reference genome[32] from UCSC genome browser[33] using BWA software version 0.7.9a[34]. We inferred an initial set of copy number variants from these mapped sequence samples using the ReadDepth CNV software[35] version 0.9.8.4 with parameters FDR=0.05 and overDispersion=1.

We downloaded copy number variation calls (CNV) for 11079 tumor-normal samples covering 33 different tumor types from TCGA. We applied similar filtering criteria to ReadDepth output and TCGA calls to eliminate false CN amplification calls from repetitive genomic regions and hotspots for mapping artefacts.

We used the filtered set of CNV calls from ReadDepth as input probes for AmpliconArchitect which revealed the final set of amplified intervals and the architectures of the amplicons. See Supplementary Material Section 3 for more details.

Reconstruction using AmpliconArchitect. We developed a novel tool AmpliconArchitect (AA), to automatically identify connected amplified genomic regions and reconstruct plausible amplicon architectures. For each sample, AA takes as input an initial list of amplified intervals and whole genome sequencing (WGS) paired-end reads aligned to the human reference. It implements the following steps to reconstruct the one or more architectures for each amplicon present in the sample: (a) Use discordant read-pair alignments and coverage information to iteratively visit and extend connected genomic regions with high copy numbers. (b) For each set of connected amplified regions, segment the regions based on depth of coverage using a mean-shift segmentation to detect copy number changes and discordant read-pair clusters to identify genomic breaks. (c) Construct a breakpoint graph connecting segments using discordant read-pair clusters. (d) Compute a maximum likelihood network to estimate copy counts of genomic segments. (e) Report paths and cycles in the graph that identify the dominant linear and circular structures representing one. (Supplementary Material Section 3)

Comparison of CNV gains between the sequencing sample set and TCGA. We compared our sample set against TCGA samples to test the assumption that the genomic intervals amplified in our sample set are broadly representative of a pan-cancer dataset, by comparing against TCGA samples. Here, we deal with an abstract notation to represent different datasets and describe a generic procedure to compare amplified regions. Consider a set of K samples. For any k∈[1, . . . , K], let $S_k$ denote the set of amplified intervals in sample k.

Let c be the cancer subtype for sample k. We compare $S_k$ against TCGA samples with sub-type c. Let T denote the set of all genomic regions which are amplified in at least 1% of TCGA samples of subtype c. For each interval t∈T, let $f_t$ denote its frequency in TCGA samples of subtype c. We define a match score $$d_k = \sum_{t \in S_{k,T}} f_t \quad S_{k,T} = \{T \in T \text{ s.t. } t \text{ overlaps an intervals in } S_k\}$$

The cumulative match score for all samples is defined as:

$$D = \sum_{t \leq k \leq K} d_k$$

To compute the significance of statistic D, we do a permutation test. We generate N random permutations of the TCGA intervals for subtype c and estimate distribution of match scores of our sample set against the random permutations. We choose a random assignment of locations of all intervals in T, while retaining their frequencies. For the $j^{th}$ permuted set $T_j$, we computed the cumulative match score $D_j$ relative to our sample set. Thus the significance of overlap between our sample set and the TCGA amplified intervals is estimated by the fraction of random permutations with $D_j > D$. Computing 1 million random permutations generated exactly one permutation breaching the TCGA score D, implying a p-value $\leq 10^{-6}$.

Oncogene Enrichment. We compared the rank correlation of the most frequent oncogenes in our sample set with the top oncogenes as reported by TCGA pan-cancer analysis by Zack et al[20]. We identified 14 oncogenes occurring in 2 or more samples of our sample set and compared these with the top 10 oncogenes from the TCGA pan-cancer analysis. We found that 7 out of the top 10 oncogenes were represented in our list of 14 oncogenes. Considering 490 oncogenes in the COSMIC database, the significance of observing 7 or more oncogenes in common in the two datasets is given by the hypergeometric probability $$p = \sum_{i=7}^{10} \frac{\binom{480}{14-i}\binom{10}{i}}{\binom{490}{14}} = 3.07 \cdot 10^{-10}$$

Figure 23:
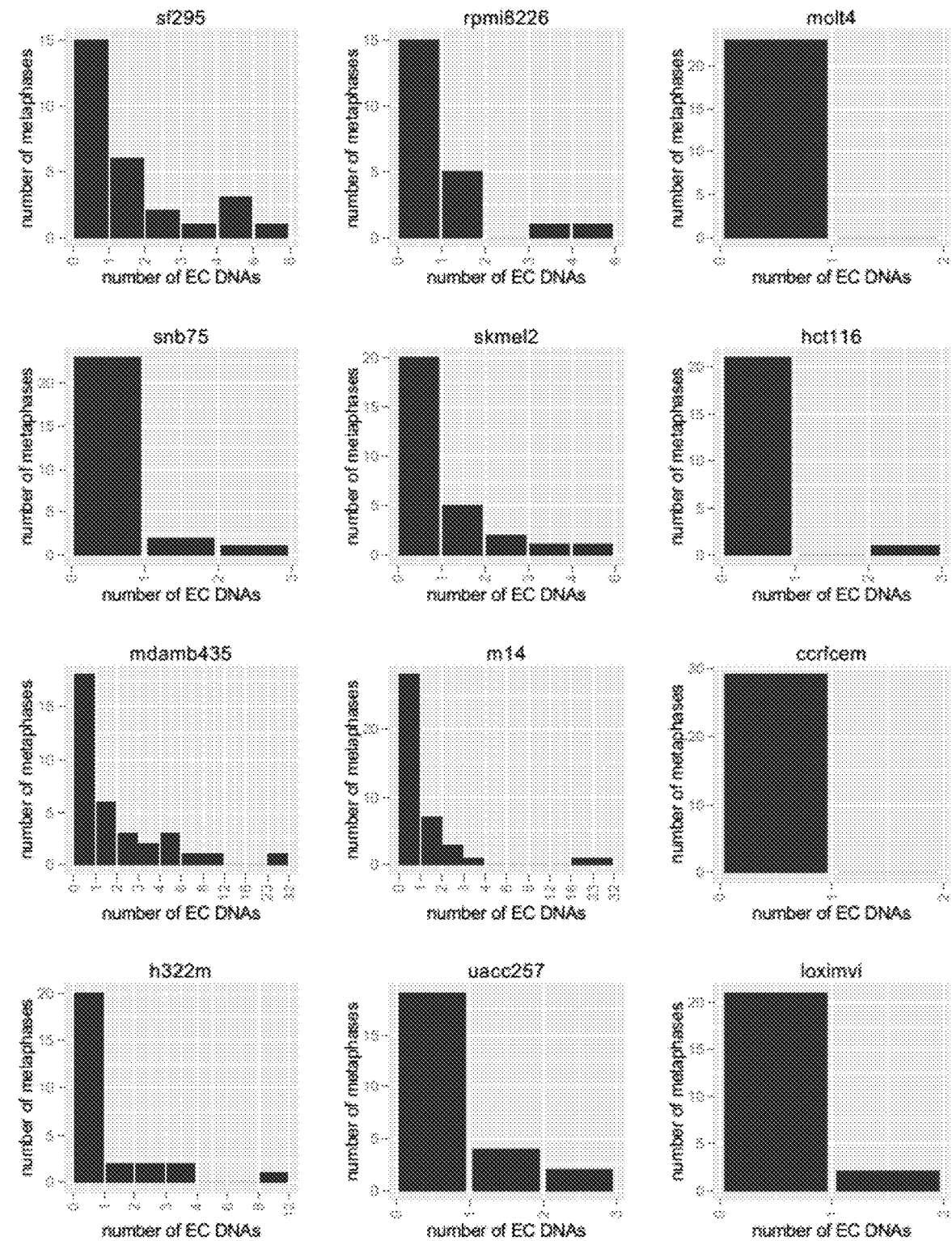
FIG. 23. The figure shows ECDNA count histograms of tumor cell line samples.
Figure 24:
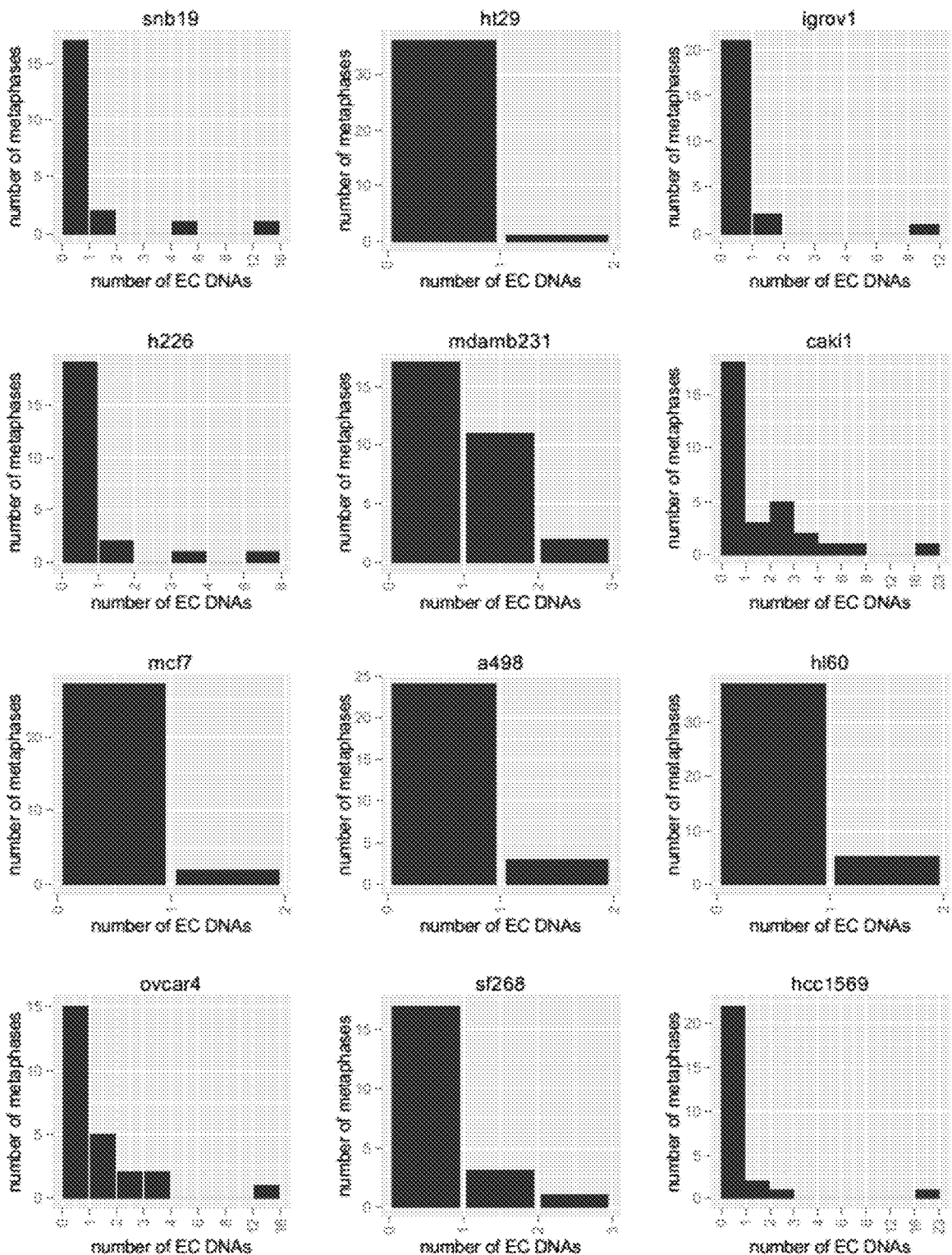
FIG. 24. The figure shows ECDNA count histograms of tumor cell line samples.
Figure 25:
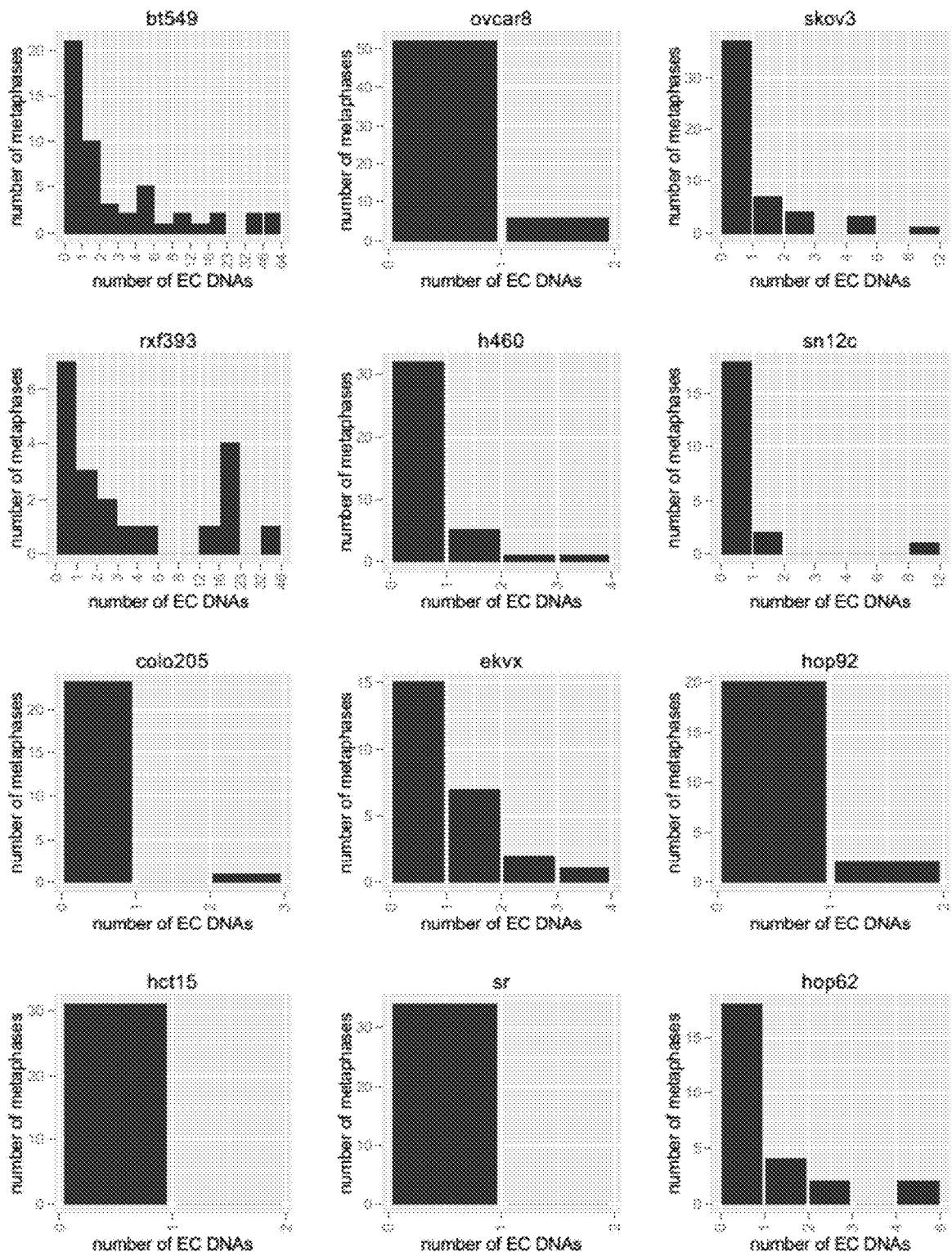
FIG. 25. The figure shows ECDNA count histograms of tumor cell line samples.
Figure 26:
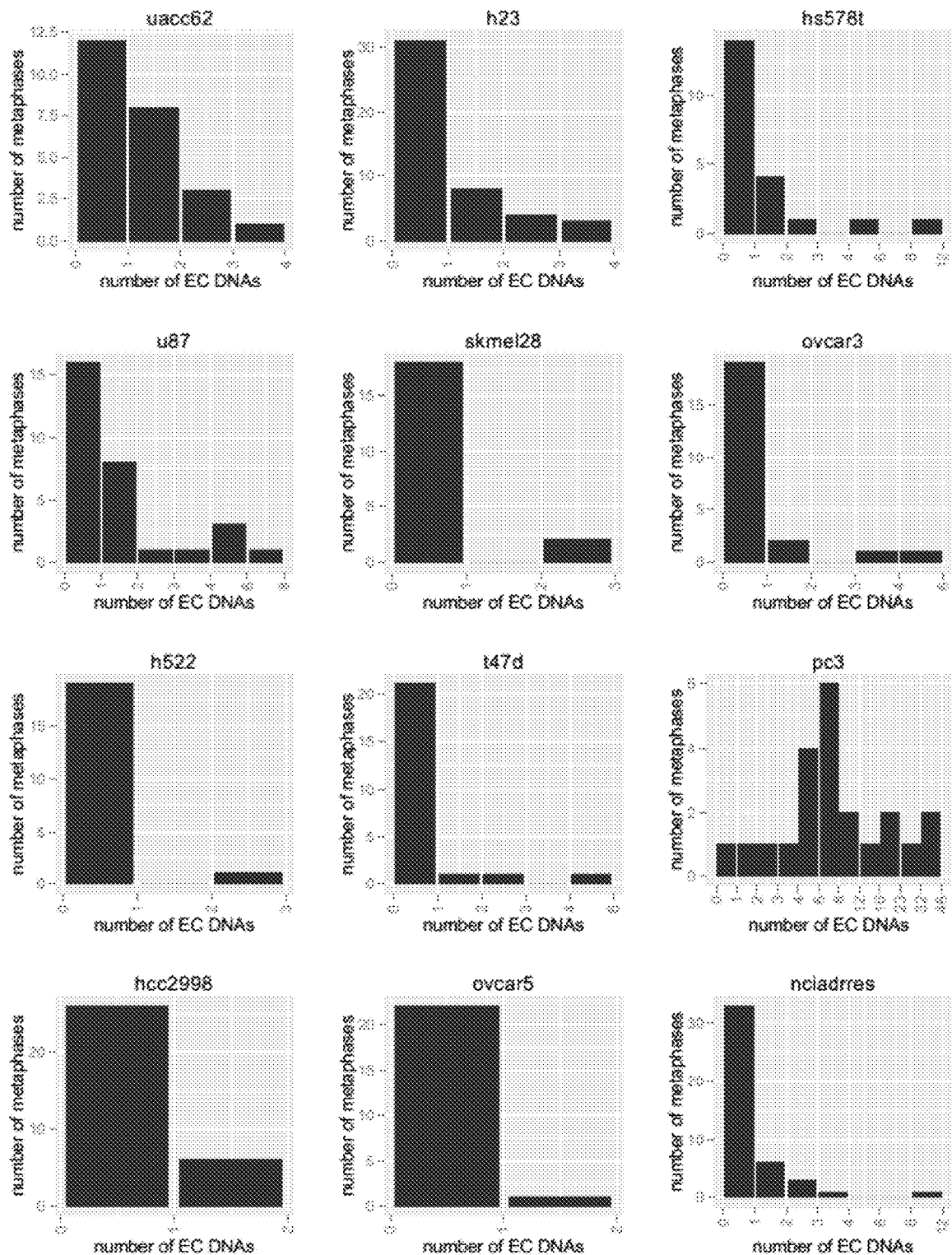
FIG. 26. The figure shows ECDNA count histograms of tumor cell line samples.
Figure 27:
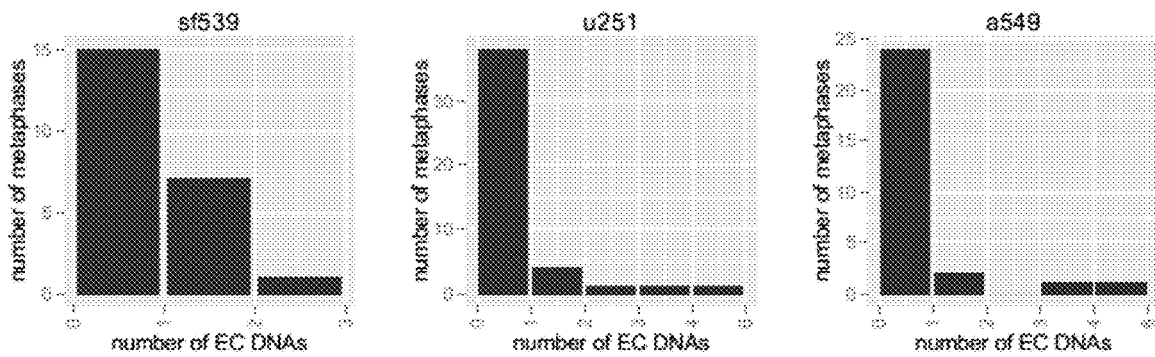
FIG. 27. The figure shows ECDNA count histograms of tumor cell line samples.
Figure 28:
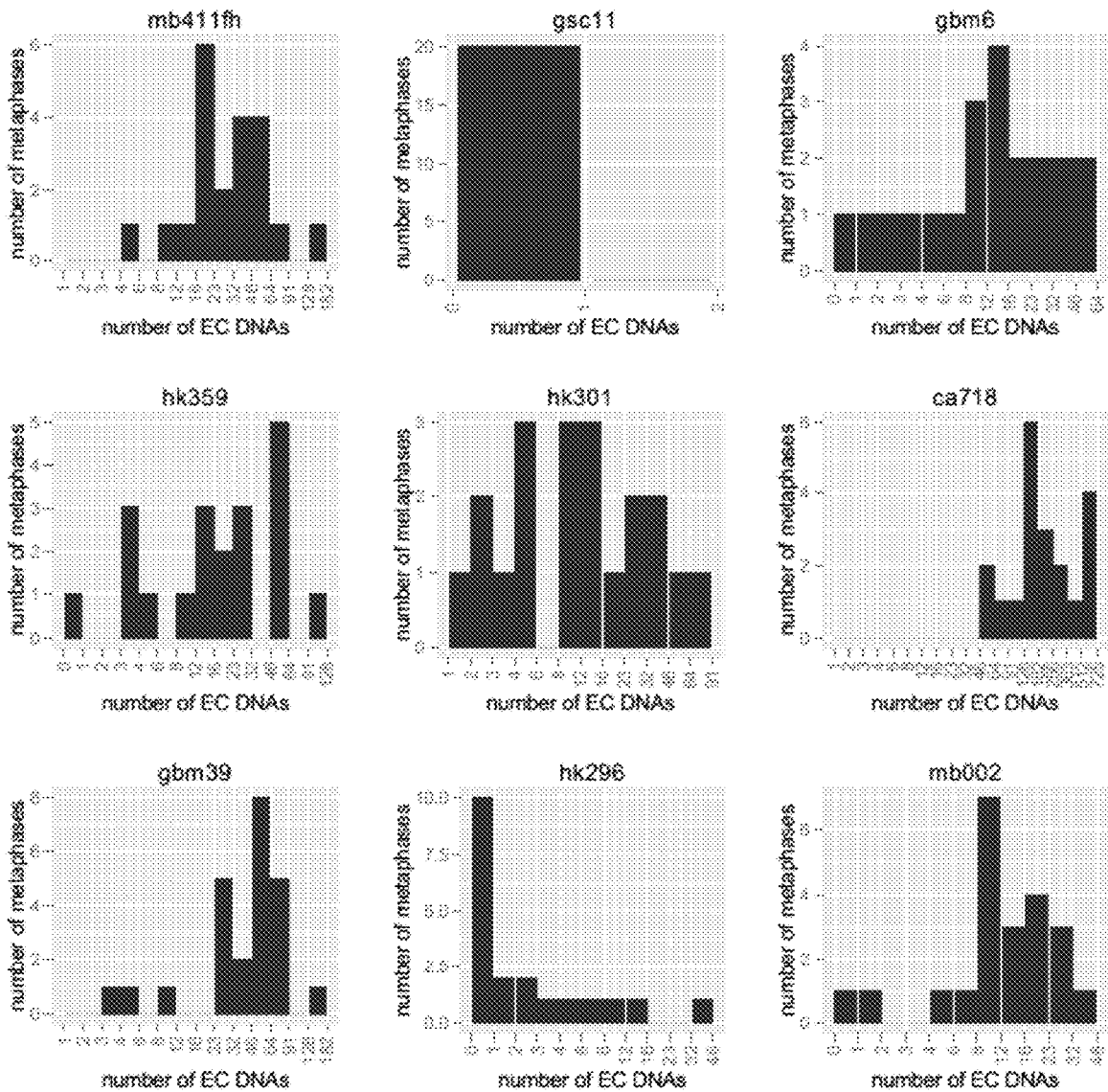
FIG. 28. The figure shows ECDNA count histograms of tumor PDX samples.

Amplicon structure similarity. We found high similarity between amplicon structures of biological replicates (e.g. FIG. 23). We estimate probability of common origin between two samples by measuring the pairwise similarity between amplicon structures. In reconstructing the structures (Supplementary Material Section 3), we identify a set of locations representing change in copy number and we use the locations of change in copy number to estimate the similarity in amplicon structures.

Let L be the total length of amplified intervals. These intervals are binned into windows of size r, resulting in $N_b = L/r$ bins. We use a segmentation algorithm that determines if there is a change in copy number in any bin, within a resolution of r=10,000 bp. (See Meanshift in coverage: Supplementary Materials Section 3.2.) Note that this is an over-estimate, since with split-reads and high density sequencing data, we can often get the resolution down to a few base pairs. Let $S_1$ and $S_2$ represent the set of bins with copy number changes in the two samples, respectively. $S_1$ and $S_2$ are selected from a candidate set of locations $N_b$. Under the null hypothesis that $S_2$ is random with respect to $S_1$, we expect $I=S_1 \cap S_2$ to be small. Let $m=\min\{|S_1|, |S_2|\}$, and $M=\max\{|S_1|, |S_2|\}$. A p-value is computed as follows:

$$p = \sum_{i=|I|}^{m} \frac{\binom{N_b - m}{M - i}\binom{m}{i}}{\binom{N_b}{M}}$$

In looking at GBM39 replicates (FIG. 12), we find that all replicates displaying EGFR ECDNA are similar to each other. Comparing replicates in row 1 and row 2 among $|N_b|=129$ bins (1.29 Mbp), $|S1|=5$ corresponding to row 1 (EC sample), $|S2|=6$ corresponding to row 2 (EC sample) and intersection set size $|I|=5$, we compute the p-value for observing such structural similarity by random chance is $2.18 \times 10^{-8}$ which is the highest p-value among all EC replicate pairs. In addition, we compare the replicates displaying EGFR on ECDNA with the culture displaying EGFR on HSR. Among $|N_b|=129$ bins, $|S1|=6$ corresponding to row 2 (EC), $|S2|=4$ corresponding to row 4 (HSR), the intersection set has size $|I|=4$ intervals giving a p-value of $1.98 \times 10^{-5}$ which gives the highest p-value among the 3 ECDNA replicates compared to the HSR culture, suggesting a common origin.

A branching process model for oncogene amplification. Consider an initial population of $N_0$ cells, of which $N_\alpha$ cells contain a single extra copy of an oncogene. We model the population using a discrete generation Galton-Watson branching process[23]. In this simplified model, each cell in the current generation containing k amplicons (amplifying an oncogene) either replicates with probability $b_k$ to create the next generation, or dies with probability $1-b_k$ to create the next generation. We set the selective advantage $$\frac{b_k}{1-b_k} = \begin{cases} 1 + sf_m(k) & 0 \leq k < M_\alpha \\ 0 & \text{otherwise} \end{cases} \quad (1)$$

In other words, cells with k copies of the amplicon stop dividing after reaching a limit of $M_\alpha$ amplicons. Otherwise, they have a selective advantage for $0 < k \leq M_\alpha$, where the strength of selection is described by $f_m(k)$, as follows:

$$f_m(k) = \begin{cases} \dfrac{k}{M_s} & (0 \leq k \leq M_s) \\ \dfrac{1}{1 + e^{-\alpha(k-m)}} & (M_s < k < M_\alpha) \end{cases} \quad (2)$$

Here, s denotes the selection-coefficient, and parameters m and α are the 'mid-point', and 'steepness' parameters of the logistic function, respectively. Initially, $f_m(k)$ grows linearly, reaching a peak value of $f_m(k)=1$ for $k=M_s$. As the viability of cells with large number of amplicons is limited by available nutrition[36], $f_m(k)$ decreases logistically in value for $k > M_s$ reaching $f_m(k) \to 0$ for $k > M_\alpha$. We model the decrease by a sigmoid function with a single mid-point parameter m s.t. $f_m(m)=\frac{1}{2}$. The 'steepness' parameter a is automatically adjusted to ensure that $\min\{1-f_m(M_s), f_m(M_\alpha)\} \to 0$.

The copy number change is affected by different mechanisms for extrachromosomal (EC) and intrachromosomal (HSR) models. In the EC model, the available k amplicons are on EC elements which replicate and segregate independently. We assume complete replication of EC elements so that there are 2 k copies which are partitioned into the two daughter cells via independent segregation. Formally, the daughter cells end up with $k_1$ and $k_2$ amplicons respectively, where $$k_1 \sim B(2k, \tfrac{1}{2}) \quad (3)$$

$$k_2 = 2k - k_1 \quad (4)$$

In contrast, in the intrachromosomal model, the change in copy number happens via mitotic recombination, and the daughter cell of a cell with k amplicons will acquire either k+1 amplicons or k−1 amplicons, each with probability $p_d$. With probability $1-2p_d$, the daughter cell retains k amplicons. See Supplementary Material Section 4 for more details.

Supplementary Information.

Section 1: ECDNA Count and Presence Statistics.

Estimation of Frequency of Samples Containing ECDNA:

There is a wide variation on the number of ECDNA across different samples and within metaphases of the same sample. We want to estimate and compare the frequency of samples containing ECDNA for each sample type. We label a sample as being EC-positive by using the pathology standard: a sample is deemed to be EC-positive if we observe ≥2 ECDNA in ≥2 images out of 20 metaphase images. Therefore, we ensure that every sample contains at least 20 metaphases.

We define indicator variable $X_{ij}=1$ if metaphase image j in sample i has ≥2 ECDNA; $X_{ij}=0$ otherwise. Let $n_i$ be the number of metaphase images acquired from sample i. We assume that $X_{ij}$ is the outcome of the j-th Bernoulli trial, where the probability of success pi is drawn at random from a beta distribution with parameters determined by $\Sigma_j X_{ij}$. Formally, $$p_i \mid \alpha_i, \beta_i \sim \text{Beta}\left(\alpha_i = \max\left\{\epsilon, \sum_j X_{ij}\right\}, \beta_i = \max\{\epsilon, n_i - \alpha_i\}\right). \quad (1.1)$$

We model the likelihood of observing k successes in n=20 trials using the binomial density function as:

$$k \mid p_i \sim \text{Binom}(p_i, n=20) \quad (1.2)$$

Finally, the predictive distribution p(k), is computed using the product of the Binomial likelihood and Beta prior, modeled as a "beta-binomial distribution" [29].

$$p(k) = \mathbb{E}_{p_i}[k \mid p_i] \quad (1.3)$$
$$= \int_0^1 k \mid p_i \cdot p_i \mid \alpha_i, \beta_i \, dp_i$$
$$= \int_0^1 \binom{n}{k} p_i^k (1-p_i)^{n-k} \cdot \frac{1}{B(\alpha_i, \beta_i)} p_i^{\alpha_i - 1} (1-p_i)^{\beta_i - 1} dp_i$$
$$= \binom{n}{k} \frac{1}{B(\alpha_i, \beta_i)} \int_0^1 p_i^{k+\alpha_i-1}(1-p_i)^{n-k+\beta_i-1} dp_i$$
$$= \binom{n}{k} \frac{B(k+\alpha_i, n-k+\beta_i)}{B(\alpha_i, \beta_i)}$$

We model the probability for sample i being EC-positive with the random variable Yi such that:

$$Y_i = 1 - Pr(\text{sample } i \text{ is } EC\text{-negative}) \quad (1.4)$$
$$= 1 - (k=1 \mid p_i) - (k=0 \mid p_i)$$

The expected value of $Y_i$ is:

$$\mathbb{E}_{p_i}(Y_i) = 1 - p(k=1) - p(k=0) \quad (1.5)$$
$$= 1 - \binom{20}{1}\frac{B(1+\alpha_i, 19+\beta_i)}{B(\alpha_i, \beta_i)} - \binom{20}{0}$$
$$\binom{20}{0}\frac{B(\alpha_i, 20+\beta_i)}{B(\alpha_i, \beta_i)}$$

The variance of $Y_i$ is:

$$\text{Var}(Y_i) = \text{Var}(k=1 \mid p_i) + \text{Var}(k=0 \mid p_i) + 2\text{Cov}(k=1 \mid p_i, k=0 \mid p_i), \quad (1.6)$$

where $$\text{Var}(k \mid p_i) = \mathbb{E}_{p_i}[(k \mid p_i)^2] - \mathbb{E}_{p_i}[k \mid p_i]^2 \quad (1.7)$$
$$= \int_0^1 (k \mid p_i)^2 \cdot p_i \mid \alpha_i, \beta_i dp_i -$$
$$= \left(\int_0^1 k \mid p_i \cdot p_i \mid \alpha_i, \beta_i dp_i\right)^2 \binom{n}{k}\binom{n}{k}\frac{1}{B(\alpha_i, \beta_i)} \int_0^1$$
$$p_i^{k+\alpha_i-1}(1-p_i)^{2n-2k+\beta_i-1} dp - \binom{n}{k}\binom{n}{k}\frac{B(k+\alpha_i, n-k+\beta_i)^2}{B(\alpha_i, \beta_i)^2}$$
$$= \binom{n}{k}\binom{n}{k}\frac{1}{B(\alpha_i, \beta_i)}[B(2k+\alpha_i, 2n-2k+\beta_i) - \frac{B(k+\alpha_i, n-k+\beta_i)^2}{B(\alpha_i, \beta_i)^2}],$$

and $$\text{Cov}(k=1 \mid p_i, k=0 \mid p_i) = \mathbb{E}_{p_i}[k=1 \mid p_i \cdot k=0 \mid p_i] - \quad (1.8)$$
$$\mathbb{E}_{p_i}[k=0 \mid p_i]\mathbb{E}_{p_i}[k=1 \mid p_i]$$
$$= \binom{n}{k}\binom{n}{k}\frac{1}{B(\alpha_i, \beta_i)}$$
$$\left[\int_0^1 p^{1+\alpha_i-1}(1-p_i)^{2n-1\to\beta_i-1} dp_i - \frac{B(\alpha_i, n+\beta_i)B(1+\alpha_i, n-1+\beta_i)}{B(\alpha_i, \beta)}\right]$$
$$= \binom{n}{k}\binom{n}{k}\frac{1}{B(\alpha_i, \beta_i)}[B(1+\alpha_i, 2n-1+\beta_i) - \frac{B(\alpha_i, n+\beta_i)B(1+\alpha_i, n-1+\beta_i)}{B(\alpha_i, \beta)}].$$

Let T be the set of samples belonging to a certain sample type t, e.g. immortalized samples. We define $$Y_T = \frac{\sum_{i \in T} Y_i}{|T|} \quad (1.9)$$

We estimate the frequency of samples under sample t containing ECDNA (bar heights on FIGS. 2C and 2D) as $$\mathbb{E}[Y_T] = \frac{\sum_{i \in T} \mathbb{E}[Y_i]}{|T|} \quad (1.10)$$

and error bar heights (FIGS. 2C and 2D) as:

$$sd(Y_T) = \frac{(\sum_{i \in T} \mathrm{Var}[Y_i])^{\frac{1}{2}}}{|T|} \quad (1.11)$$

assuming independence among samples i∈T. For any $\alpha i$ or $\beta i=0$, we assign them a sufficiently small $\epsilon$.

Section 2: ECdetect Software for Detection of Extrachromosomal DNA from DAPI Staining Metaphase Images.

Section 2.1 Introduction.

The DAPI staining metaphase image extrachromosomal DNA (ECDNA) detection software provides a conservative estimation to the number of ECDNA in DAPI staining metaphase images. The software performs a pre-segmentation of the image in order to distinguish chromosomal and non-chromosomal structures, and computes an ECDNA search region of interest (ROI). The designated ROI is displayed on a user interface for the investigator to modify via masking and unmasking desired regions on the image, to correct for potential inaccurate segmentation and/or exclude debris from the ROI. The modifications made on the ROI are saved once verified, and are available for future usage. The output of the software includes the original images with ECDNA detections overlayed, the count of ECDNA found, and their coordinates in the image. ECdetect does not require a pan-centromeric probe, and works on DAPI staining metaphase images only, therefore any detected ECDNA is assumed to not contain a centromere.

Section 2.2 Software

Input. The ECDNA detection software uses Tagged Image File Format (.tiff) DAPI staining metaphase images. In this project we used 2572 images, after checking for duplicates, each at resolution 1392×1040. The investigator needs to provide the parent folder containing all imaging data as input and no other parameter will be required. The software will recursively process every tiff image under the parent folder.

Image pre-segmentation. The software applies an initial coarse adaptive thresholding [31, 30] to detect the major components in the image, with a window size of 150×150 pixels, and T=10%. After filling the closed structures, components breaching 3000 pixels and 80% of solidity (the ratio of the area of the component to the area of its convex hull) are masked as non-chromosomal regions in order to remove the intact nuclei regions from subsequent analysis. Small components are also discarded, and the remaining image is accepted as the binary chromosomal image (BCI). The weakly connected components of the BCI are computed to find the separate chromosomal regions. The weakly connected components breaching a cumulative pixel count of 5000 are considered as candidate search regions, and their convex hull with a dilation of 100 pixels are added into the ECDNA search region of interest (ROI).

Figure 15A:
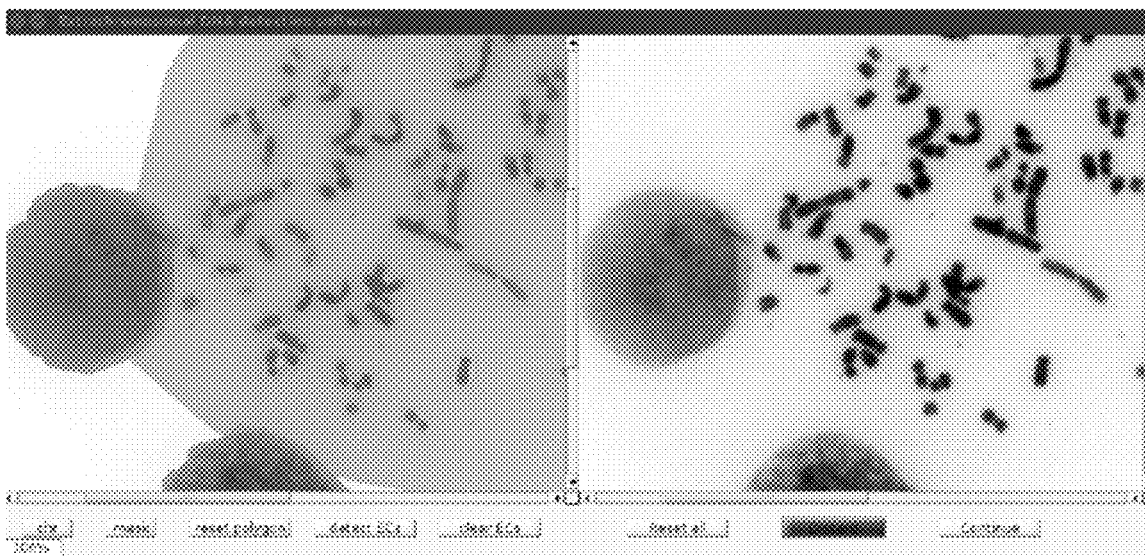
FIGS. 15A-15B. The figures show user interface for ECDNA search ROI verification.
Figure 15B:
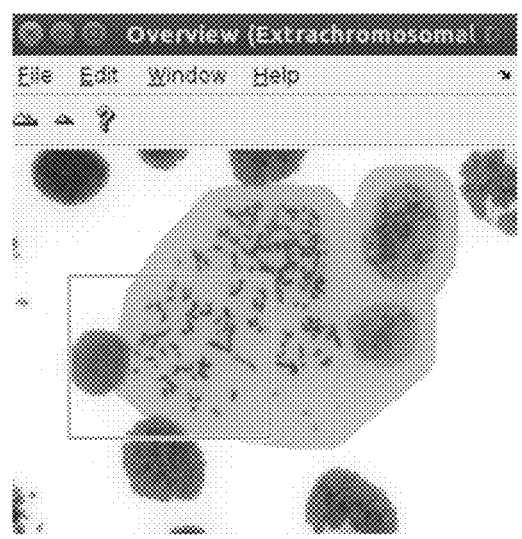

ROI verification. The software provides a user interface as shown in FIG. 15, where the original DAPI image is displayed next to its segmentation result, alongside an overview image. We manually masked any non-chromosomal region that the software failed to discard during the pre-segmentation as shown in FIG. 16. Similarly, we also unmasked any region that the software mistakenly discarded as non-chromosomal region.

ECDNA detection. FIG. 17 shows the steps of ECDNA detection. After the verification of the ECDNA search ROI (FIG. 17a), the software applies a 2-D Gaussian smoothing to the image with standard deviation of 0.5, performs a second finer adaptive thresholding, with a window size of 20×20 pixels and T=7%, and fills any closed structures. Components that are greater than 75 pixels are designated as non-ECDNA structures and their 15-pixel neighborhood is removed from the ECDNA search ROI, in order not to mistakenly call chromosomal extensions or other near intact nuclei structures as ECDNA (FIG. 17b). Any component detected with a size less than or equal to 75 and greater than or equal to 3 pixels inside the final search ROI is returned as ECDNA (FIG. 17c).

Output. The detected ECDNA elements are shown in the original image with overlayed red circles, as well as their coordinates in a separate file for every image. The total ECDNA count per image is also recorded.

Figure 18:
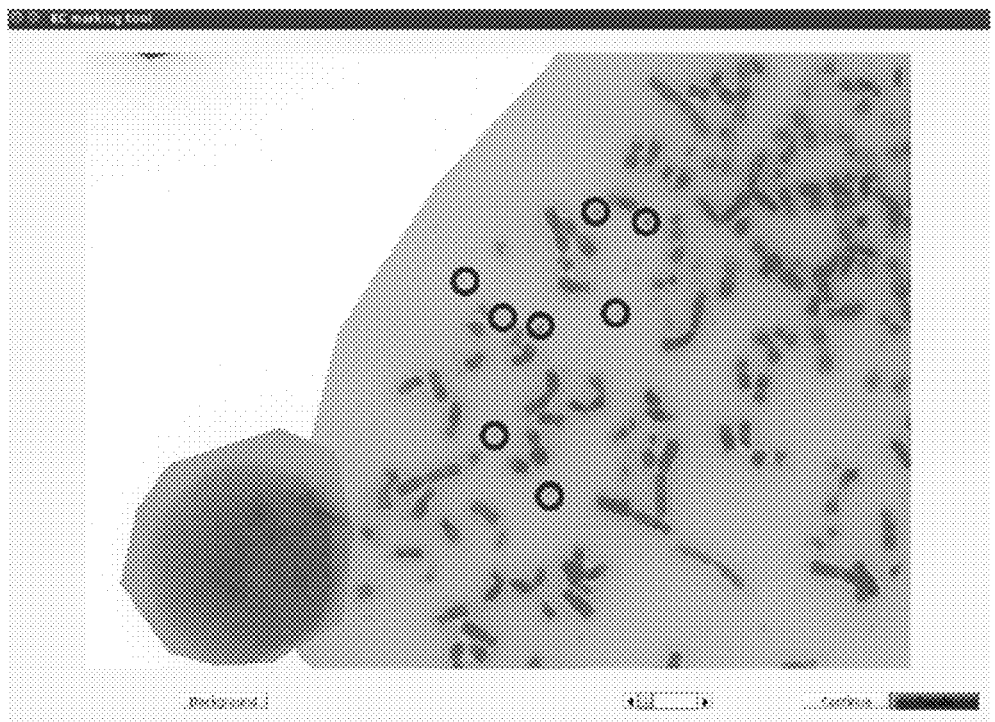
FIG. 18. The figure shows manual marking of ECDNA.

Manual ECDNA marking. For ECDNA detection evaluation purposes, we allowed the investigator to manually select the ECDNA structures while being able to have access to the verified ECDNA search region (including the chromosome region neighborhood) and segmentation results, alongside zooming, if desired. FIG. 18 shows an example set of marked ECDNA at a specified zooming level.

Figures 19A, 19B, 19C, 19D, 19E, 19F:
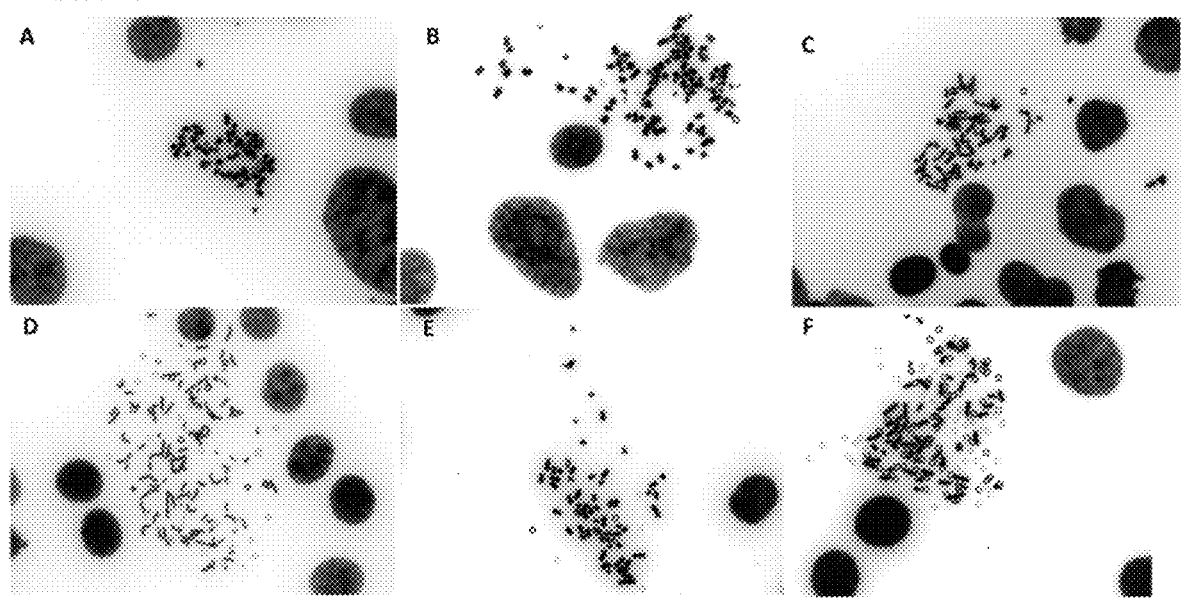
FIGS. 19A-19F. The figures show ECDNA count histograms for representative examples of cell lines.
Figure 20:
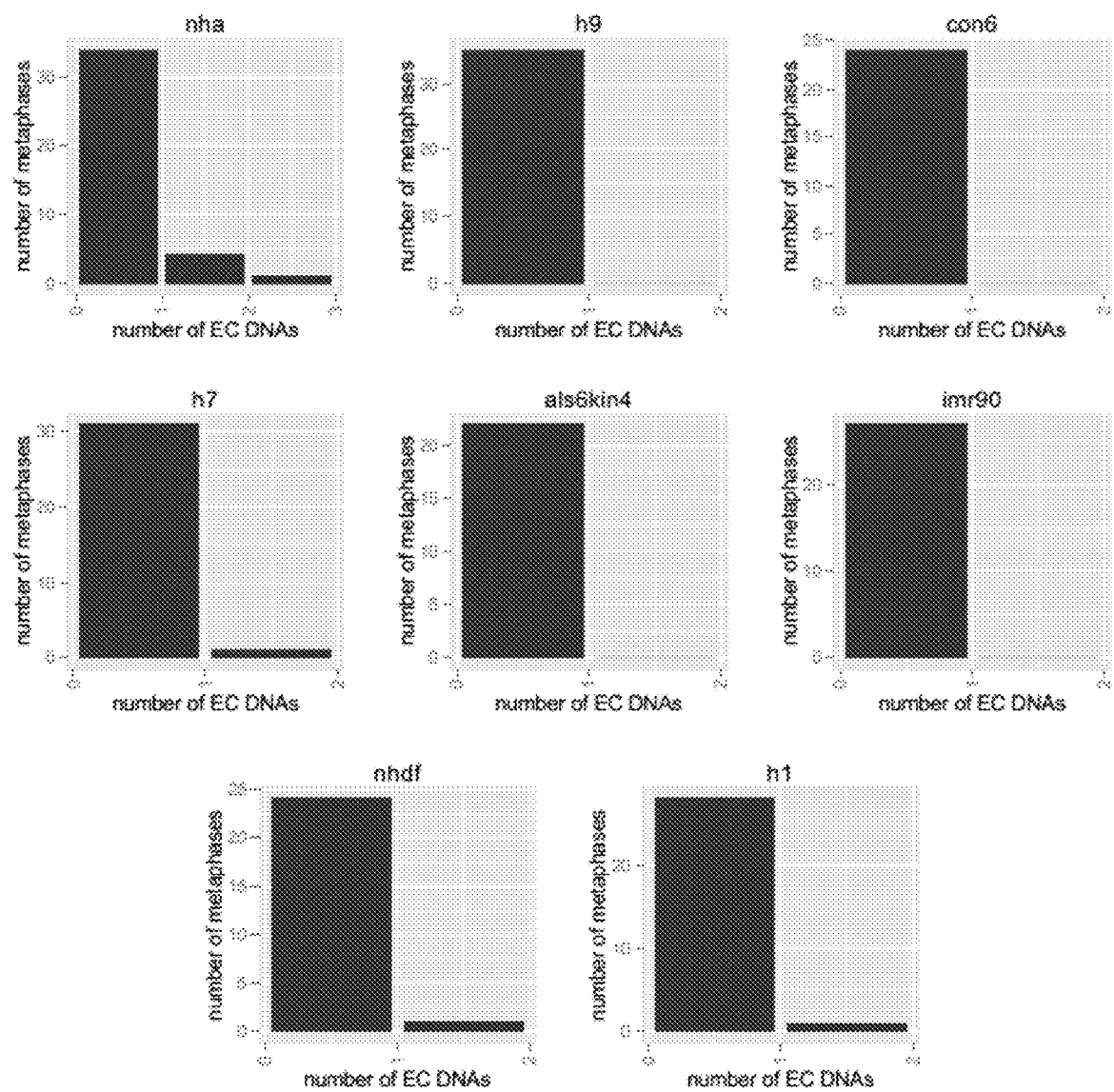
FIG. 20. The figure shows ECDNA count histograms of normal samples.
Figure 21:
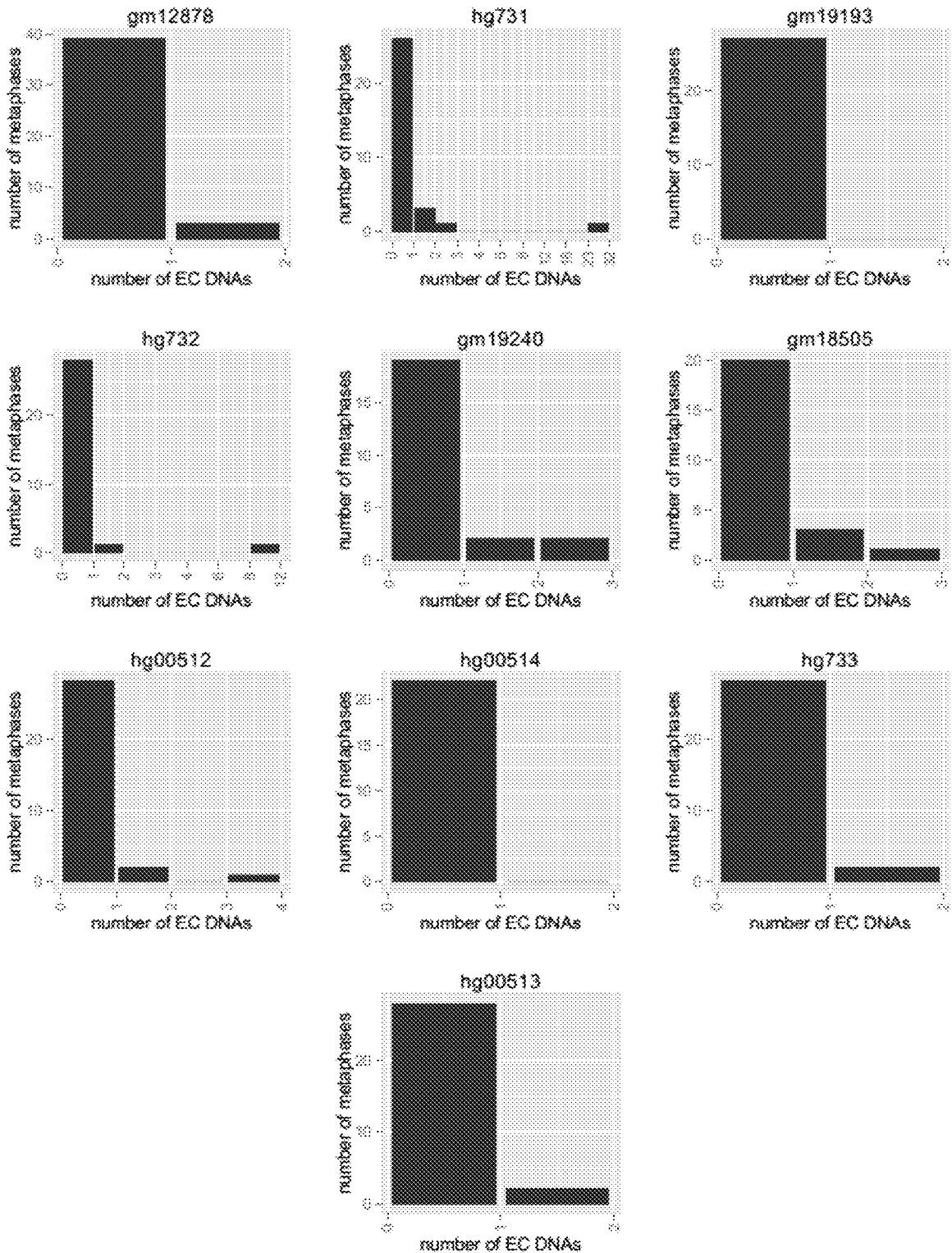
FIG. 21. The figure shows ECDNA count histograms of immortalized samples.
Figure 22:
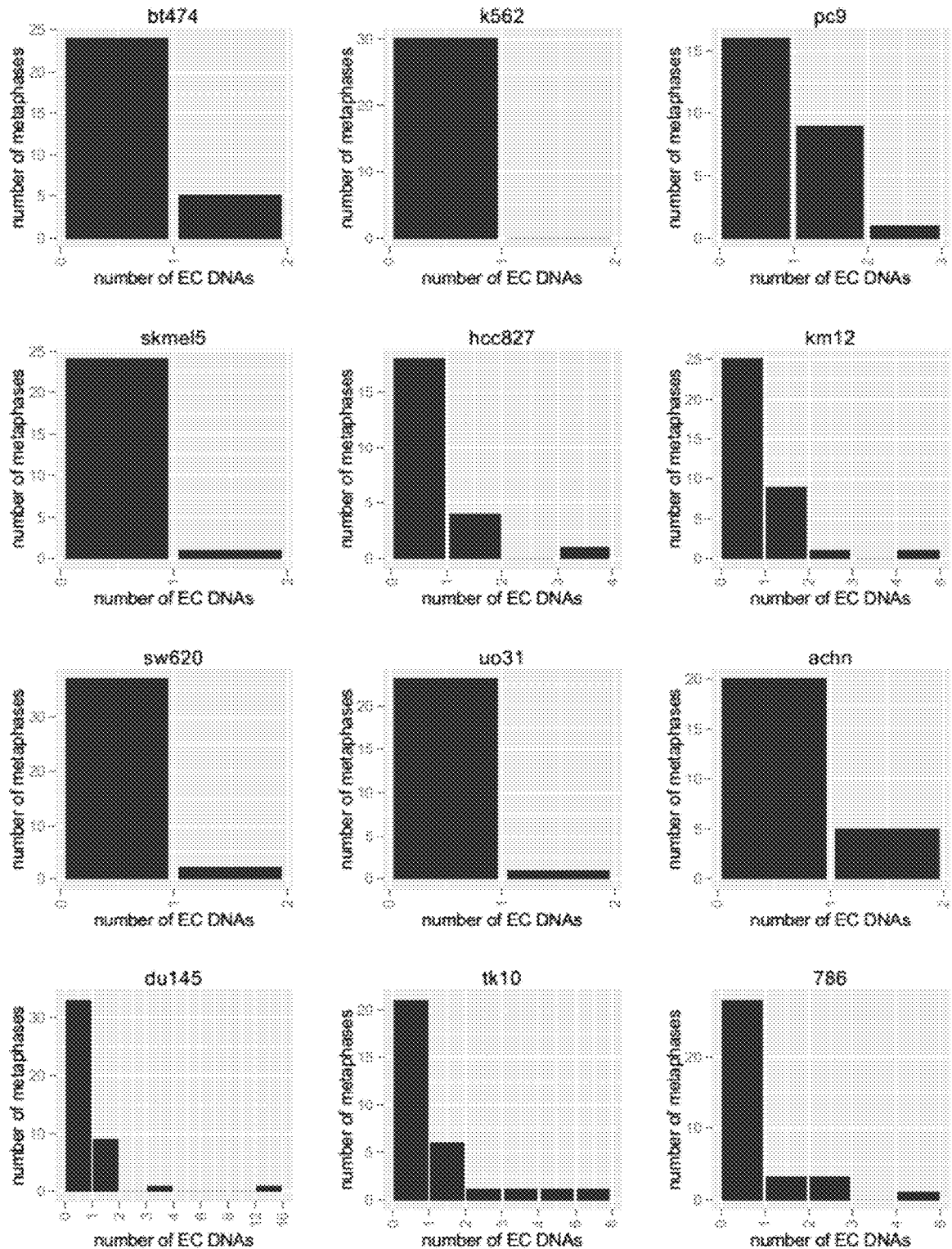
FIG. 22. The figure shows ECDNA count histograms of tumor cell line samples.

Comparison of software vs. visual inspection. The ECDNA coordinates detected by the software and selected by manual marking are com-pared and they are accepted to match if the distance between them is no more than 7 pixels. A sample comparison result is shown in FIG. 19F.

Section 2.3 Results.

Figure 1F:
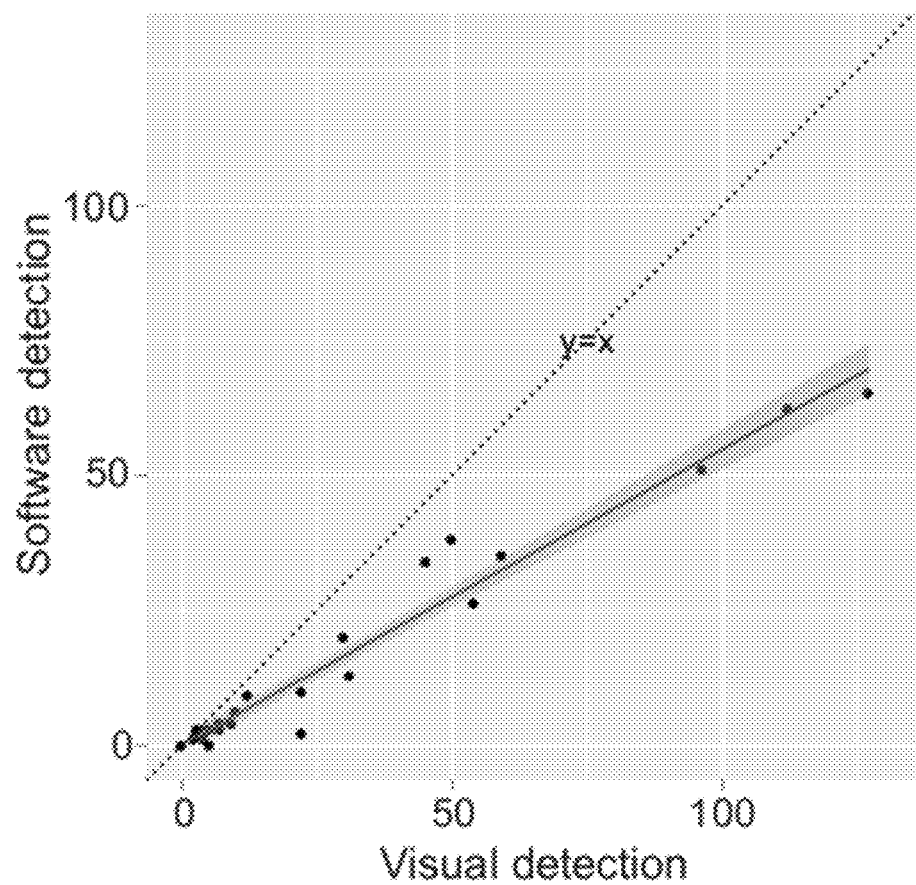

We arbitrarily chose 28 images, in which we could confidently mark the ECDNA, while also aiming for a large range of ECDNA count across images, from various different tumor cell lines for purposes of robustness. We evaluated the performance of the ECDNA detection software by comparing it with manual ECDNA marking on the aforementioned 28 DAPI metaphase images from various tumor cell lines with varying count of ECDNAs. The comparison results are shown in FIGS. 19A-19F for representative examples. Out of 406 detected ECDNA, 392 of them (97%) agreed with manually marked ECDNAs, however among the 737 total manually marked ECDNAs, the software missed 345 of them, resulting in a under-estimation by 53%. We would like to emphasize, however, that it was by design to discard the regions at the immediate neighborhood of non-ECDNA structures, e.g. chromosomal regions, from the ECDNA search ROI and undercall ECDNAs in order not to accept any questionable structure as extrachromosomal DNA. Indeed, 88% of the ECDNAs missed by the software compared to manual marking resides in the aforementioned discarded region. The software provides a conservative estimate of the total ECDNA signal; it achieves high precision at the expense of sensitivity compared to visual inspection, which may also have imperfections. FIG. 1F shows the high correlation (Pearson; r=0.98, P<2.2×10$^{-16}$) achieved between the ECDNA counts detected by the software and manual marking, suggesting a balanced undercalling of ECDNAs across images, and a reliable estimation for correlative studies. ECDNA count histograms analyzed by ECdetect are shown in FIGS. 19A-19F. Applicants further analyzed ECDNA count histograms for the following cell lines: TK10-030, SF295-002, CAKI1-005, CAKI1-004, Hs578T-009, IGROV1-036, H23-037, U251-041, UACC62-001, 786-0-037, SkMel2-24, SKOV3-019, RXF623-001, BT549-031, CAKI1-014, H322M-023, PC3-006, HK301-016, UACC62-022, BT549-053, HOP62-038, and PC3-003 (data not shown).

Section 3: AmpliconArchitect: Sequence Analysis for Identification and Reconstruction of Focal Amplifications.

For the purpose of the AMPLICON ARCHITECT software, we focused on a set of genomic intervals that are simultaneously amplified to a high copy number. We define a focal amplification or an amplicon as a set of genomic intervals that are amplified to a high copy number, such that the intervals may be either contiguous or discontiguous on the reference genome, but are connected in the tumor cells in circular or linear structures. Different cells may contain different combinations of these genomic elements, and as long as they share common segments, we consider them as one amplicon in a sample. While we do not distinguish between the terms focal amplifications and amplicons, we do separate these events from aneuploidies where large chromosomal scale segments are amplified.

Using cytogenetic (mainly FISH) analysis, we can observe the existence of focal amplifications of the probed regions. By using multiple metaphase spreads, we can determine if those probes are amplified extra-chromosomally, intra-chromosomally, or both, and may be able to observe some heterogeneity in terms of size differences. However, cytogenetic analysis is limited to a few cells, does not reveal the fine structure of the amplicons. In contrast, genome sequencing techniques enable us to zoom into the fine-scale structure of genomic variants [37,38], but provide additional complexities due to sampling from a heterogenous mix of amplicons from many cells. For this reason, existing computational tools (mainly tools that allow structural variation, or SV detection) are limited to identification of one or more rearrangement events and do not provide information of the connectivity and architecture of the larger genomic architecture (layout of genomic segments in one or more structures in a heterogenous mixture). We designed and developed AMPLICONARCHITECT to enable the reconstruction of complex rearrangements in cancer amplicons from WGS data. AMPLICONARCHITECT uses pre-processed data from mapped WGS reads, as described below.

Section 3.1 Pre-Processing.

Identification of amplified regions. We mapped whole genome paired-end Illumina reads from each tumor and normal sample to the hg19 (GRCh37) human reference sequence [32] downloaded from the UCSC genome browser site [33]. The BWA software version 0.7.9a was used with default parameters for mapping [34]. We inferred copy number variants from these mapped reads using the ReadDepth CNV software [35] version 0.9.8.4 with parameters FDR=0.05 and overDispersion parameter=1.

Filtering amplicons. We used stringent filtering criteria to select amplified regions from both sequencing and TCGA datasets. In our starting set, we considered only CNV gain segments with copy count >5 for samples from each dataset. We merged segments within 300 kbp of each other into a single region and considered regions >100 kbp in size. We applied 3 criteria to filter amplicons in repetitive/low-copy genomic regions as well as amplified regions reported in normal tissue samples to avoid sequencing and mapping artefacts:

1. Regions amplified in normal samples: Regions which had copy number of >5 in 2 or more normal samples were labelled as uninteresting and extended by 1 Mbp. A high copy region from a tumor sample which overlapped an uninteresting region was required to be at least 2 Mbp in size after the part which overlapped the uninteresting region was trimmed.
2. Repetitive regions: We eliminated segments with average repeat count of >2.5 (5 accounting for diploid genome) in the reference genome. The average reference repeat count of the region was calculated by defining a duke35 score [39, 40] of a genomic region based on Duke35 mappability. The duke35 score for an interval I was defined as $$\text{duke35}(I) = \frac{\sum_{s \in I} (\text{length}(s)/d35(s))}{\text{length}(I)} \quad (3.1)$$

where s refers to each genomic segment defined in the Duke35 file which overlaps our region of interest, length(s) refers to length in base-pairs of the part of segment which overlaps the region and d35(s) refers to the value assigned to the segment in the Duke35 files. 1/d35(s) corresponds to the repeat count of the segment (extended by 34 base-pairs) in the reference genome. Thus regions with duke35(I)≥2.5 were eliminated.

3. Segmental duplication regions: We eliminated the regions of segmental duplications from the human paralog project [11-13] depending on the observed copy counts in our samples. If an interval I overlapped one or more segmental duplications, then the copy count of this interval was revised as the $$\text{NewCount}(I) = \frac{\text{OriginalCount}(I) \cdot \text{length}(I)}{\text{length}(I) + \sum \text{length(overlapping segmental duplications)}} \quad (3.2)$$

Only regions which had a revised copy count >5 were retained.

Section 3.2 Reconstructing Amplicon Architecture Using AmpliconArchitect.

For each sample, AMPLICONARCHITECT(AA) takes as input, an initial list of amplified intervals and whole genome sequencing (WGS) paired-end reads aligned to the human reference. The high level steps in AA are as follows:

1. Identify boundaries of segments in the reference genome that are part of the amplicon.
2. Build a breakpoint graph with nodes corresponding to segment-endpoints, and edges connecting pairs of nodes. The pairs may be from the same or different segments.
3. Use an optimization to estimate copy numbers of edges.
4. Extract paths and cycles in the graph that explain most of the copy number. These paths and cycles correspond to putative amplicon structures.

These steps are expanded upon below.

Sequencing statistics. AMPLICONARCHITECT samples a random subset of paired-end WGS reads to estimate sequencing parameters like read length, insert size, depth of coverage, and variability in coverage. We also estimate percentage of read pairs mapping concordantly (in the expected size and orientation). and expected number of read pairs that map across a genomic location. This expected number of read pairs within 3 standard deviations is used to identify clusters of discordant read pairs that indicate a genomic rearrangement.

Detecting segment boundaries. We used two genomic signatures that suggest segment boundaries, as well as connections: 1) Discordant read pair clusters: Recall that a genomic rearrangement can be indicated by a set of discordantly mapping read pair [37,38]. The coordinates where the two reads map also provide the boundary of the segment, and indicate that the two segments are connected in the tumor genome. We used clusters of reads supporting the same rearrangement to identify segment boundaries as well as interconnections. We used filtering strategies based on the Duke35 mappability score described above to minimize false signals for rearrangements. 2) Meanshift in coverage: Segment boundaries were also detected by a steep copy number change between adjacent or nearby locations. We used a mean-shift technique used in image processing for edge detection [43]. Specifically, we used a smoothed Gaussian kernel density function for coverage to find a span of genomic coordinates with similar values followed by a second span with different kernel density values (See also [44]). The locations determined to have shift in coverage were further investigated for rearrangements using discordant read clusters with less stringent criteria e.g., fewer number (~3) of read pairs.

Breakpoint graph construction. Segment boundaries represent vertices in the breakpoint graph. Consecutive vertices that represented the beginning and end of a segment along the genome were connected by sequence-edges. Vertices linked by discordant read-pair clusters were connected using breakpoint-edges. We also used breakpoint edges to connect the end of one segment to the beginning of an adjacent segment. We introduced a special source vertex to represent ends of linear contigs or unidentified connections. A breakpoint edge was used to connect an existing vertex and the source vertex if we observed one-end mapping reads on the vertex, under the assumption that it represented an undiscovered rearrangement because one of the end-points was located in repetitive or novel/mutated sequence.

Copy count determination. We assigned edge weights proportional to the number of reads mapping to each sequence-edge and breakpoint-edge. Assuming that shotgun reads follow a Poisson process, we formulated and optimized an objective function to normalize raw read counts into estimated copy counts for all edges of the breakpoint graph.

Paths and cycles in the graph that have a uniform copy number on all edges correspond to an amplified genomic sequence in the tumor genome. Given that the breakpoint graph represents the union of all of these amplifications, we obtain linear constraints on the copy numbers. The linear constraint (balanced-flow constraint) enforces that copy counts for breakpoint-edges incident at a breakpoint vertex should sum up to the copy count of the sequence-edge connected to the vertex. The optimized counts represent edge-weights in the breakpoint graph.

Figure 29:
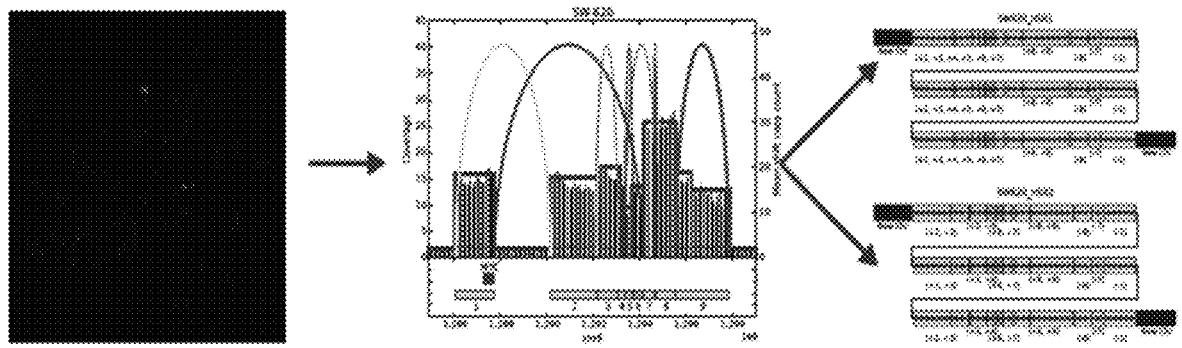
FIG. 29. The figure shows fine structure analysis of c-MYC Amplification in Chromosomal DNA in Sw620 Colon Cancer Cells.

Amplicon Architecture determination. We processed the edge-weighted breakpoint graph and extracted cycles. Cycles containing the source vertex represent paths beginning and ending at the two vertices adjacent to the source. The balanced-flow constraint ensures that we can always decompose the breakpoint graph into cycles and linear contigs such that the copy counts of edges in the subgraphs add up to the copy counts in the original graph. We used a polynomial-time heuristic which iteratively identifies the most dominant cycle or path, i.e. the cycle or path with the highest copy count until 80% of the genomic content in the breakpoint graph was accounted for in the extracted cycles. We note that the short insert lengths do not always allow an unambiguous and complete reconstruction of the amplified segment. However, the cycles provide a 'basis' decomposition, and cycles with common sequence-edges may be combined in multiple ways to form larger cycles to explore the full architecture and heterogeneity in the amplicon. An example of such a basis decomposition's corresponding fine structure interpretation and visualization is presented in FIG. 29.

Section 3.3 Results.

We sequenced 117 tumor samples including 63 cell lines, 19 neurospheres (PDX) and 35 cancer tissues with coverage ranging from 0.6× to 3.89×, excluding one sample with 0.06× coverage. See Extended Data Figure E4 for the coverage distribution across samples. We also sequenced additional 8 normal tissues as controls.

While the sequencing depth is low, it is sufficient to capture large regions with increased copy number. Consider the lowest mean coverage in our samples c=0.6. For a region of size w (w=$10^5$ in our tests), and copy count d, the expected number of 100 bp reads with diploid genome $$\lambda = \frac{wcd}{100 \cdot 2} = \frac{10^5 \cdot 0.6d}{200} = 150d$$

We assume the Null hypothesis that the number of reads in the region is Poisson distributed with parameter $\lambda$. Our goal is to exclude all regions with normal copy count, while including all regions with high copy numbers (e.g. d≥6). Consider an experiment where we select all regions of size w, containing at least 750 mapped reads. Then, the probability of a Type I error (including a region with copy count 2) is given by $$1.0 - \text{Poisson-}cdf(750, \lambda=300) \approx 0.0$$

The probability of a Type II error (missing a region with d≥6) is at most $$\text{Poisson-}cdf(750, \lambda=900) = 1.5 \cdot 10^{-7}$$

The numbers are better for samples with higher sequence coverage, and larger amplified regions.

We identified 265 high-copy amplifications in 61 samples (see methods section 3.1). We analyzed putative genomic connections between amplified regions to identify amplicon structures consisting of 1 or more amplified regions. The amplifications were assembled in 183 independent amplicons with copy count ranging from 2.64 to 132.11 and size ranging from 111 Kbp to 67 Mbp.

In order to estimate the significance of our observations, we downloaded copy number variation calls for 11079 tumor-normal samples covering 33 different tumor types from TCGA [45]. After merging and filtering the variant calls according to our criterion in Section 3.1, we identified 16408 amplicons in 3919 samples.

For each dataset, genome sequencing and TCGA, we computed a histogram for percentage of samples displaying an amplification at each genomic position. The weight in the histogram for samples in the genome sequencing dataset was adjusted to reflect the frequency of corresponding tumor types in TCGA samples. We found 20 peak regions amplified in more than 1% of TCGA samples. We compared these regions against 522 oncogenes from the COSMIC database (August 2014) [46] 13 out 20 regions contained an oncogene. We observed that 17 out of 20 regions were also captured by amplifications reported from our sequencing dataset, including all 13 oncogene regions most of each were amplified in multiple samples.

Figure 30:
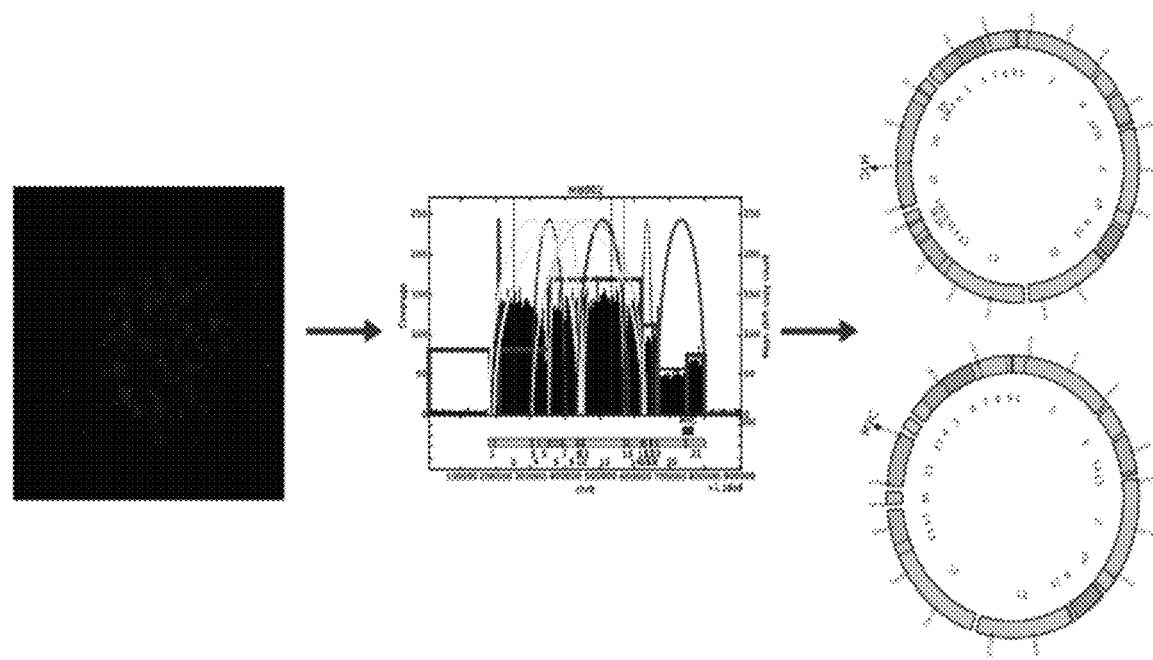
FIG. 30. The figure shows fine structure analysis of c-MYC Amplification in Extrachromosomal DNA in Medulloblastoma MB002 Cells.
Figure 31:
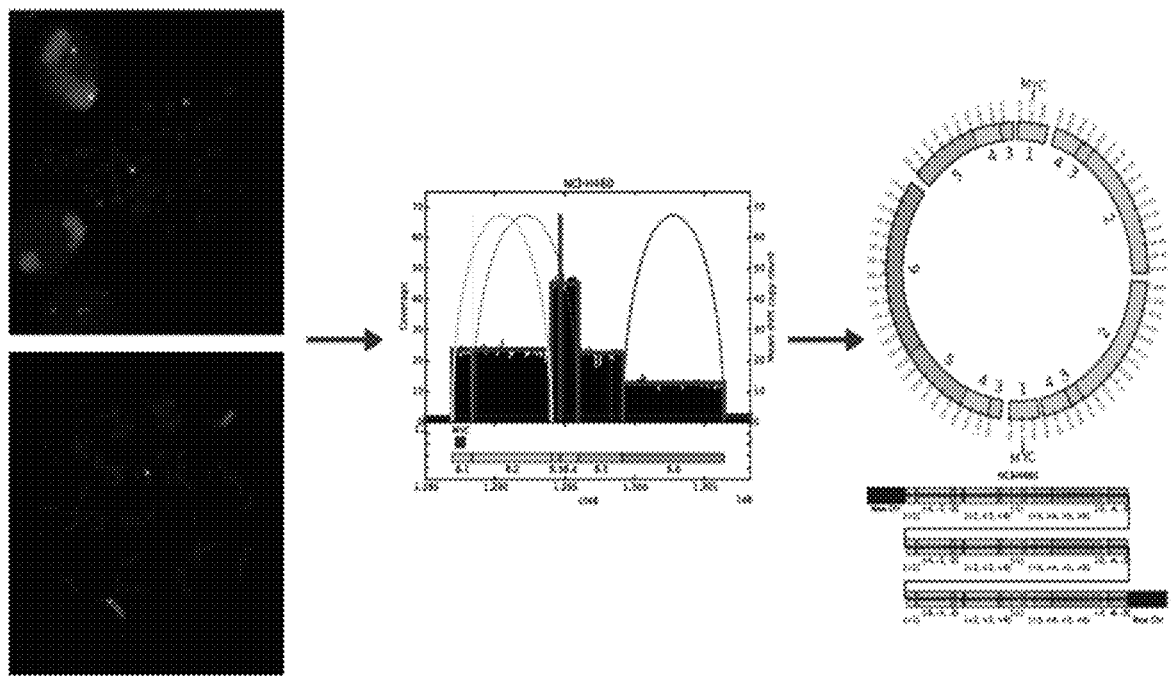
FIG. 31. The figure shows fine structure analysis of c-MYC Amplification in Extrachromosomal and Chromosomal DNA in NCI H460 Non-Small Cell Lung Cancer Cells.
Figure 32:
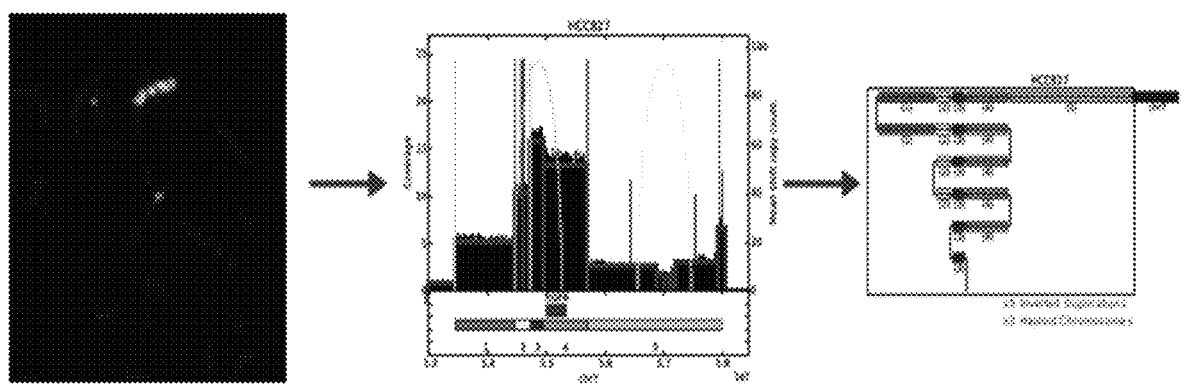
FIG. 32. The figure shows fine structure analysis of EGFR Amplification in Chromosomal DNA via Breakage-Fusion-Bridge (BFB) mechanism in HCC827 Lung Adenocarcinoma Cells displays inverted duplications.
Figures 33A, 33B, 33C, 33D, 33E:
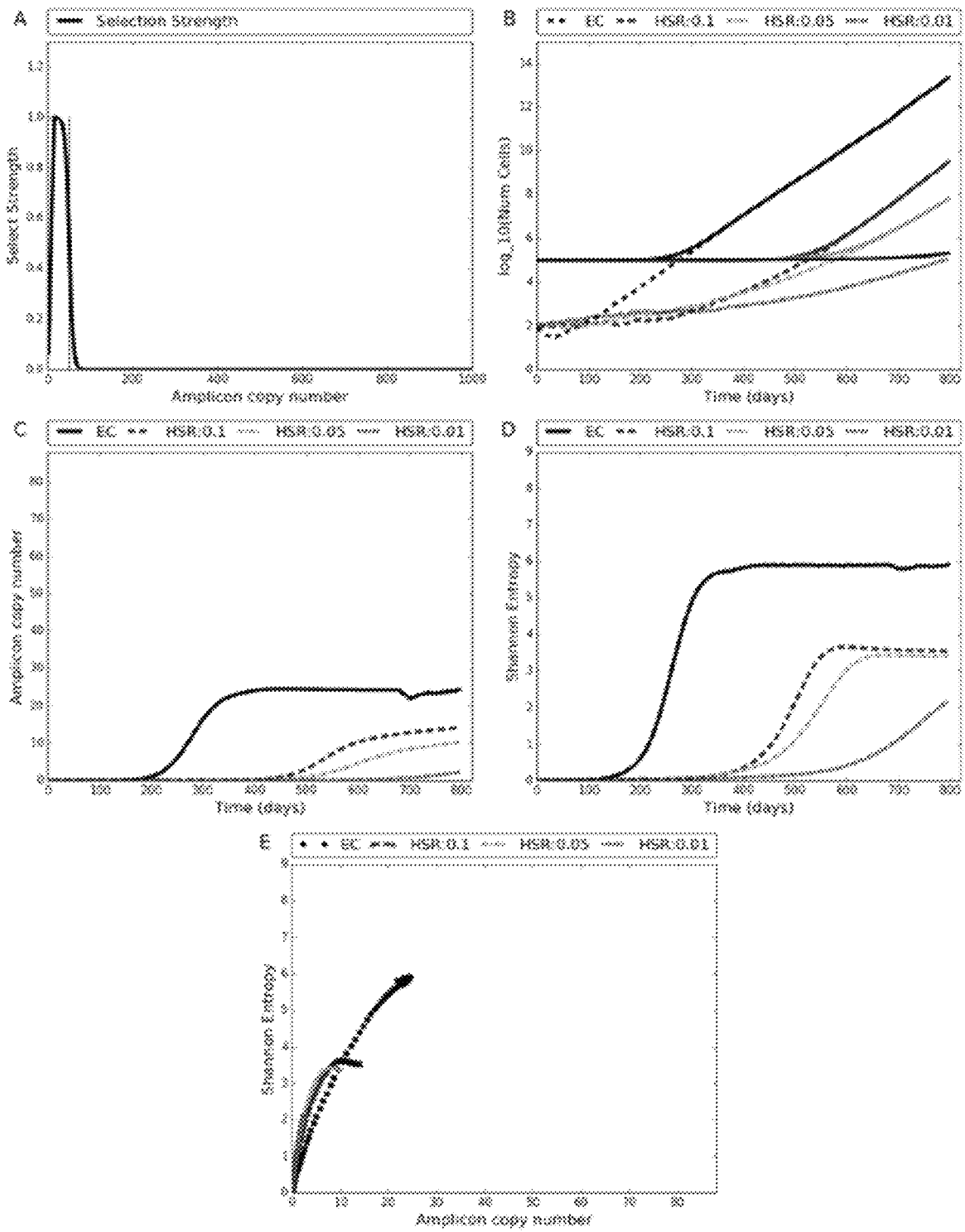
FIGS. 33A-33E. The figures show evolution of tumor amplicons, with Initial Population $N_0=10^5$, selection-coefficient s=0.5, decay parameter m=50. 33A: The selection function $f_m(k)$ with m=50. The ratio of birth to death rate for a cell with k amplicon copies is given by $1+sf_m(k)$. 33B: Growth of cells over time with EC amplicon compared to growth with intrachromosomal amplification (HSR) with duplication probabilities 0.1; 0.05; 0.01. The dotted lines represent the number of cells containing amplicons, starting with 100 amplicon containing cells, while solid lines depict the total number of cells in the population. 33C: Increase in the amplicon copy number per cell over time. 33D: Change in Shannon entropy of the number of amplicons per cell with time. 33E: Change in entropy compared to change in copy number.
Figures 34A, 34B, 34C, 34D, 34E:
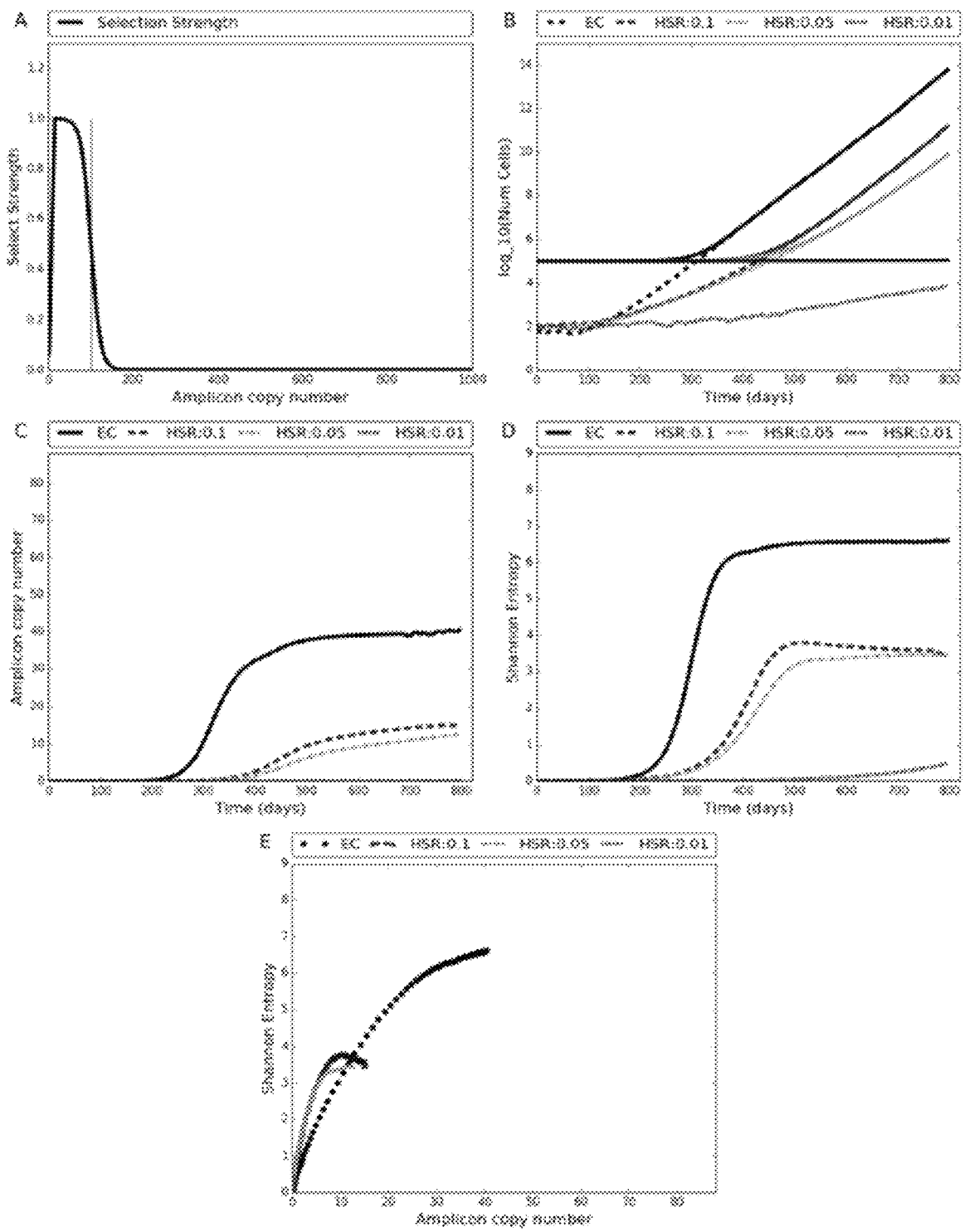
FIGS. 34A-34E. The figures show tumor evolution with $N_0=10^5$, s=0.5, m=100. 34A: The selection function $f_{100}(k)$. The ratio of birth to death rate for a cell with k amplicon copies is given by $1+sf_m(k)$. 34B: Growth of cells over time with EC amplicon compared to growth with intrachromosomal amplification (HSR) with duplication probabilities 0.1; 0.05; 0.01. The dotted lines represent the number of cells containing amplicons, starting with 100 amplicon containing cells, while solid lines depict the total number of cells in the population. 34C: Increase in the amplicon copy number per cell over time. 34D: Change in Shannon entropy of the number of amplicons per cell with time. 34E: Change in entropy compared to change in copy number.
Figures 35A, 35B, 35C, 35D, 35E:
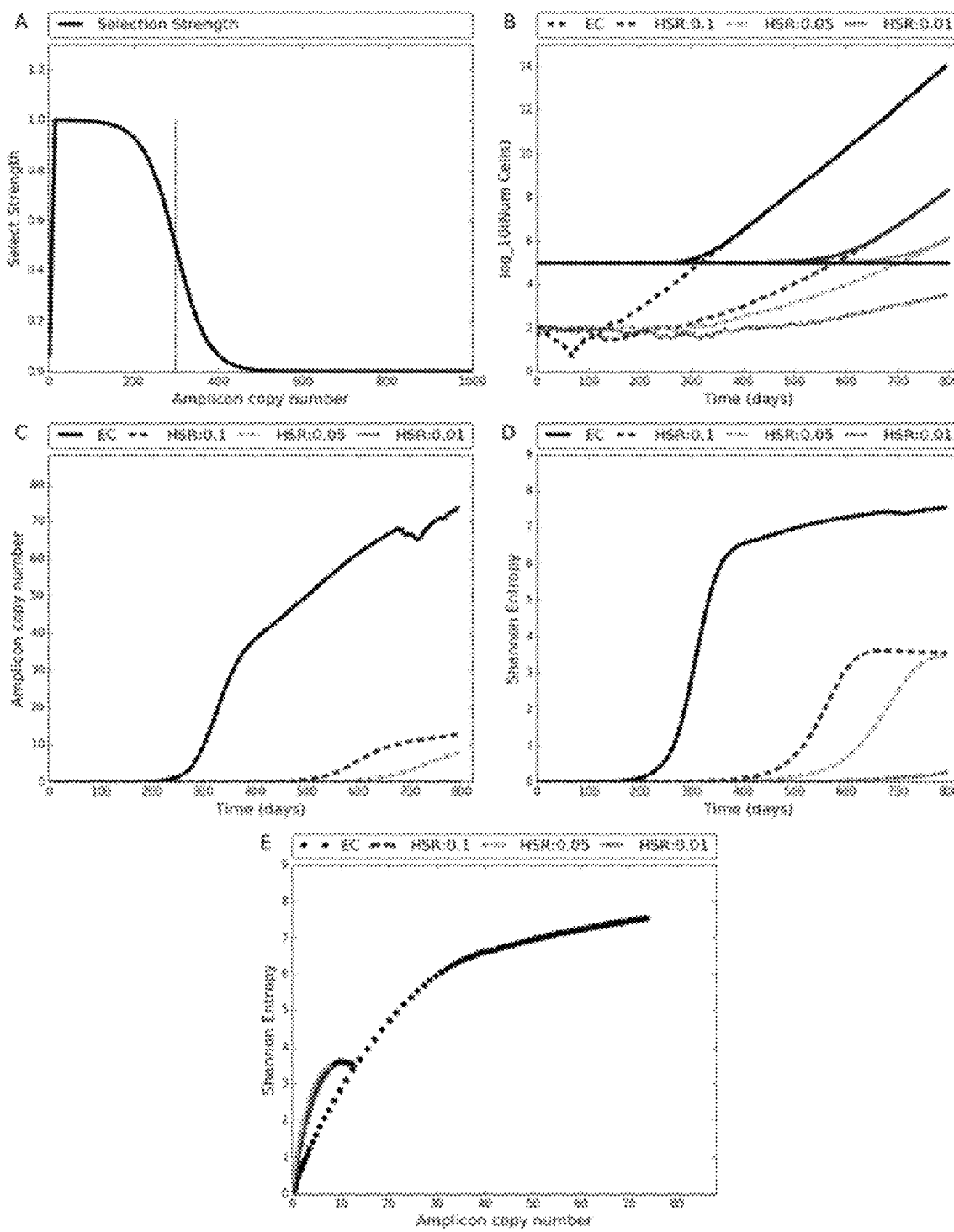
FIGS. 35A-35E. The figures show tumor evolution with $N_0=10^5$, s=0.5, m=300. 35A: The selection function $f_{300}(i)$. The ratio of birth to death rate for a cell with k amplicon copies is given by $1+sf_m(k)$. 35B: Growth of cells over time with EC amplicon compared to growth with intrachromosomal amplification (HSR) with duplication probabilities 0.1; 0.05; 0.01. The dotted lines represent the number of cells containing amplicons, starting with 100 amplicon containing cells, while solid lines depict the total number of cells in the population. 35C: Increase in the amplicon copy number per cell over time. 35D: Change in Shannon entropy of the number of amplicons per cell with time. 35E: Change in entropy compared to change in copy number.
Figures 36A, 36B, 36C, 36D, 36E:
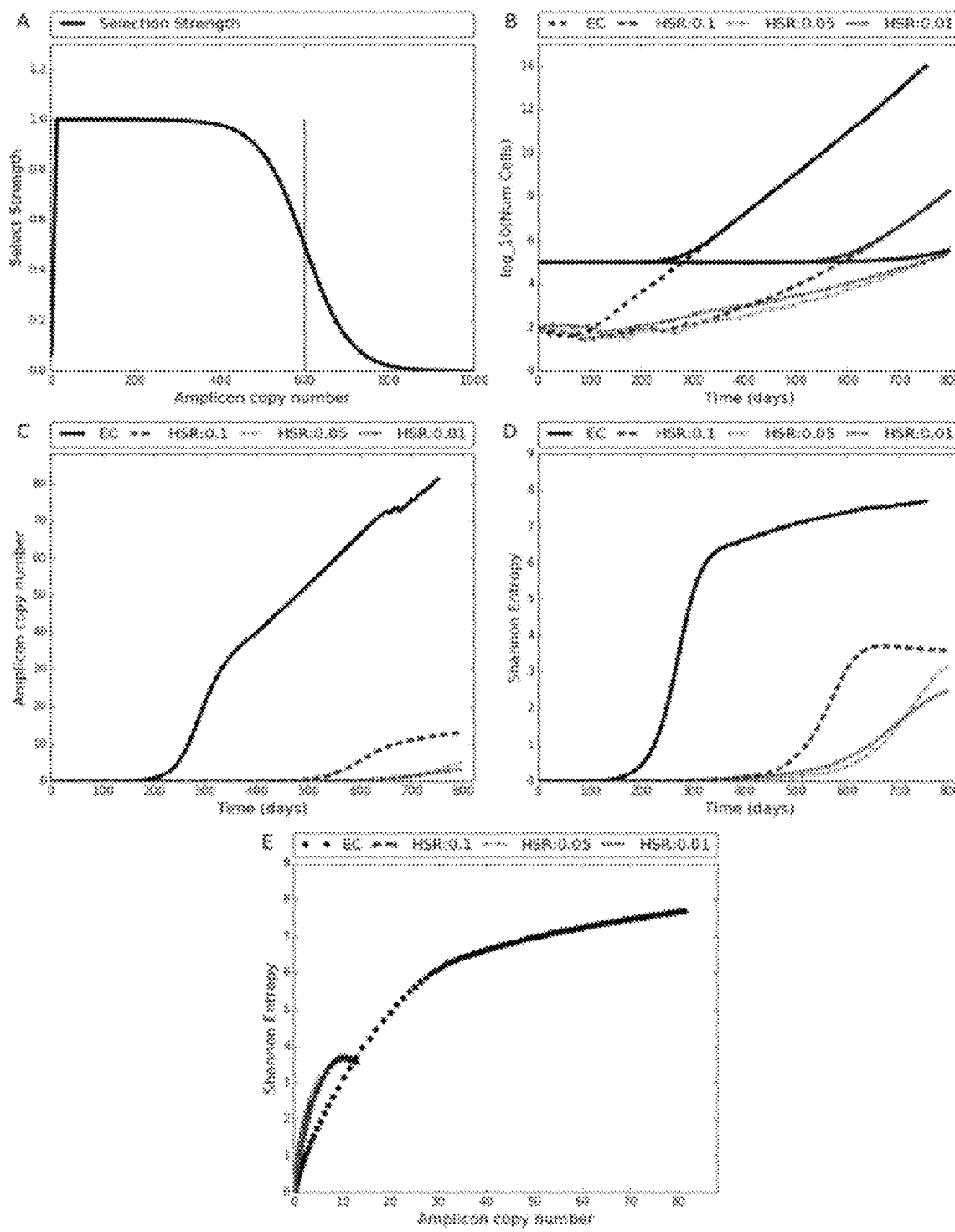
FIGS. 36A-36E. The figures show tumor evolution with $N_0=10^5$, s=0.5, m=600. 36A: The selection function f600(k). The ratio of birth to death rate for a cell with k amplicon copies is given by $1+sf_m(k)$. 36B: Growth of cells over time with EC amplicon compared to growth with intrachromosomal amplification (HSR) with duplication probabilities 0.1; 0.05; 0.01. The dotted lines represent the number of cells containing amplicons, starting with 100 amplicon containing cells, while solid lines depict the total number of cells in the population. 36C: Increase in the amplicon copy number per cell over time. 36D: Change in Shannon entropy of the number of amplicons per cell with time. 36E: Change in entropy compared to change in copy number.
Figures 37A, 37B, 37C, 37D, 37E:
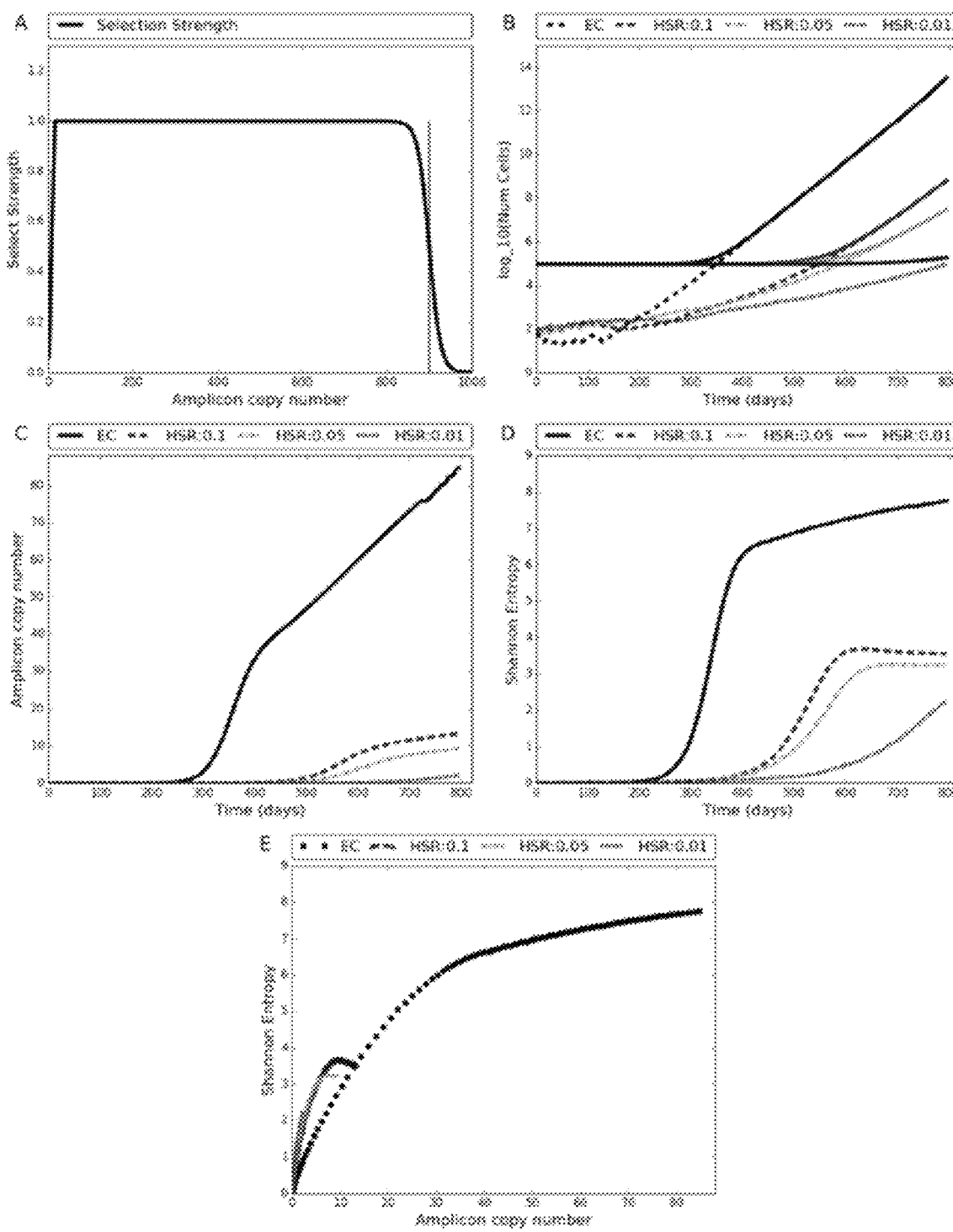
FIGS. 37A-37E. The figures show tumor evolution with $N_0=10^5$, s=0.5, m=900. 37A: The selection function $f_{900}(k)$. The ratio of birth to death rate for a cell with k amplicon copies is given by $1+sf_m(k)$. 37B: Growth of cells over time with EC amplicon compared to growth with intrachromosomal amplification (HSR) with duplication probabilities 0.1; 0.05; 0.01. The dotted lines represent the number of cells containing amplicons, starting with 100 amplicon containing cells, while solid lines depict the total number of cells in the population. 37C: Increase in average amplicon copy number over time. 37D: Change in Shannon entropy with time. 37E: Change in entropy compared to change in copy number.
Figures 38A, 38B, 38C, 38D, 38E:
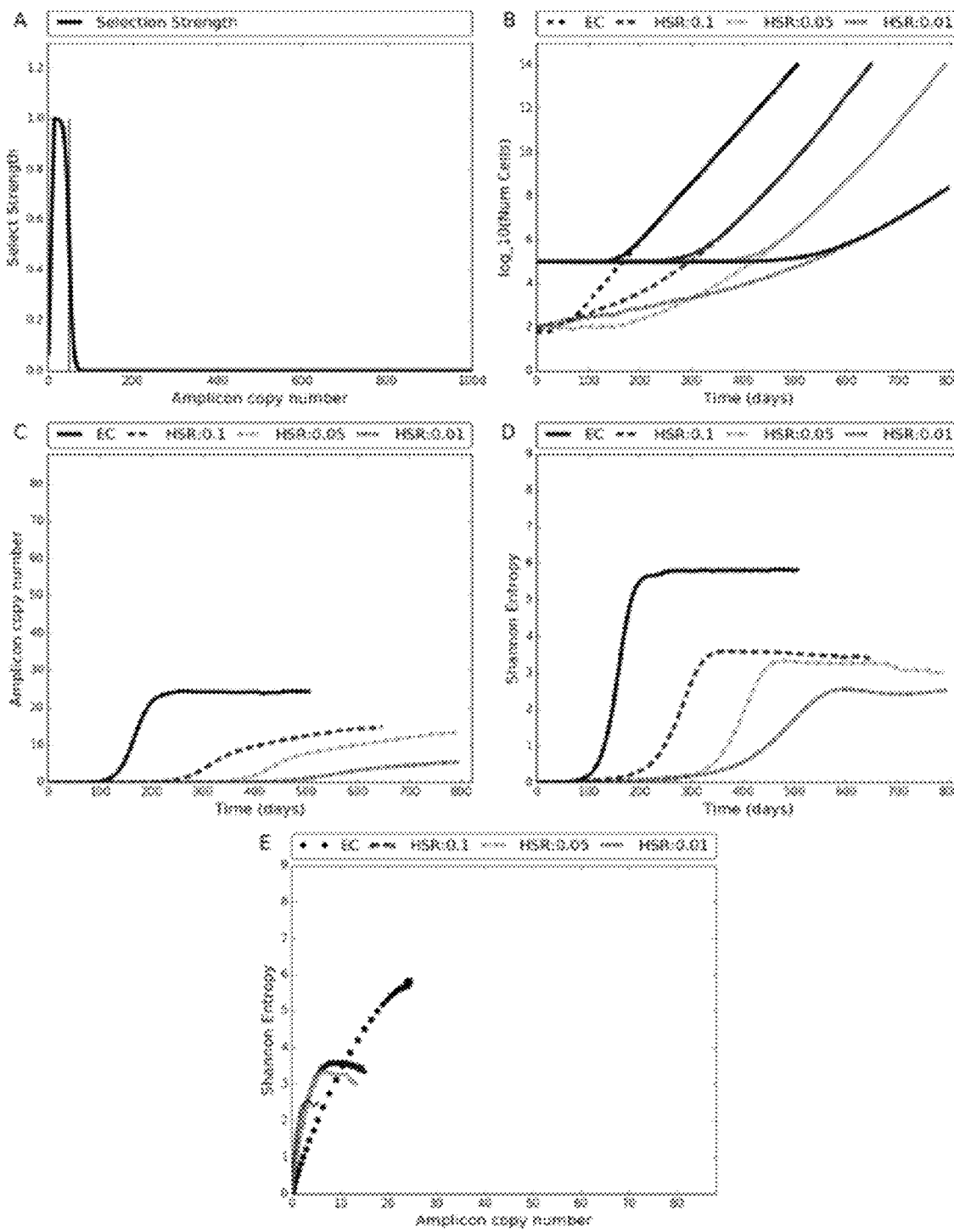
FIGS. 38A-38E. The figures show tumor evolution with $N_0=10^5$, s=1.0, m=50. 38A: The selection function $f_{50}(k)$. The ratio of birth to death rate for a cell with k amplicon copies is given by $1+sf_m(k)$. 38B: Growth of cells over time with EC amplicon compared to growth with intrachromosomal amplification (HSR) with duplication probabilities 0.1; 0.05; 0.01. The dotted lines represent the number of cells containing amplicons, starting with 100 amplicon containing cells, while solid lines depict the total number of cells in the population. 38C: Increase in average amplicon copy number over time. 38D: Change in Shannon entropy with time. 38E: Change in entropy compared to change in copy number.
Figures 39A, 39B, 39C, 39D, 39E:
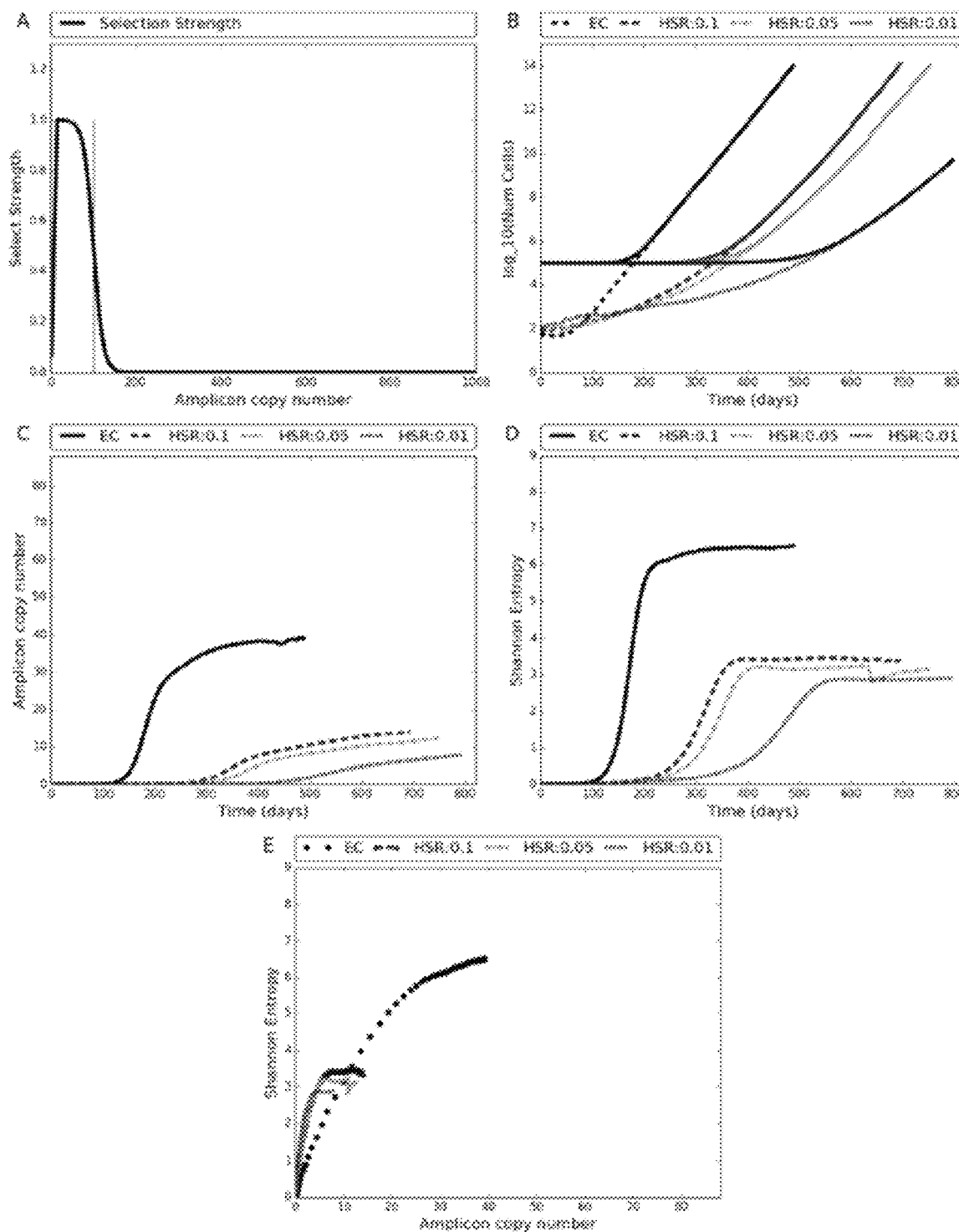
FIGS. 39A-39E. The figures show tumor evolution with $N_0=10^5$, s=1.0, m=100. 39A: The selection function $f_{100}(k)$.
Figures 40A, 40B, 40C, 40D, 40E:
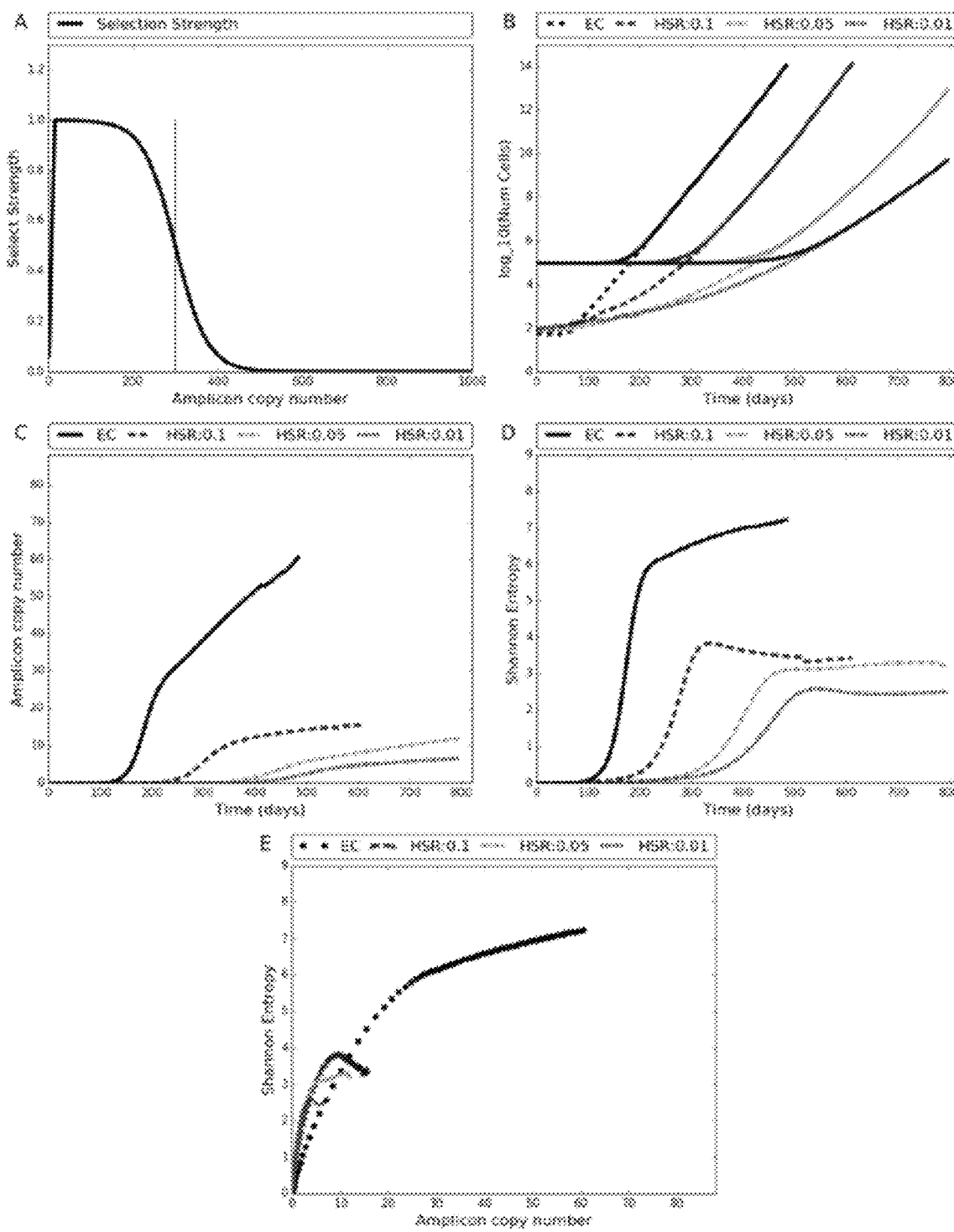
Figures 41A, 41B, 41C, 41D, 41E:
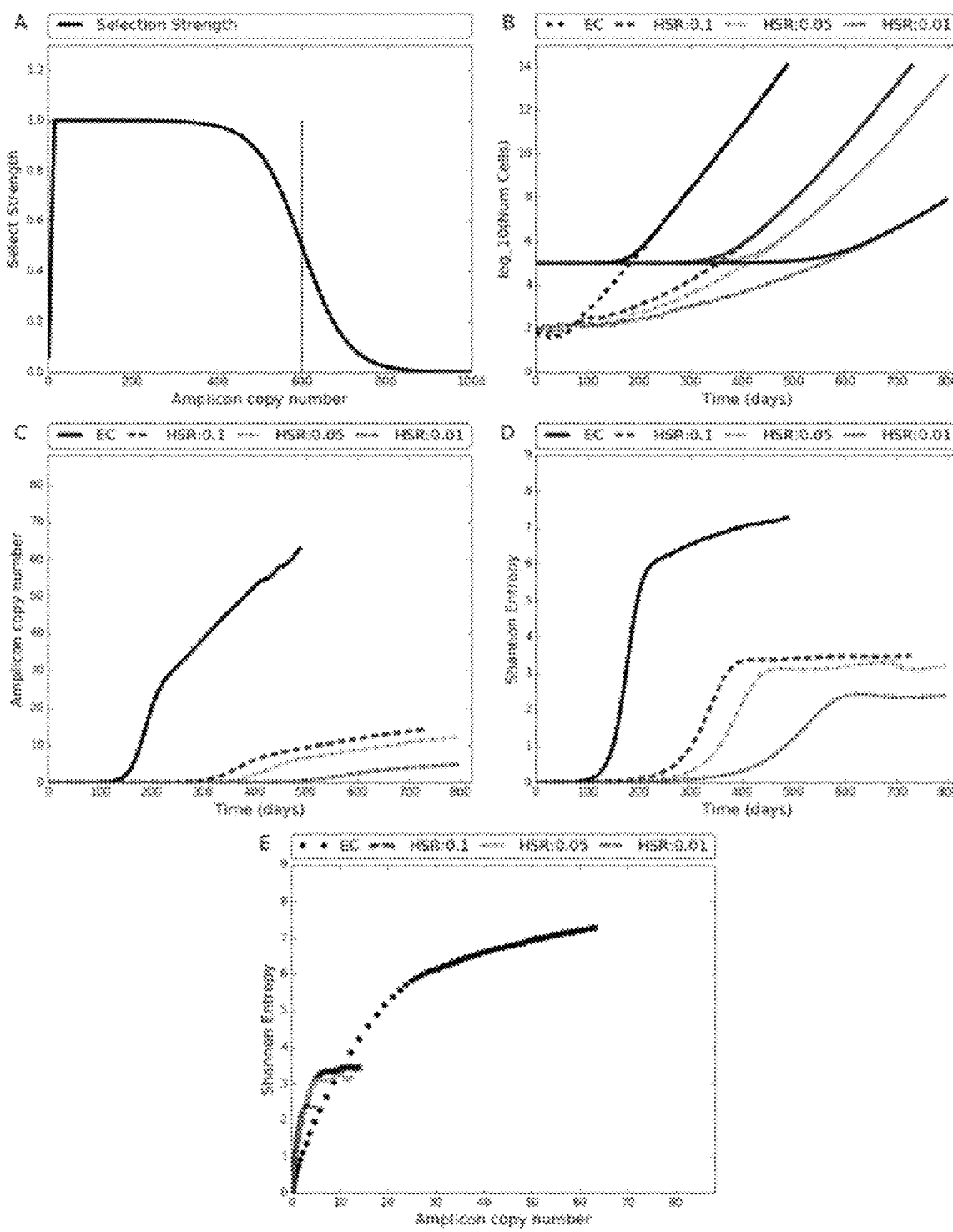
Figures 42A, 42B, 42C, 42D:
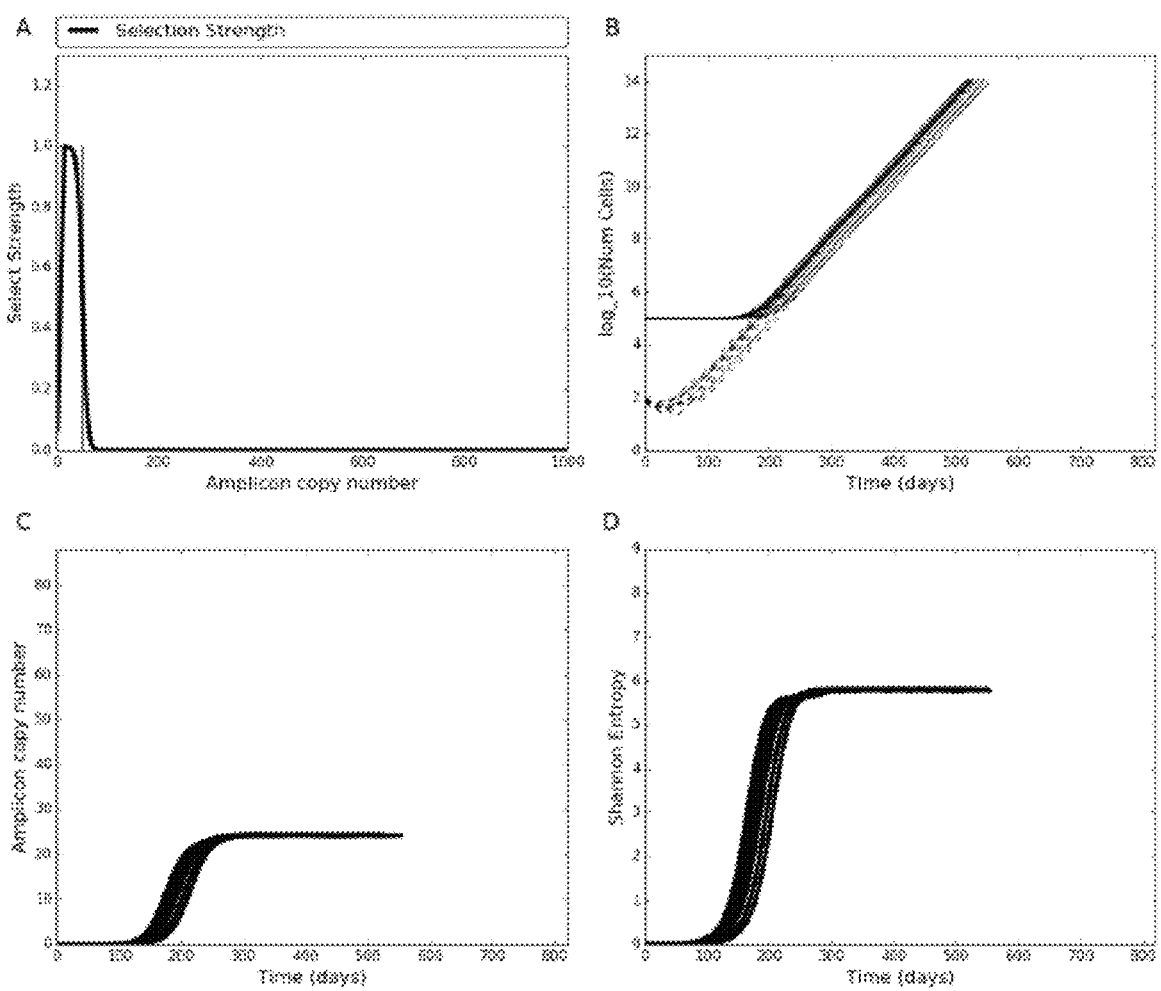

The genome sequencing samples displayed a wide variety of amplicon structures ranging from a simple circularization of a single genomic segment to mixtures of multiple structures (Sw620-MYC FIG. 29), amplicons containing complex rearrangements (MB002-MYC FIG. 30), similar structure simultaneously in EC and HSR (H460-MYC FIG. 31), multiple connected genomic regions. We identified one instance of a Breakage Fusion Bridge (HCC827-EGFR FIG. 32). FISH analysis revealed that some of these amplicons occurred as ECDNAs, HSRs or sometimes both, in the same sample. Many amplicons could be represented as cycles or closed walks on the breakpoint graph indicative of either circular ECDNAs or tandemly duplicated HSRs. For many amplicons, most of the copy count could be explained by one or only a few cycles/walks indicating that the copies of amplificons consisted of a single or mixture of only a few distinct structures arising from a common origin.

Section 4: A Theoretical Model of Extrachromosomal and Intrachromosomal Duplication.

Section 4.1 Model.

Consider an initial population of $N_0$ cells, of which $N_a$ cells contain a single extra copy of an oncogene. We model the population using a discrete generation Galton-Watson branching process [47]. In this simplified model, each cell in the current generation containing k ampli-cons (amplifying an oncogene) either dies with probability $d_k$, or replicates with probability $b_k$ to create the next generation. We set the selective advantage $$\frac{b_k}{d_k} = \begin{cases} 1 + s f_m(k), & 0 \le k < M_a \\ 0 & \text{otherwise} \end{cases} \quad (4.1)$$

$$d_k = 1 - b_k \quad (4.2)$$

In other words, cells with k copies of the amplicon stop dividing after reaching a limit of $M_a$ amplicons. Otherwise, they have a selective advantage for $0 < k \le M_a$, where the strength of selection is described by $f_m(k)$, as follows:

$$f_m(k) = \begin{cases} \dfrac{k}{M} & (0 \le k \le M_s), \\ \dfrac{1}{1 + e^{-a(k-m)}} & (M_s < k < M_a). \end{cases} \quad (4.3)$$

Here, s denotes the selection-coefficient, and parameters m and a are the 'mid-point', and 'steepness' parameters of the logistic function, respectively. Initially, $f_m(k)$ grows linearly, reaching a peak value of $f_m(k)=1$ for $k=M_s$. As the viability of cells with large number of amplicons is limited by available nutrition [48], $f_m(k)$ decreases logistically in value for $k>M_s$ reaching $f_m(k) \to 0$ for $k \ge M_a$. We model the decrease by a sigmoid function with a single mid-point parameter m s.t. $f_m(m) = \frac{1}{2}$. The 'steepness' parameter a is automatically adjusted to ensure that max $\{1-f_m(M_s), f_m(M_a)\} \to 0$.

The copy number change is effected by different mechanisms for extrachromosomal (EC) and intrachromosomal (HSR) models. In the EC model, the available k amplicons are on EC elements which replicate and segregate independently. We assume complete replication of EC elements so that there are 2 k copies which are partitioned into the two daughter cells via independent segregation. Formally, the daughter cells end up with $k_1$ and $k_2$ amplicons respectively, where $$k_1 \sim B(2k, \tfrac{1}{2}) \quad (4.4)$$

$$k_2 = 2k - k_1 \quad (4.5)$$

In contrast, in the intrachromosomal model, the change in copy number happens via mitotic recombination, and the daughter cell of a cell with k amplicons will acquire either k+1 amplicons or k−1 amplicons, each with probability $p_d$. With probability $1-2p_d$, the daughter cell retains k amplicons.

Section 4.2 Model Parameters.

We started with an initial population $N_0=10^5$ and a small number of cells ($N_a=100$) with one extra copy of an amplicon. We set $M_s=15$, $M_a=10^3$ for both, based on the observation of cells with ~$10^3$ EC elements (e.g. Extended Data Figure E10). While the number is excessive for intrachromosomal amplifications, we kept $M_s$, $M_a$ identical for both EC and intrachromosomal events to allow for direct comparisons. It is well known that tumor cells have a selective advantage and proliferate; the rates are however different for different tumors and also within a sample, as cells acquiring multiple oncogenic mutations quickly grow more aggressively [47]. We chose different values of s {0.5, 1.0} to explore different growth rates. For s=0.5, $$\frac{b_k}{d_k} \le 1.5,$$

implying a tumor growth rate of $b_k-d_k=2b_k-1=0.2$ per generation. For s=1, $$\frac{b_k}{d_k} \le 2$$

implying a growth rate of 0.33 per generation. The results are not substantially different across different choices of s, with impact only on the rate of amplification and heterogeneity. While these choices provide maximum growth rate, the choice of the selection function $f_m(k)$ reduces the growth rate with increasing number of amplicons to model the effect of excessive metabolic demands on the cell. Once a cell reaches $M_a=1000$, it stops replicating. The decay in selection function is modeled by a single parameter m, denoting the number of amplicon copies at which the selection strength is half of the peak strength.

Exponential growth of amplicon containing cells is seen in both extrachromosomal and in-trachromosomal duplications. However, the tumor mass cannot grow indefinitely. We model the tumor as a sphere, and assume that $10^9$ cells account for a tumor of 1 cm diameter [49] although more recent accounts put the number for tumor cells as $10^8$ $cm^{-3}$ [50]. A physical limit of 20 cm for the tumor diameter [51] implies a limit of $10^{13}$ tumor cells. We stop the simulation once the number of tumor cells reach $10^{14}$. Note that more realistic models have been proposed where growth rate depends upon spatial constraints (e.g., see [52]). Tumors are modeled as spheres, but can only replicate on the surface of the sphere, or when there is dispersion of the tumor cells. Here, we work with the simpler model to focus on the differences between extrachromosomal and intrachromosomal methods of amplification.

In summary, the main difference in the two models is in the differing mechanisms for amplification. For intrachromosomal model, we experimented with different duplication probabilities ($0.01 \leq HSR \leq 0.1$). We chose a generation time of 3 days to measure time in days.

Section 4.3 Results.

FIGS. 33-37 give the results for s=0.5, while FIGS. 38-41 show the results for s=1.0. For each choice of s, the different figures vary only in the mid-point of the logistic decay of the selection function (parameter m), which models the metabolic constraints.

The results are consistent in all cases. We see an exponential growth in the overall cell population, as well as in cells containing amplicons (FIGS. 33-42). The amplicon containing cells take some time to establish, and then grow exponentially (Panel A in Figures). The rate of growth depends upon selection coefficient (s), and metabolic constraints (m). Our model is somewhat simplified as in most real situations, the growth does not continue indefinitely, but stabilizes due to spatial and metabolic constraints. We model metabolic constraints, but not spatial, in order to keep the model simple and to focus on the differences between extrachromosomal and intrachromosomal amplification.

The copy number of the amplicon (average number of copies per cell) grows for all cases, but the growth is slower for intrachromosomal compared to extrachromosomal (Panel B in all Figures). Similar behavior is observed for the number of amplicons per cell (Panel C in all Figures), and heterogeneity of copy number, measured as the Shannon entropy of the copy number distribution of amplicons (Panel D in all Figures). We note that when the metabolic constraints are weak (high values of m), heterogeneity and average number of amplicons per cell continue to grow. However, for stringent metabolic constraints, both heterogeneity and number of amplicons per cell stabilize, and even decrease, consistent with some long term studies [53].

Figure 4F:
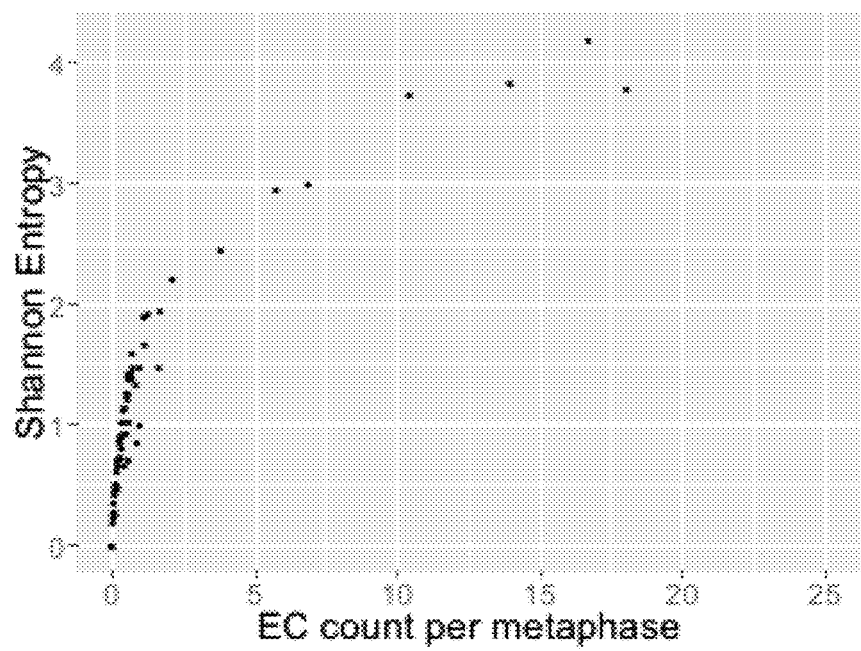

Finally, heterogeneity grows along with copy number, but stabilizes (Panel E in all Figures). These model predictions are robust to choice of model parameters, and are borne out by experimental observations (FIG. 4F).

FIG. 42 shows the variance in trajectories in 10 simulation runs. We note that much of the variance comes from the fact that the amplicon containing cells take some time to establish, or reach their maximum growth rate. This time to establishment varies due from experiment to experiment due to the stochastic nature of the experiment. Otherwise, the results are consistent from run to run. As there can be a significant time gap between the establishment of cells, we did not compute the variance in number of cells between runs, but showed each trajectory separately.

EMBODIMENTS

Embodiment P1. An extrachromosomal nucleic acid protein complex comprising an extrachromosomal cancer-specific nucleic acid bound to an endonuclease through an extrachromosomal cancer-specific nucleic acid binding RNA.

Embodiment P2. The extrachromosomal nucleic acid protein complex of embodiment P1, wherein said extrachromosomal cancer-specific nucleic acid is an oncogene nucleic acid.

Embodiment P3. The extrachromosomal nucleic acid protein complex of embodiment P1, wherein said extrachromosomal cancer-specific nucleic acid is a non-essential gene nucleic acid.

Embodiment P4. The extrachromosomal nucleic acid protein complex of embodiment P1, wherein said extrachromosomal cancer-specific nucleic acid is an intragenic nucleic acid sequence.

Embodiment P5. The extrachromosomal nucleic acid protein complex of embodiment P1, wherein said extrachromosomal cancer-specific nucleic acid is a junction nucleic acid sequence.

Embodiment P6. The extrachromosomal cancer-specific nucleic acid of any one of embodiments P1-P5, wherein said extrachromosomal cancer-specific nucleic acid is amplified.

Embodiment P7. The extrachromosomal nucleic acid protein complex of any one of embodiments P1-P6, wherein said endonuclease is a CRISPR associated protein 9 (Cas9), a CxxC finger protein 1(Cpf1), or a Class II CRISPR endonuclease.

Embodiment P8. The extrachromosomal nucleic acid protein complex of any one of embodiments P1-P7, wherein said extrachromosomal cancer-specific nucleic acid binding RNA is at least in part complementary to said extrachromosomal cancer-specific nucleic acid.

Embodiment P9. The extrachromosomal nucleic acid protein complex of any one of embodiments P1-P8, wherein said extrachromosomal nucleic acid protein complex forms part of a cell.

Embodiment P10. The extrachromosomal nucleic acid protein complex of embodiment P9, wherein said cell is a cancer cell.

Embodiment P11. The extrachromosomal nucleic acid protein complex of embodiment P10, wherein said cancer cell comprises an extrachromosomal gene amplification.

Embodiment P12. A method of treating cancer in a subject in need thereof, said method comprising delivering to said subject a therapeutically effective amount of an extrachromosomal cancer-specific nucleic acid binding RNA and an endonuclease, thereby treating cancer in said subject.

Embodiment P13. The method of embodiment P12, wherein said cancer comprises an extrachromosomal gene amplification.

Embodiment P14. A method for inducing apoptosis in a cancer cell, said method comprising: (i) contacting a cancer cell with an effective amount of an extrachromosomal cancer-specific nucleic acid binding RNA bound to an endonuclease; (ii) allowing said extrachromosomal cancer-specific nucleic acid binding RNA to hybridize to an extrachromosomal cancer-specific nucleic acid, thereby binding said endonuclease to said extrachromosomal cancer-specific nucleic acid; and (iii) allowing said endonuclease to cleave said extrachromosomal cancer-specific nucleic acid, thereby inducing apoptosis in said cancer cell.

Embodiment Z1. A method of treating cancer in a patient in need thereof, the method comprising: (i) obtaining a biological sample from a patient; (ii) detecting oncogene amplification on circular extrachromosomal DNA in the biological sample; (iii) administering a therapeutically effective amount of an anti-cancer drug to the patient to treat the cancer when oncogene amplification on the circular extrachromosomal DNA is detected in the biological sample.

Embodiment Z2. The method of embodiment Z1, further comprising measuring the genetic heterogeneity of the circular extrachromosomal DNA.

Embodiment Z3. The method of embodiment Z1 or Z2, further comprising mapping the circular extrachromosomal DNA.

Embodiment Z4. The method of any one of embodiments Z1 to Z3, further comprising repeating steps (i) and (ii) to monitor changes in the oncogene amplification on the circular extrachromosomal DNA throughout the cancer treatment.

Embodiment Z5. The method of any one of embodiments Z1 to Z4, wherein the biological sample is a tumor, blood, or a tumor fluid.

Embodiment Z6. The method of any one of embodiments Z1 to Z5, wherein the oncogene is EGFR, c-Myc, N-Myc, cyclin D1, ErbB2, CDK4, CDK6, BRAF, MDM2, or MDM4.

Embodiment 1. A method of detecting an amplified extrachromosomal oncogene in a human subject in need thereof, said method comprising: (i) obtaining a biological sample from a human subject; (ii) detecting whether an amplified extrachromosomal oncogene is present in said sample by contacting said biological sample with an oncogene-binding agent and detecting binding between said amplified extrachromosomal oncogene and said oncogene-binding agent.

Embodiment 2. The method of embodiment 1, wherein said amplified extrachromosomal oncogene forms part of a circular extrachromosomal DNA.

Embodiment 3. The method of embodiment 2, wherein said detecting comprises detecting an intracellular location of said amplified extrachromosomal oncogene relative to a standard control.

Embodiment 4. The method of embodiment 3, wherein said detecting comprises detecting a level of said circular extrachromosomal DNA relative to a standard control.

Embodiment 5. The method of embodiment 4, wherein said detecting comprises mapping said circular extrachromosomal DNA.

Embodiment 6. The method of embodiment 5, wherein said detecting comprises detecting genetic heterogeneity of said circular extrachromosomal DNA relative to a standard control.

Embodiment 7. The method of embodiment 6, wherein said amplified extrachromosomal oncogene is EGFR, c-Myc, N-Myc, cyclin D1, ErbB2, CDK4, CDK6, BRAF, MDM2, or MDM4.

Embodiment 8. The method of embodiment 7, wherein said is oncogene-binding agent is a labeled nucleic acid probe.

Embodiment 9. The method of embodiment 1, wherein said biological sample is a blood-derived biological sample, a urine-derived biological sample, a tumor sample, or a tumor fluid sample.

Embodiment 10. The method of embodiment 1, further comprising selecting a subject that has or is at risk for developing cancer.

Embodiment 11. The method of embodiment 1, further comprising administering to said subject an effective amount of an anti-cancer agent.

Embodiment 12. A method of treating cancer in a subject in need thereof, said method comprising: (i) obtaining a biological sample from a human subject; (ii) detecting whether an amplified extrachromosomal oncogene is present in said sample by contacting said biological sample with an oncogene-binding agent and detecting binding between said amplified extrachromosomal oncogene and said oncogene-binding agent; and (iii) administering to said human subject an effective amount of an anti-cancer agent.

Embodiment 13. The method of embodiment 12, wherein said amplified extrachromosomal oncogene forms part of a circular extrachromosomal DNA.

Embodiment 14. The method of embodiment 13, wherein said detecting comprises detecting an intracellular location of said amplified extrachromosomal oncogene relative to a standard control.

Embodiment 15. The method of embodiment 14, wherein said detecting comprises detecting a level of said circular extrachromosomal DNA relative to a standard control.

Embodiment 16. The method of embodiment 15, wherein said detecting comprises mapping said circular extrachromosomal DNA.

Embodiment 17. The method of embodiment 16, wherein said detecting comprises detecting genetic heterogeneity of said circular extrachromosomal DNA relative to a standard control.

Embodiment 18. The method of embodiment 17, wherein said amplified extrachromosomal oncogene is EGFR, c-Myc, N-Myc, cyclin D1, ErbB2, CDK4, CDK6, BRAF, MDM2, or MDM4.

Embodiment 19. The method of embodiment 18, wherein said is oncogene-binding agent is a labeled nucleic acid probe.

Embodiment 20. The method of embodiment 12, wherein said biological sample is a blood-derived biological sample, a urine-derived biological sample, a tumor sample, or a tumor fluid sample.

Embodiment 21. The method of embodiment 20, wherein said anti-cancer agent is a peptide, small molecule, nucleic acid, antibody or aptamer.

Embodiment 22. A method of detecting an amplified extrachromosomal oncogene in a cancer subject undergoing treatment for cancer, said method comprising: (i) obtaining a first biological sample from said cancer subject undergoing treatment for cancer; and (ii) detecting in said first biological sample a first level of an amplified extrachromosomal oncogene.

Embodiment 23. The method of embodiment 22, comprising after step (ii): (iii) obtaining a second biological sample from said subject; (iv) detecting a second level of said amplified extrachromosomal oncogene; and (v) comparing said first level to said second level.

Embodiment 24. The method of embodiment 23, wherein said first biological sample from said subject is obtained at a time $t_0$, and said second biological sample from said subject is obtained at a later time $t_1$.

Embodiment 25. The method of embodiment 22, wherein said amplified extrachromosomal oncogene forms part of a circular extrachromosomal DNA.

Embodiment 26. The method of embodiment 25, wherein said detecting comprises detecting an intracellular location of said amplified extrachromosomal oncogene relative to a standard control.

Embodiment 27. The method of embodiment 26, wherein said detecting comprises detecting a level of said circular extrachromosomal DNA relative to a standard control.

Embodiment 28. The method of embodiment 27, wherein said detecting comprises mapping said circular extrachromosomal DNA.

Embodiment 29. The method of embodiment 28, wherein said detecting comprises detecting genetic heterogeneity of said circular extrachromosomal DNA relative to a standard control.

Embodiment 30. The method of embodiment 29, wherein said amplified extrachromosomal oncogene is EGFR, c-Myc, N-Myc, cyclin D1, ErbB2, CDK4, CDK6, BRAF, MDM2, or MDM4.

Embodiment 31. The method of embodiment 30, wherein said is oncogene-binding agent is a labeled nucleic acid probe.

Embodiment 32. The method of embodiment 22, wherein said biological sample is a blood-derived biological sample, a urine-derived biological sample, a tumor sample, or a tumor fluid sample.

Embodiment 33. The method of embodiment 22, further comprising administering to said subject an effective amount of an anti-cancer agent.

Embodiment 34. An extrachromosomal nucleic acid protein complex comprising an extrachromosomal cancer-specific nucleic acid bound to an endonuclease through an extrachromosomal cancer-specific nucleic acid binding RNA.

Embodiment 35. The extrachromosomal nucleic acid protein complex of embodiment 34, wherein said extrachromosomal cancer-specific nucleic acid is an oncogene nucleic acid.

Embodiment 36. The extrachromosomal nucleic acid protein complex of embodiment 34, wherein said extrachromosomal cancer-specific nucleic acid is a non-essential gene nucleic acid.

Embodiment 37. The extrachromosomal nucleic acid protein complex of embodiment 34, wherein said extrachromosomal cancer-specific nucleic acid is an intragenic nucleic acid sequence.

Embodiment 38. The extrachromosomal nucleic acid protein complex of embodiment 34, wherein said extrachromosomal cancer-specific nucleic acid is a junction nucleic acid sequence.

Embodiment 39. The extrachromosomal cancer-specific nucleic acid of any one of embodiments 34-38, wherein said extrachromosomal cancer-specific nucleic acid is an amplified extrachromosomal cancer-specific nucleic acid.

Embodiment 40. The extrachromosomal nucleic acid protein complex of any one of embodiments 34-39, wherein said endonuclease is a CRISPR associated protein 9 (Cas9), a CxxC finger protein 1(Cpf1), or a Class II CRISPR endonuclease.

Embodiment 41. The extrachromosomal nucleic acid protein complex of any one of embodiments 34-40, wherein said extrachromosomal cancer-specific nucleic acid binding RNA is at least in part complementary to said extrachromosomal cancer-specific nucleic acid.

Embodiment 42. The extrachromosomal nucleic acid protein complex of any one of embodiments 34-41, wherein said extrachromosomal nucleic acid protein complex forms part of a cell.

Embodiment 43. The extrachromosomal nucleic acid protein complex of embodiment 42, wherein said cell is a cancer cell.

Embodiment 44. The extrachromosomal nucleic acid protein complex of embodiment 43, wherein said cancer cell comprises an amplified extrachromosomal oncogene.

Embodiment 45. A method of treating cancer in a subject in need thereof, said method comprising delivering to said subject a therapeutically effective amount of an extrachromosomal cancer-specific nucleic acid binding RNA and an endonuclease, thereby treating cancer in said subject.

Embodiment 46. The method of embodiment 45, wherein said cancer comprises an amplified extrachromosomal oncogene.

Embodiment 47. A method for inducing apoptosis in a cancer cell, said method comprising: (i) contacting a cancer cell with an effective amount of an extrachromosomal cancer-specific nucleic acid binding RNA bound to an endonuclease; (ii) allowing said extrachromosomal cancer-specific nucleic acid binding RNA to hybridize to an extrachromosomal cancer-specific nucleic acid, thereby binding said endonuclease to said extrachromosomal cancer-specific nucleic acid; and (iii) allowing said endonuclease to cleave said extrachromosomal cancer-specific nucleic acid, thereby inducing apoptosis in said cancer cell.

REFERENCES

1. Vogelstein, B. et al. Cancer genome landscapes. Science 339, 1546-1558, doi:10.1126/science.1235122 (2013).
2. Stark, G. R., Debatisse, M., Giulotto, E. & Wahl, G. M. Recent progress in understanding mechanisms of mammalian DNA amplification. Cell 57, 901-908 (1989).
3. Schimke, R. T. Gene amplification in cultured animal cells. Cell 37, 705-713 (1984).
4. Fan, Y. et al. Frequency of double minute chromosomes and combined cytogenetic abnormalities and their characteristics. J Appl Genet 52, 53-59, doi:10.1007/s13353-010-0007-z (2011).
5. Nowell, P. C. The clonal evolution of tumor cell populations. Science 194, 23-28 (1976).
6. McGranahan, N. & Swanton, C. Biological and therapeutic impact of intratumor heterogeneity in cancer evolution. Cancer Cell 27, 15-26, doi:10.1016/j.ccell.2014.12.001 (2015).
7. Marusyk, A., Almendro, V. & Polyak, K. Intra-tumour heterogeneity: a looking glass for cancer? Nat Rev Cancer 12, 323-334, doi:10.1038/nrc3261 (2012).
8. Yates, L. R. & Campbell, P. J. Evolution of the cancer genome. Nat Rev Genet 13, 795-806, doi:10.1038/nrg3317 (2012).
9. Greaves, M. & Maley, C. C. Clonal evolution in cancer. Nature 481, 306-313, doi:10.1038/nature10762 (2012).
10. Andor, N. et al. Pan-cancer analysis of the extent and consequences of intratumor heterogeneity. Nat Med 22, 105-113, doi:10.1038/nm.3984 (2016).
11. Gillies, R. J., Verduzco, D. & Gatenby, R. A. Evolutionary dynamics of carcinogenesis and why targeted therapy does not work. Nat Rev Cancer 12, 487-493, doi: 10.1038/nrc3298 (2012).
12. Von Hoff, D. D., Needham-VanDevanter, D. R., Yucel, J., Windle, B. E. & Wahl, G. M. Amplified human MYC oncogenes localized to replicating submicroscopic circular DNA molecules. Proc Natl Acad Sci USA 85, 4804-4808 (1988).
13. Garsed, D. W. et al. The architecture and evolution of cancer neochromosomes. Cancer Cell 26, 653-667, doi: 10.1016/j.ccell.2014.09.010 (2014).
14. Carroll, S. M. et al. Double minute chromosomes can be produced from precursors derived from a chromosomal deletion. Mol Cell Biol 8, 1525-1533 (1988).
15. Windle, B., Draper, B. W., Yin, Y. X., O'Gorman, S. & Wahl, G. M. A central role for chromosome breakage in gene amplification, deletion formation, and amplicon integration. Genes Dev 5, 160-174 (1991).
16. Kanda, T., Otter, M. & Wahl, G. M. Mitotic segregation of viral and cellular acentric extrachromosomal molecules by chromosome tethering. J Cell Sci 114, 49-58 (2001).

17. Mitelman, F., Johansson, B. & Mertens, F. Mitelman Database of Chromosome Aberrations and Gene Fusions in Cancer, <http://cgap.nci.nih.gov/Chromosomes/Mitelman>(2016).
18. Sanborn, J. Z. et al. Double minute chromosomes in glioblastoma multiforme are revealed by precise reconstruction of oncogenic amplicons. Cancer Res 73, 6036-6045, doi:10.1158/0008-5472.CAN-13-0186 (2013).
19. Almendro, V. et al. Inference of tumor evolution during chemotherapy by computational modeling and in situ analysis of genetic and phenotypic cellular diversity. Cell Rep 6, 514-527, doi:10.1016/j.celrep.2013.12.041 (2014).
20. Zack, T. I. et al. Pan-cancer patterns of somatic copy number alteration. Nat Genet 45, 1134-1140, doi:10.1038/ng.2760 (2013).
21. Nathanson, D. A. et al. Targeted therapy resistance mediated by dynamic regulation of extrachromosomal mutant EGFR DNA. Science 343, 72-76, doi:10.1126/science.1241328 (2014).
22. Storlazzi, C. T. et al. Gene amplification as double minutes or homogeneously staining regions in solid tumors: origin and structure. Genome Res 20, 1198-1206, doi:10.1101/gr.106252.110 (2010).
23. Bozic, I. et al. Accumulation of driver and passenger mutations during tumor progression. Proc Natl Acad Sci USA 107, 18545-18550, doi:10.1073/pnas.1010978107 (2010).
24. Li, X. et al. Temporal and spatial evolution of somatic chromosomal alterations: a case-cohort study of Barrett's esophagus. Cancer Prev Res (Phila) 7, 114-127, doi: 10.1158/1940-6207.CAPR-13-0289 (2014).
25. Mishra, S. & Whetstine, J. R. Different Facets of Copy Number Changes: Permanent, Transient, and Adaptive. Mol Cell Biol 36, 1050-1063, doi:10.1128/MCB.00652-15 (2016).
26. Schimke, R. T., Kaufman, R. J., Alt, F. W. & Kellems, R. F. Gene amplification and drug resistance in cultured murine cells. Science 202, 1051-1055 (1978).
27. Nikolaev, S. et al. Extrachromosomal driver mutations in glioblastoma and low-grade glioma. Nat Commun 5, 5690, doi:10.1038/ncomms6690 (2014).
28. Biedler, J. L., Schrecker, A. W. & Hutchison, D. J. Selection of chromosomal variant in amethopterin-resistant sublines of leukemia L1210 with increased levels of dihydrofolate reductase. J Natl Cancer Inst 31, 575-601 (1963).
29. Lee, P. M. Bayesian statistics: an introduction. 4th edn, (John Wiley & Sons, 2012).
30. Motl, J. <https://www.mathworks.com/matlabcentral/fileexchange/40854>
31. Bradley, D. & Roth, G. Adaptive thresholding using the integral image. Journal of graphics, gpu, and game tools 12, 13-21 (2007).
32. Lander, E. S. et al. Initial sequencing and analysis of the human genome. Nature 409, 860-921, doi:10.1038/35057062 (2001).
33. Kent, W. J. et al. The human genome browser at UCSC. Genome Res 12, 996-1006, doi:10.1101/gr.229102. Article published online before print in May 2002 (2002).
34. Li, H. & Durbin, R. Fast and accurate short read alignment with Burrows-Wheeler transform. Bioinformatics 25, 1754-1760, doi:10.1093/bioinformatics/btp324 (2009).
35. Miller, C. A., Hampton, O., Coarfa, C. & Milosavljevic, A. ReadDepth: a parallel R package for detecting copy number alterations from short sequencing reads. PLoS One 6, e16327, doi:10.1371/journal.pone.0016327 (2011).
36. Pavlova, N. N. & Thompson, C. B. The Emerging Hallmarks of Cancer Metabolism. Cell Metab 23, 27-47, doi:10.1016/j.cmet.2015.12.006 (2016).
37. Tuzun, E. et al., Nat. Genet. 37, 727 (2005).
38. Eichler, E. E. et al., Nature 447, 161 (2007).
39. Derrien, T. et al., PLoS ONE 7, e30377 (2012).
40. Rosenbloom, K. R. et al., Nucleic Acids Res. 43, D670 (2015).
41. Bailey, J. A., Yavor, A. M., Massa, H. F., Trask, B. J., Eichler, E. E., Genome Res. 11, 1005 (2001).
42. Bailey, J. A. et al., Science 297, 1003 (2002).
43. Comaniciu, D. and Meer, P., IEEE Transactions on pattern analysis and machine intelligence 24, 603 (2002).
44. Abyzov, A., Urban, A. E., Snyder, M., Gerstein, M., Genome Res. 21, 974 (2011).
45. The Cancer Genome Atlas (TCGA) Research Network, Nature 455, 1061 (2008).
46. Forbes, S. A. et al., Nucleic Acids Res. 43, D805 (2015).
47. Bozic, I. et al., Proc. Natl. Acad. Sci. U.S.A. 107, 18545 (2010).
48. Pavlova, N. N., Thompson, C. B., Cell Metab. 23, 27 (2016).
49. DeVita, V. T., Young, R. C., Canellos, G. P., Cancer 35, 98 (1975).
50. Del Monte, U., Cell Cycle 8, 505 (2009).
51. Dempsey, M. F., Condon, B. R., Hadley, D. M., AJNR Am J Neuroradiol 26, 770 (2005).
52. Waclaw, B. et al., Nature 525, 261 (2015).
53. Li, X., et al., Cancer Prev Res (Phila) 7, 114 (2014).

| INFORMAL SEQUENCE LISTING Engineered gRNA spacers: | | |
|---|---|---|
| EGFR1 | TCTTGCCGGAATGTCAGCCG | SEQ ID NO: 1 |
| EGFR2 | GTGGAGCCTCTTACACCCAG | SEQ ID NO: 2 |
| EGFR3 | GTCTGCGTACTTCCAGACCA | SEQ ID NO: 3 |
| EGFR4 | TGTCACCACATAATTACCTG | SEQ ID NO: 4 |
| Intergenic1 | ACCCTGTGGCTAATACCATA | SEQ ID NO: 5 |
| Intergenic2 | GTCGGTTACCTTAACCCTCG | SEQ ID NO: 6 |
| Intergenic3 | ATTCTCACATGACCTGACGA | SEQ ID NO: 7 |
| Intergenic4 | TCCCGGCTTACTGCTCTCAA | SEQ ID NO: 8 |
| AAVS1 | CCTGCAACAGATCTTTGATG | SEQ ID NO: 9 |
| AAVS2 | GGTCCAAACTTAGGGATGTG | SEQ ID NO: 10 |
| AAVS3 | AGTACAGTTGGGAAACAACT | SEQ ID NO: 11 |
| AAVS4 | GGCCATTCCCGGCCTCCCTG | SEQ ID NO: 12 |
| Junction1 | GTTTCAAAAGTGAGAACTTT | SEQ ID NO: 13 |
| Junction2 | TCAAAAGTGAGAACTTTGGG | SEQ ID NO: 14 |
| Junction3 | GTGAGAACTTTGGGAGGCTG | SEQ ID NO: 15 |
| NTC1 | TCGATCGAGGTTGCATTCGG | SEQ ID NO: 16 |
| NTC2 | GAATCGACCGACACTAATGT | SEQ ID NO: 17 |
| NTC3 | GCAAACCCGAGTGACACGTC | SEQ ID NO: 18 |

What is claimed is:

1. A method of detecting an amplified extrachromosomal oncogene in a human subject in need thereof, said method comprising:
   (i) obtaining a biological sample from a human subject;
   (ii) sequencing the genome of said human subject from said biological sample;
   (iii) detecting whether an amplified extrachromosomal oncogene is present in said biological sample; and,
   (iv) determining the number of circular extrachromosomal DNA (ecDNA) particles per cancer cell.

2. The method of claim 1, wherein said amplified extrachromosomal oncogene forms part of a circular extrachromosomal DNA.

3. The method of claim 1, wherein said detecting comprises:
   (1) detecting an intracellular location of said amplified extrachromosomal oncogene relative to a standard control;
   (2) mapping said circular extrachromosomal DNA; and
   (3) detecting genetic heterogeneity of said circular extrachromosomal DNA relative to a standard control.

4. A method of detecting an amplified extrachromosomal oncogene in a cancer subject undergoing treatment for cancer, said method comprising:
   (i) obtaining a first biological sample from said cancer subject undergoing treatment for cancer; and
   (ii) sequencing the genome of said human subject from said biological sample;
   (iii) detecting in said first biological sample a first level of an amplified extrachromosomal oncogene; and,
   (iv) determining the number of circular extrachromosomal DNA (ecDNA) particles per cancer cell.

5. The method of claim 4 comprising after step (ii)-(iv):
   (v) obtaining a second biological sample from said subject;
   (vi) detecting in said second biological sample a second level of said amplified extrachromosomal oncogene;
   (vii) determining the number of circular extrachromosomal DNA (ecDNA) particles per cell in said second biological sample; and,
   (viii) comparing said first level to said second level.

6. The method of claim 4, wherein said amplified extrachromosomal oncogene forms part of a circular extrachromosomal DNA.

7. The method of claim 5, wherein said detecting comprises:
   (1) detecting an intracellular location of said amplified extrachromosomal oncogene relative to a standard control;
   (2) detecting a level of said circular extrachromosomal DNA relative to a standard control;
   (3) mapping said circular extrachromosomal DNA; and
   (4) detecting genetic heterogeneity of said circular extrachromosomal DNA.

8. The method of claim 1, wherein said biological sample is a blood-derived biological sample, a urine-derived biological sample, a tumor sample, or a tumor fluid sample.

9. The method of claim 1, wherein said determining the number of circular extrachromosomal DNA (ecDNA) particles per cell comprises preparing metaphase spreads of cells from said biological sample.

10. The method of claim 1, wherein said amplified extrachromosomal oncogene is EGFR, c-Myc, N-Myc, cyclin D1, ErbB2, CDK4, CDK6, BRAF, MDM2, or MDM4.

* * * * *

UNITED STATES PATENT AND TRADEMARK OFFICE
CERTIFICATE OF CORRECTION

| | |
|---|---|
| PATENT NO. | : 11,193,164 B2 |
| APPLICATION NO. | : 15/989100 |
| DATED | : June 7, 2022 |
| INVENTOR(S) | : Mischel et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 288 days.

Signed and Sealed this
Thirty-first Day of January, 2023

Katherine Kelly Vidal
*Director of the United States Patent and Trademark Office*

SEQUENCE LISTING

<160> NUMBER OF SEQ ID NOS: 18

<210> SEQ ID NO 1
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 1
tcttgccgga atgtcagccg                                              20

<210> SEQ ID NO 2
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 2
gtggagcctc ttacacccag                                              20

<210> SEQ ID NO 3
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 3
gtctgcgtac ttccagacca                                              20

<210> SEQ ID NO 4
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 4
tgtcaccaca taattacctg                                              20

<210> SEQ ID NO 5
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 5
accctgtggc taataccata                                              20

<210> SEQ ID NO 6
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 6
gtcggttacc ttaaccctcg                                              20

<210> SEQ ID NO 7
<211> LENGTH: 20
<212> TYPE: DNA
<213> ORGANISM: Artificial sequence

```
<220> FEATURE:
<223> OTHER INFORMATION: Synthetic polynucleotide

<400> SEQUENCE: 7
attctcacat gacctgacga                                               20

<210> SEQ ID NO 8
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 8
tcccggctta ctgctctcaa                                               20

<210> SEQ ID NO 9
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 9
cctgcaacag atctttgatg                                               20

<210> SEQ ID NO 10
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 10
ggtccaaact tagggatgtg                                               20

<210> SEQ ID NO 11
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 11
agtacagttg ggaaacaact                                               20

<210> SEQ ID NO 12
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 12
ggccattccc ggcctccctg                                               20

<210> SEQ ID NO 13
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 13
gtttcaaaag tgagaacttt                                               20
```

```
<210> SEQ ID NO 14
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 14
tcaaaagtga gaactttggg                                              20

<210> SEQ ID NO 15
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 15
gtgagaactt tgggaggctg                                              20

<210> SEQ ID NO 16
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 16
tcgatcgagg ttgcattcgg                                              20

<210> SEQ ID NO 17
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 17
gaatcgaccg acactaatgt                                              20

<210> SEQ ID NO 18
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 18
gcaaacccga gtgacacgtc                                              20
```